(12) United States Patent
Georgiou et al.

(10) Patent No.: US 8,426,187 B2
(45) Date of Patent: Apr. 23, 2013

(54) IMMUNOGLOBULIN LIBRARIES

(75) Inventors: George Georgiou, Austin, TX (US); Yariv Mazor, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 13/288,767

(22) Filed: Nov. 3, 2011

(65) Prior Publication Data

US 2012/0108466 A1  May 3, 2012

Related U.S. Application Data

(62) Division of application No. 11/948,672, filed on Nov. 30, 2007, now Pat. No. 8,067,179.

(60) Provisional application No. 60/867,936, filed on Nov. 30, 2006.

(51) Int. Cl.
  *C12Q 1/68* (2006.01)

(52) U.S. Cl.
  USPC .................. 435/235.1; 435/252.1; 435/252.8; 435/471; 435/472; 435/6.16; 536/25.4

(58) Field of Classification Search .................. None
  See application file for complete search history.

(56) References Cited

U.S. PATENT DOCUMENTS

| | | | |
|---|---|---|---|
| 4,472,509 A | 9/1984 | Gansow et al. | 436/548 |
| 5,021,236 A | 6/1991 | Gries et al. | 424/9 |
| 5,571,698 A | 11/1996 | Ladner et al. | 435/69.7 |
| 5,576,195 A | 11/1996 | Robinson et al. | 435/69.8 |
| 5,578,464 A | 11/1996 | Lunn et al. | 435/69.1 |
| 5,595,898 A | 1/1997 | Robinson et al. | 435/252.33 |
| 5,618,920 A | 4/1997 | Robinson et al. | 530/387.1 |
| 5,648,260 A | 7/1997 | Winter et al. | 435/252.3 |
| 5,693,493 A | 12/1997 | Robinson et al. | 435/69.1 |
| 5,698,417 A | 12/1997 | Robinson et al. | 435/69.1 |
| 5,698,435 A | 12/1997 | Robinson et al. | 435/328 |
| 5,733,743 A * | 3/1998 | Johnson et al. | 435/69.1 |
| 5,766,905 A * | 6/1998 | Studier et al. | 435/235.1 |
| 5,821,047 A * | 10/1998 | Garrard et al. | 435/5 |
| 5,824,520 A | 10/1998 | Mulligan-Kehoe | 435/91.41 |
| 5,837,242 A | 11/1998 | Holliger et al. | 424/136.1 |
| 5,846,818 A | 12/1998 | Robinson et al. | 435/320.1 |

(Continued)

FOREIGN PATENT DOCUMENTS

| WO | WO 2005/019409 | 3/2005 |
|---|---|---|
| WO | 2005/095988 | * 10/2005 |

(Continued)

OTHER PUBLICATIONS

Advisory Action issued in U.S. Appl. No. 11/948,672, dated Nov. 29, 2010.

(Continued)

*Primary Examiner* — Albert Navarro
*Assistant Examiner* — Ginny Portner
(74) *Attorney, Agent, or Firm* — Parker Highlander PLLC

(57) ABSTRACT

Methods and compositions for the screening and isolation of ligand-binding polypeptides, such as antibodies. In some aspects, methods of the invention enable the isolation of intact soluble antibodies comprising a constant domain. Screening methods that employ genetic packages such as bacteria and bacteriophages enable high through-put identification of ligand binding molecules.

10 Claims, 26 Drawing Sheets

U.S. PATENT DOCUMENTS

| | | | | |
|---|---|---|---|---|
| 5,858,657 | A | 1/1999 | Winter et al. | 435/6.14 |
| 5,922,545 | A | 7/1999 | Mattheakis et al. | 435/6 |
| 5,939,317 | A | 8/1999 | Fayard et al. | 435/320.1 |
| 5,961,979 | A | 10/1999 | Srivastava | 424/193.1 |
| 5,994,514 | A | 11/1999 | Jardieu et al. | 530/388.22 |
| 6,172,197 | B1 | 1/2001 | McCafferty et al. | 530/387.3 |
| 6,194,551 | B1* | 2/2001 | Idusogie et al. | 530/387.1 |
| 6,204,023 | B1 | 3/2001 | Robinson et al. | 435/71.3 |
| 6,248,516 | B1 | 6/2001 | Winter et al. | 435/6.16 |
| 6,277,375 | B1* | 8/2001 | Ward | 424/133.1 |
| 6,331,415 | B1 | 12/2001 | Cabilly et al. | 435/69.6 |
| 6,455,279 | B1 | 9/2002 | Ambrosius et al. | 435/69.1 |
| 6,500,641 | B1 | 12/2002 | Chen et al. | 435/69.1 |
| 6,545,142 | B1 | 4/2003 | Winter et al. | 536/24.33 |
| 6,555,313 | B1* | 4/2003 | Griffiths et al. | 506/9 |
| 6,667,150 | B1 | 12/2003 | Rudert et al. | 506/14 |
| 6,696,248 | B1 | 2/2004 | Knappik et al. | 435/6.16 |
| 6,737,056 | B1 | 5/2004 | Presta | 424/133.1 |
| 6,806,079 | B1 | 10/2004 | McCafferty et al. | 435/320.1 |
| 6,846,653 | B2 | 1/2005 | Kolkman | 435/69.8 |
| 6,979,538 | B2 | 12/2005 | Ladner et al. | 435/6.16 |
| 6,979,556 | B2 | 12/2005 | Simmons et al. | 435/69.1 |
| 6,989,250 | B2 | 1/2006 | Soderlind et al. | 435/91.2 |
| 7,083,945 | B1 | 8/2006 | Chen et al. | 435/69.1 |
| 7,094,571 | B2 | 8/2006 | Harvey et al. | 435/69.1 |
| 7,118,879 | B2 | 10/2006 | Ladner et al. | 435/6 |
| 7,183,076 | B2* | 2/2007 | Arathoon et al. | 435/69.1 |
| 7,202,055 | B2 | 4/2007 | Schafer et al. | 435/69.1 |
| 7,229,792 | B2 | 6/2007 | Pandiripally | 435/69.1 |
| 7,264,963 | B1 | 9/2007 | Knappik et al. | 435/320.1 |
| 7,317,091 | B2 | 1/2008 | Lazar et al. | 530/387.1 |
| 7,371,826 | B2 | 5/2008 | Presta | 530/387.1 |
| 7,419,783 | B2* | 9/2008 | Georgiou et al. | 435/6.16 |
| 7,435,549 | B1 | 10/2008 | Kufer et al. | 435/7.1 |
| 7,435,553 | B2* | 10/2008 | Fandl et al. | 435/7.2 |
| 7,611,866 | B2 | 11/2009 | Georgiou et al. | 435/69.1 |
| 7,632,924 | B2 | 12/2009 | Cho et al. | 530/387.3 |
| 7,662,925 | B2 | 2/2010 | Lazar et al. | 530/387.1 |
| 7,951,917 | B1* | 5/2011 | Arathoon et al. | 530/387.3 |
| 7,985,573 | B2* | 7/2011 | Yacoby et al. | 435/235.1 |
| 8,067,179 | B2* | 11/2011 | Georgiou et al. | 435/6.16 |
| 2002/0025536 | A1* | 2/2002 | Gyuris et al. | 435/7.1 |
| 2003/0104604 | A1* | 6/2003 | Yang et al. | 435/235.1 |
| 2003/0180937 | A1 | 9/2003 | Georgiou et al. | 435/252.8 |
| 2003/0219870 | A1 | 11/2003 | Georgiou et al. | 530 |
| 2004/0058400 | A1* | 3/2004 | Holliger et al. | 435/7.23 |
| 2004/0132101 | A1 | 7/2004 | Lazar et al. | 435/7.1 |
| 2004/0253242 | A1 | 12/2004 | Bowdish et al. | 424/145.1 |
| 2005/0169932 | A1 | 8/2005 | Cheung | 424/160.1 |
| 2005/0186623 | A1* | 8/2005 | Fandl et al. | 435/6 |
| 2005/0191749 | A1 | 9/2005 | Bowdish et al. | 435/476 |
| 2005/0249723 | A1 | 11/2005 | Lazar | 424/133.1 |
| 2005/0260736 | A1* | 11/2005 | Georgiou et al. | 435/252.3 |
| 2006/0029947 | A1 | 2/2006 | Georgiou et al. | 435 |
| 2006/0115874 | A1* | 6/2006 | Garrard et al. | 435/69.1 |
| 2006/0147997 | A1 | 7/2006 | Ramarkrishnan | 435/7.1 |
| 2006/0173170 | A1 | 8/2006 | Chamberlain et al. | 530/387.3 |
| 2006/0205016 | A1* | 9/2006 | Silverman | 435/7.1 |
| 2006/0234311 | A1* | 10/2006 | Fandl et al. | 435/7.2 |
| 2007/0065913 | A1 | 3/2007 | Chen et al. | 435/69.1 |
| 2007/0099247 | A1 | 5/2007 | Daugherty et al. | 435/7.2 |
| 2007/0099267 | A1 | 5/2007 | Harvey et al. | 435/69.1 |
| 2007/0178447 | A1* | 8/2007 | McIntush et al. | 435/5 |
| 2008/0057038 | A1* | 3/2008 | Yacoby et al. | 424/93.6 |
| 2008/0206817 | A1 | 8/2008 | Brass et al. | 435/69.6 |
| 2010/0004134 | A1* | 1/2010 | Horowitz et al. | 506/2 |
| 2011/0124516 | A1* | 5/2011 | Rehm et al. | 506/9 |
| 2011/0286970 | A1* | 11/2011 | Solomon et al. | 424/93.2 |

FOREIGN PATENT DOCUMENTS

| | | |
|---|---|---|
| WO | WO 2005/095988 | 10/2005 |
| WO | 2005/103074 | * 11/2005 |
| WO | 2006/095345 | * 9/2006 |

OTHER PUBLICATIONS

Advisory Action issued in U.S. Appl. No. 11/948,672, dated Nov. 4, 2010.

Baneyx and Mujacic, "Recombinant protein folding and misfolding in *Escherichia coli*," *Nat. Biotechnol.*, 22:1399-1408, 2004.

Boss et al., "Assembly of functional antibodies from immunoglobulin heavy and light chains synthesised in *E. coli*," *Nucleic Acids Res.*, 12:3791-3806, 1984.

Cabilly et al., "Generation of antibody activity from immunoglobulin polypeptide chains produced in *Escherichia coli*," *Proc. Natl. Acad. Sci. USA*, 81:3273-3277, 1984.

Canziani et al., "Kinetic screening of antibodies from crude hybridoma samples using Biacore," *Anal Biochem.*, 325(2):301-307, 2004.

Chames et al., "Direct selection of a human antibody fragment directed against the tumor T-cell epitope HLA-A1-MAGE-A1 from a nonimmunized phage-Fab library," *Proc. Natl. Acad. Sci. USA*, 97:7969-7974, 2000.

Chen et al., "In vitro scanning saturation mutagenesis of all the specificity determining residues in an antibody binding site," *Protein Eng.*, 12:349-356, 1999.

Chen et al., "Isolation of high-affinity ligand-binding proteins by periplasmic expression with cytometric screening (PECS)," *Nature Biotechnology*, 19(6):537-542, 2001.

Desai et al., "Characterization of human anti-high molecular weight-melanoma-associated antigen single-chain Fv fragments isolated from a phage display antibody library," *Cancer Res.*, 58:2417-2425, 1998.

Georgiou, "Analysis of large libraries of protein mutants using flow cytometry," *Adv. Protein Chem.*, 55:293-315, 2000.

Gleiter et al., "Coupling of antibodies via protein Z on modified polyoma virus-like particles," *Protein Science*, 10(2): 434-444, 2001.

Griffiths and Duncan, "Strategies for selection of antibodies by phage display," *Curr. Opin. Biotechnol.*, 9:102-108, 1998.

Harvey et al., "Anchored periplasmic expression, a versatile technology for the isolation of high-affinity antibodies from *Escherichia coli*-expressed libraries," *Proc. Natl. Acad. Sci. USA*, 101, 9193-9198, 2004.

Harvey et al., "Engineering of recombinant antibody fragments to methamphetamine by anchored periplasmic expression," *J. Immunol. Methods*, 308:43-52, 2006.

Harvey, "Anchored periplasmic expression (APEX) of protein libraries for flow cytometric selection," *Abstracts of Paper. At The National Meeting, American Chemical Society*, 224(1/02):BIOT-324, 2002.

Hayhurst et al., "Isolation and expression of recombinant antibody fragments to the biological warfare pathogen *Brucella melitensis*," *J. Immunol. Methods*, 276:185-196, 2003.

Hoet et al., "Generation of high-affinity human antibodies by combining donor-derived and synthetic complementarity-determining-region diversity," *Nat. Biotechnol.*, 23:344-348, 2005.

Hoogenboom and Winter, "By-passing immunisation. Human antibodies from synthetic repertoires of germline VH gene segments rearranged in vitro," *J. Mol. Biol.*, 227:381-388, 1992.

Hoogenboom et al., "Antibody phage display technology and its applications," *Immunotechnology*, 4:1-20, 1998.

Hoogenboom, "Overview of antibody phage-display technology and its applications," *Methods Mol. Biol.*, 178:1-37, 2002.

Huie et al., "Antibodies to human fetal erythroid cells from a nonimmune phage antibody library," *Proc. Natl. Acad. Sci. USA*, 98:2682-2687, 2001.

International Search Report and Written Opinion, issued in International Application No. PCT/US2007/086131, dated Nov. 25, 2008.

Jeong et al., "APEx 2-hybrid, a quantitative protein-protein interaction assay for antibody discovery and engineering," *Proceedings of the National Academy of Sciences of the United States of America*, 104(20):8247-8252, 2007.

Jung et al., "Binding and enrichment of *Escherichia coli* spheroplasts expressing inner membrane tethered scFv antibodies on surface immobilized antigens," *Biotechnology and Bioengineering*, 98(1):39-47, 2007.

Kipriyanov and Little, "Generation of recombinant antibodies," *Mol. Biotechnol.*, 12:173-201, 1999.

Kjaer et al., "Glycerol diversifies phage repertoire selections and lowers non-specific phage absorption," *FEBS Lett.*, 431:448-452, 1998.

Knappik et al., "Fully synthetic human combinatorial antibody libraries (HuCAL) based on modular consensus frameworks and CDRs randomized with trinucleotides," *J. Mol. Biol.*, 296:57-86, 2000.

Knight et al., "The immunogenicity of the 7E3 murine monoclonal Fab antibody fragment variable region is dramatically reduced in humans by substitution of human for murine constant regions," *Mol. Immunol.*, 32:1271-1281, 1995.

Kramer et al., "The human antibody repertoire specific for rabies virus glycoprotein as selected from immune libraries," *Eur. J. Immunol.*, 35:2131-2145, 2005.

Lipovsek and Pluckthun, "In-vitro protein evolution by ribosome display and mRNA display," *J. Immunol. Methods*, 290:51-67, 2004.

Lu et al., "Tailoring in vitro selection for a picomolar affinity human antibody directed against vascular endothelial growth factor receptor 2 for enhanced neutralizing activity," *J. Biol. Chem.*, 278:43496-507, 2003.

Masuda et al., "Elucidation of the function of lipoprotein-sorting signals that determine membrane localization," *Proc Natl. Acad. Sci. USA*, 99(11):7390-7395, 2002.

Mazor et al., "Isolation of engineered, full-length antibodies from libraries expressed in *Escherichia coli*," *Nature Biotechnology*, 25(5):563-565, 2007.

Mossner et al., "Fast selection of antibodies without antigen purification: adaptation of the protein fragment complementation assay to select antigen-antibody pairs," *Journal of Molecular Biology*, 308(2):115-122, 2001.

Moulard et al., "Broadly cross-reactive HIV-1-neutralizing human monoclonal Fab selected for binding to gp120-CD4-CCR5 complexes," *Proc. Natl. Acad. Sci. USA*, 99:6913-6918, 2002.

Notice of Allowance issued in U.S. Appl. No. 11/948,672, dated Jul. 27, 2011.

Office Communication issued in European Patent Application No. 07 865 029.8, dated Jul. 5, 2010.

Office Communication issued in European Patent Application No. 07 865 029.8, dated Apr. 12, 2011.

Office Communication issued in U.S. Appl. No. 11/948,672, dated Oct. 15, 2010.

Office Communication issued in U.S. Appl. No. 11/948,672, dated May 25, 2010.

Office Communication issued in U.S. Appl. No. 11/948,672, dated Jan. 28, 2010.

Ohno et al., "Cell-specific targeting of IgG-binding domains of protein A," *Nature Biotechnology*, 15:763-767, 1997.

Ohno et al., "Retrovirus vectors displaying the IGG-binding domain of protein A," *Biochemical and Molecular Medicine*, 62(1):123-127, 1997.

Partial International Search Report and Invitation to Pay Additional Fees, issued in International Application No. PCT/US2007/086131, dated Aug. 8, 2008.

Pini and Bracci, "Phage display of antibody fragments," *Curr. Protein Pept. Sci.*, 1:155-169, 2000.

Simmons et al., "Expression of full-length immunoglobulins in *Escherichia coli*: rapid and efficient production of aglycosylated antibodies," *J. Immunol. Methods*, 263:133-147, 2000.

W.D. Shen, Amgen, "Selecting and screening recombinant antibody libraries," *Nat. Biotechnol.*, 23:1105-1116, 2005.

Yacoby et al., "Targeting antibacterial agents by using drug-carrying filamentous bacteriophages," *Antimicrob. Agents Chemother.*, 50:2087-2097, 2006.

\* cited by examiner

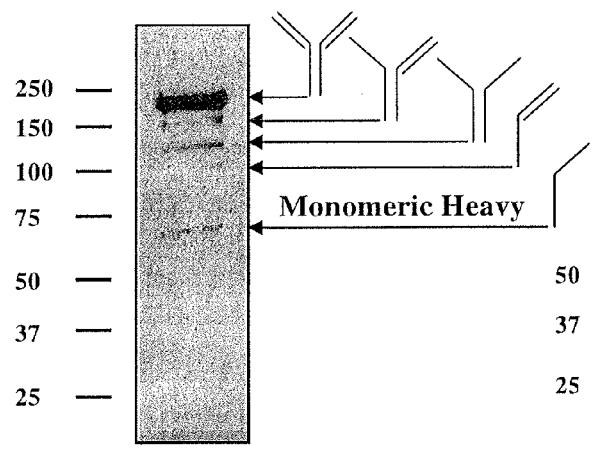
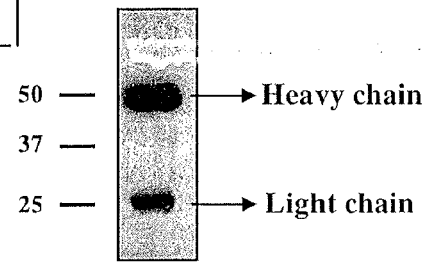
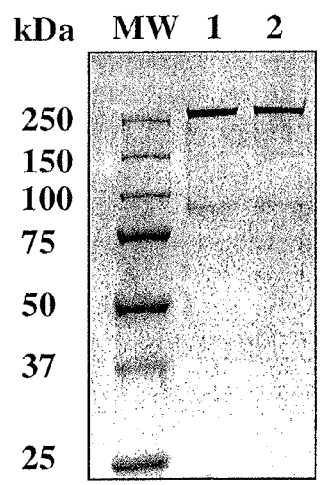
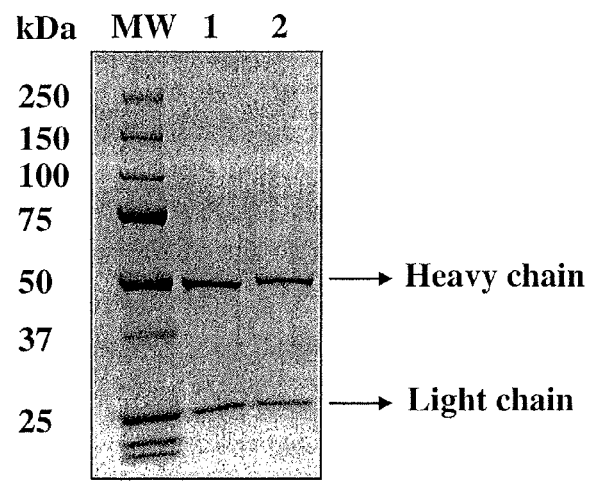
FIG. 3

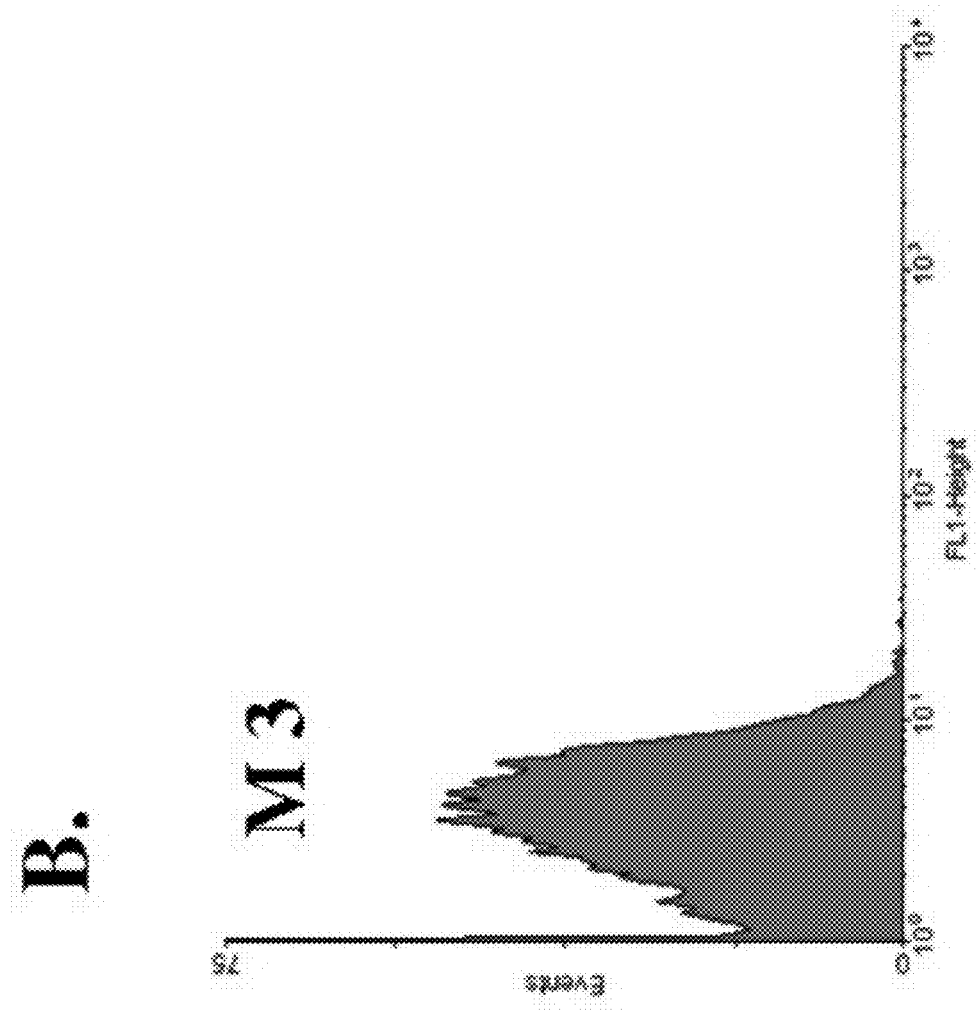

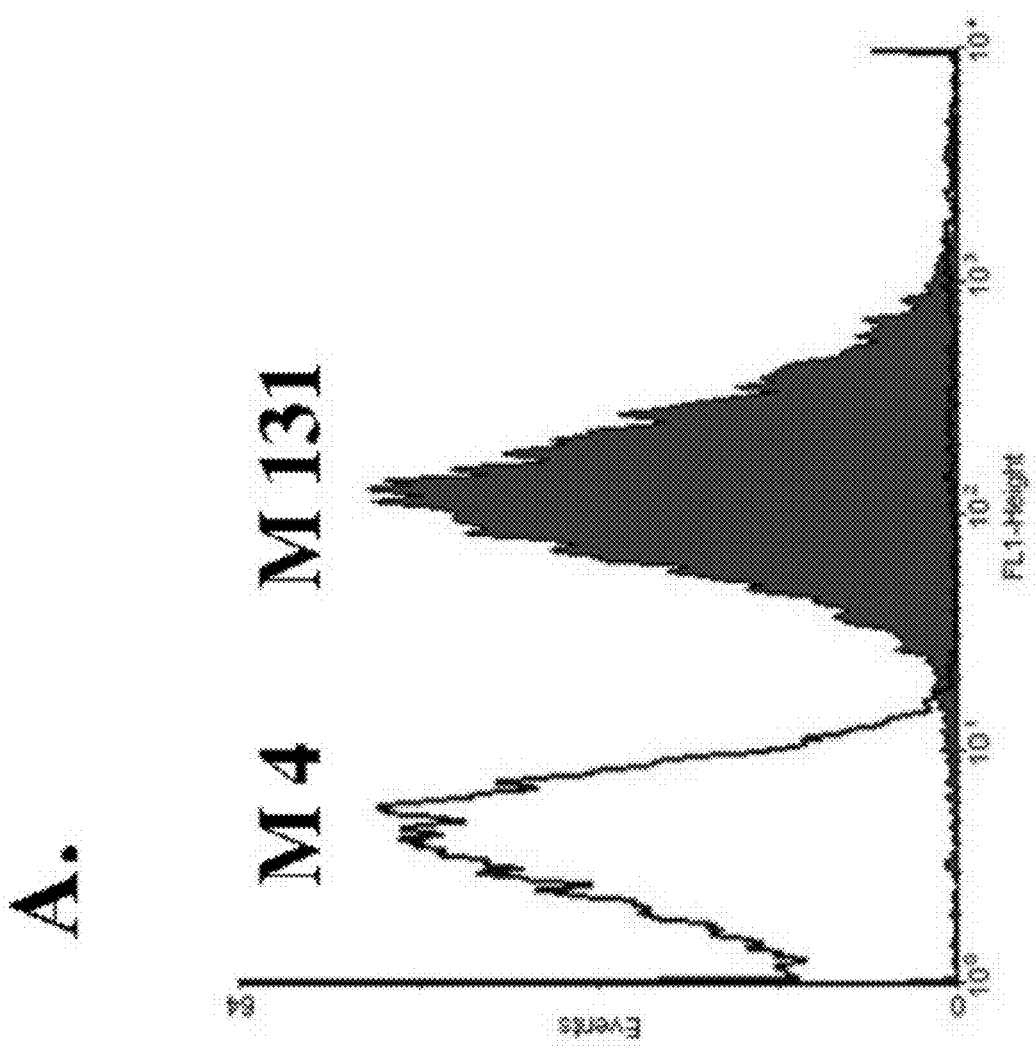

VH

|  | FR1 | CDR1 | FR2 | CDR2 |
|---|---|---|---|---|
| YMB2 | EVQLQQSGAELVKPGASVKLSCTASG | FNIKDTYMH | WVKQRPEQGLEWIG | RIDPENGNTKYDPKFQG |
| YMD1 | ....VE......RS............ | .....Y... | ............... | W......D.E.A..... |
| YMF10 | ...........RS............ | .....Y... | ............... | W......D.E.A..... |
| YMC3 | Q...K................K... | YTFTSYDIN | ..R............ | W.F.GD.S...NE..K. |
| YMH2 | ..K.....P.........I..KG.. | YA.SSSW.N | ......G..P.... | ..Y.GD.D.N.NG..K. |

|  | FR3 | CDR3 | FR4 |
|---|---|---|---|
| YMB2 | KATITADTSSNTAYLQLSSLTSEDTAVYYCAR | FLITTGYFDY | WGQGTTLTVSS |
| YMD1 | ...M........................NA | GTPFEGLRKADY | ........... |
| YMF10 | ...MS.......................NA | GTPFEGLRRADY | ........... |
| YMC3 | ...L.T.K..S...M...R.....S...F... | GGLYFDY | ........... |
| YMH2 | ...L...K..S...M.......V.S...F... | GGLPYAVDY | .....SV.... |

VL

|  | FR1 | CDR1 | FR2 | CDR2 |
|---|---|---|---|---|
| YMB2 | DIVLTQSHKFMSTSVGDRVSITC | KASQDVGTAVA | WYQQKPGQSPKLLIY | WASTRHT |
| YMD1 | ...MT....L............. | ........... | ..........R.... | ....... |
| YMF10 | ...MT................. | ........... | ............... | ....... |
| YMC3 | ..QMT..PSSL.A......TV.. | R...GIRNYLN | .......KA..F... | YT.RLLP |
| YMH2 | ..QMT..PSSL.A......TV.. | R...GIRNYLN | .......KA..F... | YT.RLLP |

|  | FR3 | CDR3 | FR4 |
|---|---|---|---|
| YMB2 | GVPDRFTGSGSGTDFTLTISNVQSEDLADYFC | QQYSSYPLT | FGAGTKLEIKR |
| YMD1 | ....................T........... | ........Y. | ..G........ |
| YMF10 | ................................ | .......... | ........LN. |
| YMC3 | ...S..S.......Y....NSLEQ..I.T.Y. | ..GNTP.W. | ..Q...V.... |
| YMH2 | ...S..S.......Y....NSLEQ..I.T.Y. | ..GNTP.W. | ..Q...V.... |

FIG. 10

A.
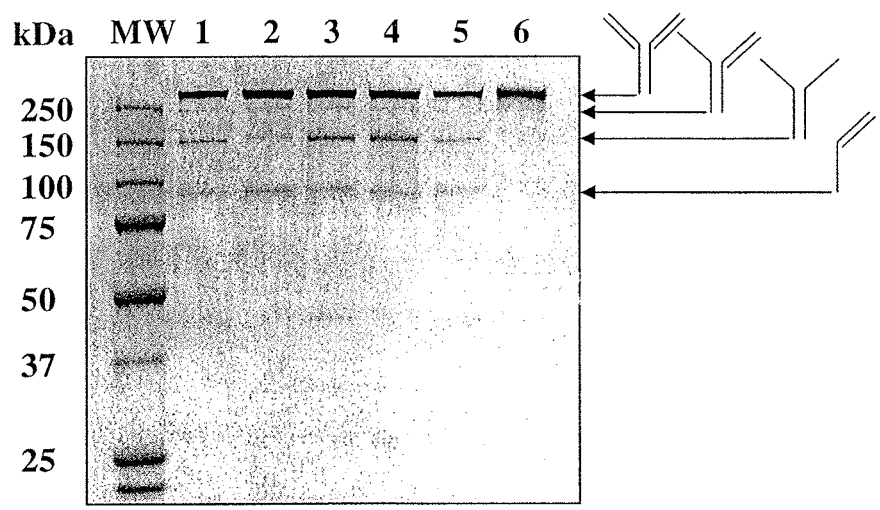
B.
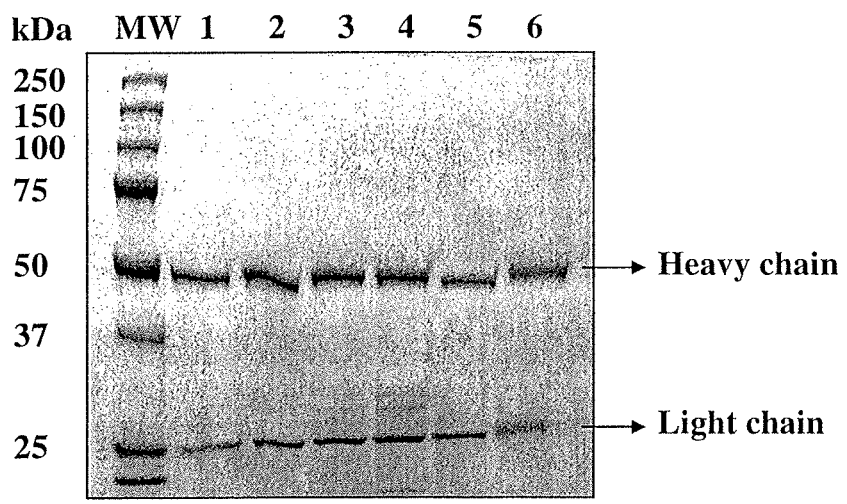
FIG. 12

A

| Antibody | $k_{on}$ ( M$^{-1}$ sec$^{-1}$) | $k_{off}$ ( sec$^{-1}$) | $K_D$ (nM) |
|---|---|---|---|
| YMB2[a] | 3.2 x 10$^4$ | 1.4 x 10$^{-2}$ | 437 |
| YMD1[b] | 3.5 x 10$^5$ | 1.9 x 10$^{-2}$ | 55 |
| YMF10[b] | 4.9 x 10$^5$ | 1.5 x 10$^{-2}$ | 31 |
| YMC3[c] | 6.8 x 10$^5$ | 3.2 x 10$^{-2}$ | 47 |
| YMH2[c] | 1.3 x 10$^6$ | 2.7 x 10$^{-2}$ | 21 |

[a] Affinity was determined by direct binding of the IgG to PA-63 immobilized chip.
[b] Affinity was determined by IgG capturing by anti-Fc antibody followed by injection of PA-63 as analyte.
[c] Affinity was determined by direct binding of the IgG to PA-83 immobilized chip.

B

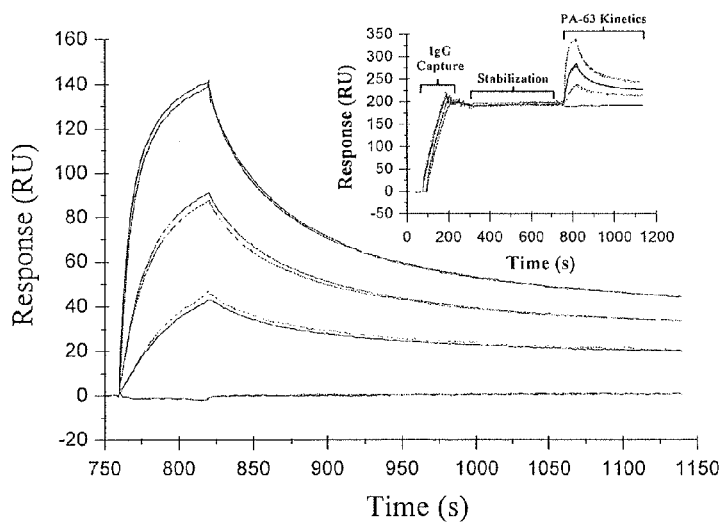

FIG. 13

A.
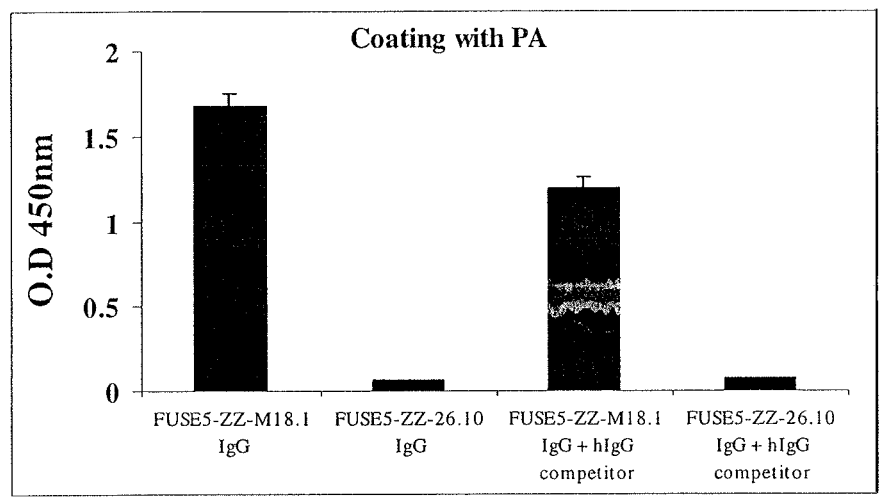
B.
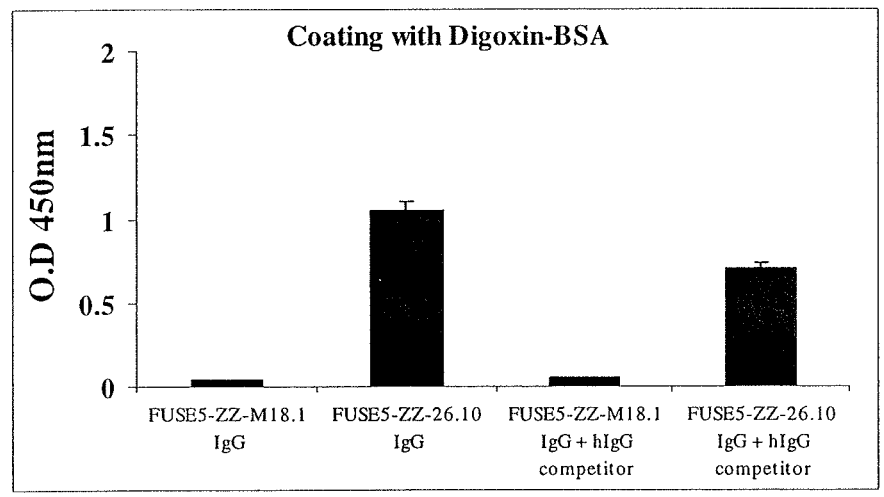
FIG. 15

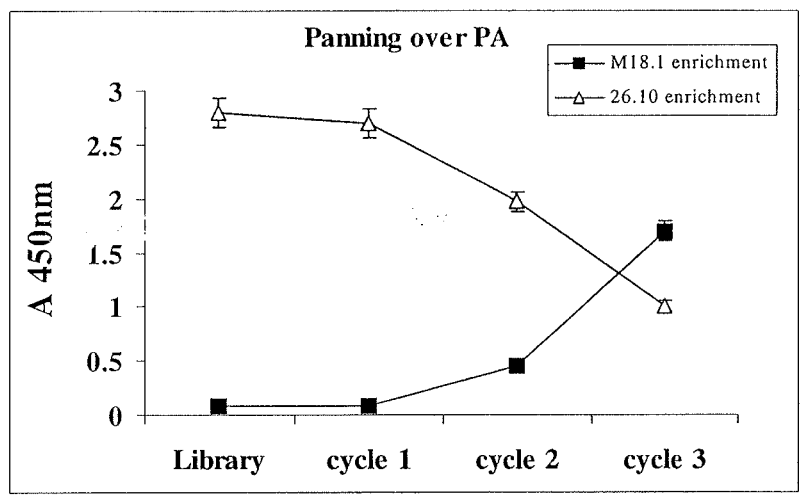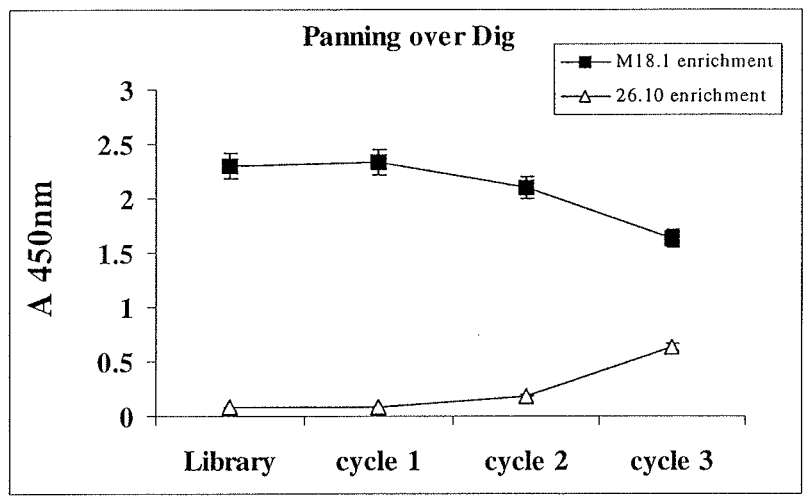
FIG. 16

A
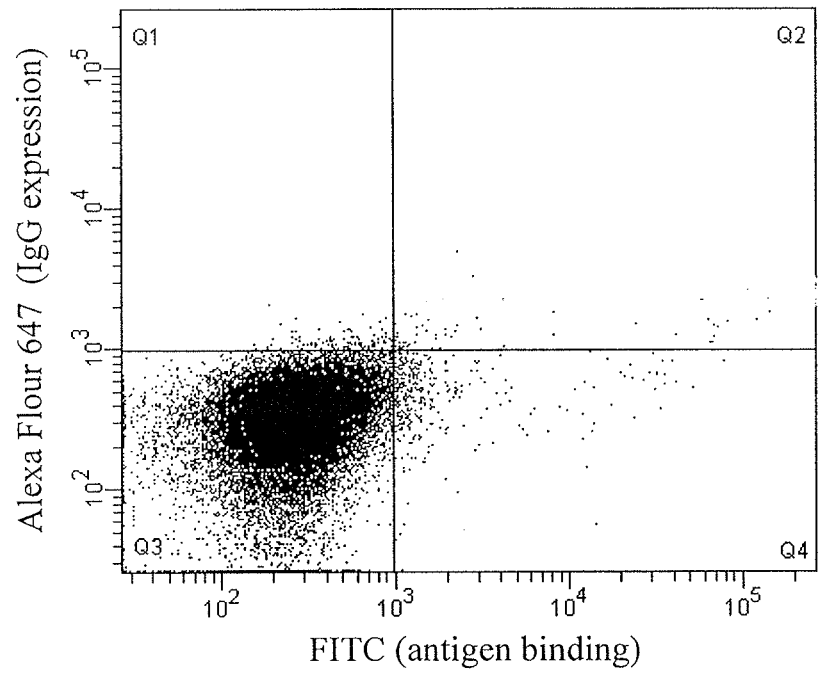
B
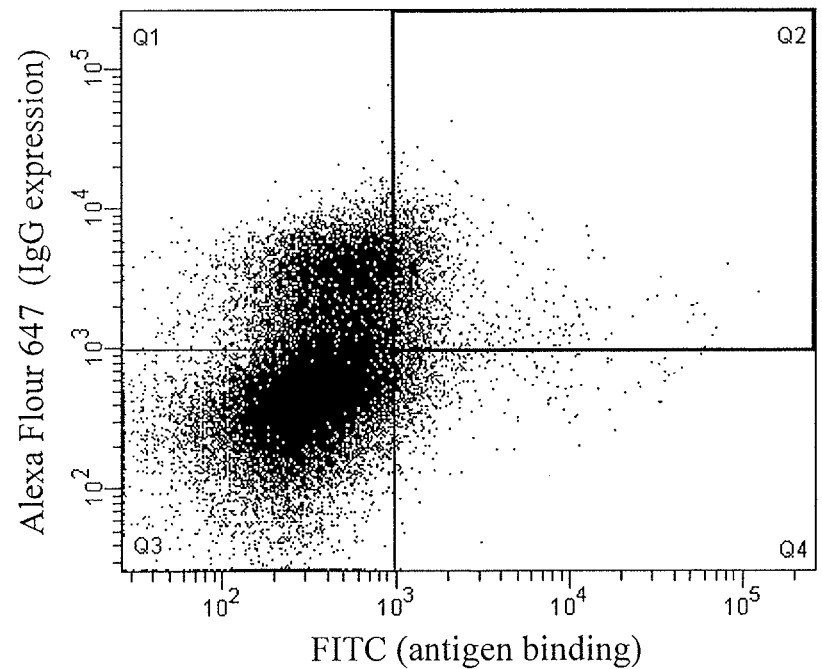
FIG. 18

IMMUNOGLOBULIN LIBRARIES

CROSS REFERENCE TO PRIOR APPLICATIONS

The present application is a divisional of application Ser. No. 11/948,672 filed Nov. 30, 2007 now U.S. Pat. No. 8,067,179, which application claims priority to U.S. Provisional Patent Application Ser. No. 60/867,936, filed on Nov. 30, 2006, which is incorporated by reference herein in its entirety.

BACKGROUND OF THE INVENTION

1. Field of the Invention

The present invention relates generally to the field of protein engineering. More particularly, it concerns improved methods and compositions for the screening of combinatorial antibody libraries expressed in bacteria.

2. Description of Related Art

Currently recombinant therapeutic antibodies have sales of well over $10 bn/yr and with a forecast of annual growth rate of 20.9% they are projected to increase to $25 bn/yr by 2010. Monoclonal antibodies (mAbs) now comprise the majority of recombinant proteins currently in the clinic, with more than 150 products in studies sponsored by companies located worldwide (Pavlou and Belsey, 2005). In terms of therapeutic focus, the mAb market is heavily focused on oncology and arthritis, immune and inflammatory disorders, and products within these therapeutic areas are set to continue to be the key growth drivers over the forecast period. As a group, genetically engineered mAbs generally have higher probability of FDA approval success than small-molecule drugs. At least 50 biotechnology companies and all the major pharmaceutical companies have active antibody discovery programs in place.

The original method for isolation and production of mAbs was first reported at 1975 by Milstein and kohler (Kohler and Milstein, 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consuming related to the technology became driving forces for the evolution of mAb production technology. Polymerase Chain Reaction (PCR) facilitated the cloning of monoclonal antibodies genes directly from lymphocytes of immunized animals and the expression of combinatorial library of fragments antibodies in bacteria (Orlandi et al., 1989). Later libraries were created entirely by in vitro cloning techniques using naïve genes with rearranged complementarity determining region 3 (CDR3) (Griffiths and Duncan, 1998; Hoogenboom et al., 1998). As a result, the isolation of antibody fragments with the desired specificity was no longer dependent on the immunogenicity of the corresponding antigen. Moreover, the range of antigen specificities in synthetic combinatorial libraries was greater than that found in a panel of hybridomas generated from an immunized mouse. These advantages have facilitated the development of antibody fragments to a number of unique antigens including small molecular compounds (haptens) (Hoogenboom and Winter, 1992), molecular complexes (Chames et al., 2000), unstable compounds (Kjaer et al., 1998) and cell surface proteins (Desai et al., 1998).

During the past decade several display methods and other library screening techniques have been developed for isolating antigen specific binders from large ensembles of recombinant antibody fragments. These technologies are now widely exploited to engineer antibody fragments with high affinity and specificity. Many of these screening platforms share four key steps with the procedure for antibody generation in the in vivo immune system: first, the generation of genotypic diversity; second, the coupling of genotype to phenotype; third, the application of selective pressure; and fourth, amplification.

Phage display is currently the most widespread method for the display and selection of large collections of antibody fragments (Hoogenboom, 2002). In this methodology, a gene of interest is fused in-frame to phage genes encoding surface-exposed proteins, most commonly pIII. The gene fusions are translated into chimeric proteins in which the two domains fold independently. Phage displaying a protein with binding affinity for a ligand can be readily enriched by selective adsorption onto immobilized ligand, a process known as "panning". The bound phage is desorbed from the surface, usually by acid elution, and amplified through infection of E. coli cells. Usually, 4-6 rounds of panning and amplification are sufficient to select for phage displaying specific polypeptides, even from a very large libraries with diversities up to $10^{10}$. The most successful application of phage display include the following: first, the de novo isolation of high-affinity human antibody fragments from nonimmune and synthetic libraries (Griffiths et al., 1994; Vaughan et al., 1996; de Haard et al., 1999; Knappik et al., 2000; Hoet et al., 2005), including antibody fragments against self antigens; second, the generation of picomolar affinity antibodies by in vitro affinity maturation (Yang et al., 1995; Schier et al., 1996; Lu et al., 2003) and third, the discovery of antibody fragments with unique properties from non-immune (Chames et al., 2000; Huie et al., 2001) and immune libraries from animal or human donors (Moulard et al., 2002; Kramer et al., 2005).

Ribosome and mRNA display represent another method for the display and screening of libraries of antibody fragments. The concept relays on the stable formation of a complex of antibody fragment and its encoding mRNA (Lipovsek and Pluckthun, 2004). In ribosome display, the link between antibody fragment and encoding mRNA is made by the ribosome, which at the end of translating this mRNA is made to stop without releasing the polypeptide. The ternary complex as a whole is used for the selection. In mRNA display, there is a covalent bond between the antibody fragment protein and the mRNA which is established via puromycin as an adaptor molecule. These display methods are carried out entirely in vitro.

In microbial cell display screening is carried out by flow cytometry. In particular, Anchored Periplasmic Expression (APEx) is based on anchoring the antibody fragment on the periplasmic face of the inner membrane of E. coli followed by disruption of the outer membrane, incubation with fluorescently labeled antigen and sorting of the spheroplasts. APEx was used for the affinity maturation of antibody fragments (Harvey et al., 2004; Harvey et al., 2006). In one study over 200-fold affinity improvement was obtained after only two rounds of screening.

Nonetheless, all high throughput antibody screening technologies available to-date rely on microbial expression of antibody fragments. The use of antibody fragments rather than intact or full length IgGs, in the construction and screening of libraries has been dictated by limitations related to the expression of the much larger IgGs in microorganisms. IgG libraries have never before been expressed or screened using microorganisms such as bacteria or yeasts. As a result the isolation of antigen binding proteins has been carried out exclusively using antibody fragments that are smaller and much easier to produce. Once isolated such antibody fragments have to then fused to vectors that express full length immunoglobulins which in turn are expressed preferentially in mammalian cells such as CHO cells.

Antibody fragments, including Fabs and especially single chain Fv's (scFv), pose several limitations: (1) Antibody fragments often exhibit low affinity for the target antigen. Unlike IgG or IgM antibodies antibody fragments are monovalent and therefore they cannot capitalize on avidity effects for stronger binding to antigens (Pini and Bracci, 2000). Thus, the isolation of recombinant antibody fragments to targets that cannot be recognized with high affinity e.g. carbohydrates, is problematic. (2) Antibody fragments generally exhibit lower thermodynamic stability than their corresponding full length IgG counterparts (Worn and Pluckthun, 2001). (3) Because of their small size and their lack of an Fc region, antibody fragments exhibit very short circulation half-lives compared to full length IgG proteins (Milenic et al., 1991). Therefore for the vast majority of clinical applications antibody fragments isolated from combinatorial libraries have to be converted to full length IgG molecules.

The need for isolating intact IgG molecules from combinatorial libraries has long been recognized. In an attempt to establish a platform for the isolation of recombinant IgGs, researchers recently displayed small libraries of IgGs on the surface of mammalian cells. After homologous integration of a single-gene copy in each cell, the population was sorted by flow cytometry to obtain single selected clones (W. D. Shen, Amgen, cited by Hoogenboom (2005)). Nevertheless, this technology is time-consuming, cumbersome, and expensive and is not amenable to the screening of large libraries comprising of many tens of millions of different antibody proteins. The present invention overcomes these limitations by avoiding the need for expression of IgG libraries in mammalian cells. Instead, the inventors have devised methodologies for the screening of libraries produced and secreted by *E. coli* bacteria.

*E. coli* possesses a reducing cytoplasm that is unsuitable for the folding of proteins with disulfide bonds which accumulate in an unfolded or incorrectly folded state (Baneyx and Mujacic, 2004). In contrast to the cytoplasm, the periplasm of *E. coli* is maintained in an oxidized state that allows the formation of protein disulfide bonds. Notably, periplasmic expression has been employed successfully for the expression of antibody fragments such as Fvs, scFvs, Fabs or F(ab')2s (Kipriyanov and Little, 1999). These fragments can be made relatively quickly in large quantities with the retention of antigen binding activity. However, because antibody fragments lack the Fc domain, they do not bind the FcRn receptor and are cleared quickly; thus, they are only occasionally suitable as therapeutic proteins (Knight et al., 1995). Until recently, full-length antibodies could only be expressed in *E. coli* as insoluble aggregates and then refolded in vitro (Boss et al., 1984; Cabilly et al., 1984). Clearly this approach is not amenable to the high throughput screening of antibody libraries since, with the current technology it is not possible to refold millions or tens of millions of antibodies individually. The expression of full length IgG antibodies in secreted form in *E. coli* was reported only recently (Simmons et al., 2002). However, there is no information on whether antibody libraries consisting of many different antibodies can also be expressed in bacteria. Equally importantly, the prior art does not disclose any methods for isolating *E. coli* cells expressing a particular IgG with specificity towards a desired antigen from a vast excess of cells expressing IgGs of unrelated specificities.

*E. coli* expressed antibodies are not glycosylated, and fail to bind to complement factor 1q (C1q) or FcγRI and thus cannot elicit complement activation or mediate the recruitment of macrophages. However, aglycosylated Fc domains can bind to the neonatal Fc receptor efficiently (FcRn). Consequently bacterially expressed aglycosylated antibodies exhibit serum persistence and pharmacokinetics similar to those of fully glycosylated IgGs produced in human cells.

SUMMARY OF THE INVENTION

In a first embodiment the invention provides a Gram negative bacterial cell wherein the cell comprises (a) an antibody-binding domain expressed in the periplasm of the Gram negative bacterial cell and (b) an antibody bound to said antibody-binding domain. The skilled artisan will recognize that a Gram negative bacteria comprises an inner and outer membrane and a periplasmic space between the two membranes. Thus, an antibody-binding domain of the invention will be anchored on or in the inner membrane and may be positioned such that antibody-binding domain is exposed to the periplasmic space. Thus, an antibody bound to such an antibody-binding domain will be expressed in the periplasmic space. Methods for expressing polypeptides and in particular antibodies in the periplasmic space are known in the art for example see U.S. Pat. No. 7,094,571 and U.S. Patent Publ. 20030180937 and 20030219870 each incorporated herein by reference. In some cases a gram negative bacterial cell of the invention may be defined as an *E. coli* cell. Furthermore, in some preferred aspects a Gram negative bacterial cell of the invention may defined as a genetically engineered bacterial cell such as a JUDE-1 strain of *E. coli*. Gram negative bacterial cells of the invention may be viable or non-viable cells. Furthermore, in some aspects, Gram negative bacterial cells of the invention are defined as cells lacking an intact outer membrane such that the periplasmic space is in contact with the extra cellular environment, in some cases cells lacking an outer membrane are referred to as spheroplasts. Methods for disrupting, permeablizing or removing the outer membrane of bacteria are well known in the art for example see U.S. Pat. No. 7,094,571. For instance, the outer membrane of the bacterial cell may be treated with hyperosmotic conditions, physical stress, lysozyme, EDTA, a digestive enzyme, a chemical that disrupts the outer membrane, or by infecting the bacterium with a phage or a combination of the foregoing methods. Thus, in some cases, the outer membrane may be disrupted by lysozyme and EDTA treatment.

In further aspects of the invention, an antibody bound to an antibody-binding domain that is comprised in the bacterial periplasm may be anchored to the inner membrane of a bacterial cell. Such an antibody binding domain may comprise a constant domain (Fc) such as an immunoglobulin heavy chain constant domain. Thus, in some aspects of the invention an antibody may comprise two immunoglobulin heavy chains and two immunoglobulin light chains. In certain cases, each of the heavy and light chains comprise both a variable and a constant domain or fragments thereof. However, in some aspects, immunoglobulin heavy and light chains of the invention comprise functional domain fragments of the variable and/or constant domains. As used herein the term functional domain fragment means that antibodies composed of said fragments are capable of binding to a target antigen (in the case of a variable domain fragment) or an Fc specific antibody-binding domain (in the case of a constant domain fragment). Furthermore, immunoglobulin chains comprising a functional domain fragment may be defined by their ability to efficiently assemble into an intact antibody that comprises 2 heavy and 2 light immunoglobulin chains. Thus, in some specific embodiments, an antibody of the invention may be defined as an intact antibody or in even more specific cases an antibody may be defined as a full length antibody. Furthermore, in some aspects, an antibody for use in the invention may comprise an antibody heavy chain but no light chain polypeptide. Thus, an antibody may comprise VH, CH1 and CH2 domains. In still further aspect an antibody for use in the invention may be defined as comprising VL and Ck or CL domains.

A skilled artisan will recognize that an antibody for use in the invention may be an IgA, IgM, IgE or IgG antibody. Preferably and antibody of the invention is an IgG antibody such as an IgG1, IgG2a, IgG2b, IgG3 or IgG4 antibody. Furthermore, the antibody may be defined as a human or humanized antibody. Such an antibody comprises amino acid sequences found in endogenous human antibodies.

In some further aspects, a Gram negative bacterial cell of the invention further comprises a nucleic acid sequence encoding an antibody. The encoded antibody may be any of the antibodies defined herein. Thus, it will be understood that a nucleic acid sequence may encode an immunoglobulin (Ig) light chain, an Ig heavy chain or both. In some cases an Ig light chain and heavy chain may be encoded on separate nucleic acid molecules and may be expressed under the control of homologous or heterologous promoters. However, in some preferred aspects, the Ig light and heavy chains are encoded on the same nucleic acid molecule. For example, an Ig light and heavy chain may be expressed under the control of a single promoter in a discistronic expression cassette. In further aspects a nucleic acid of the invention comprises sequences that facilitate Ig export into the periplasmic space. Such sequences are well known in the art and may comprise a secretion signal fused to the Ig chain (U.S. Patent Publ. 20030180937 and 20030219870). Furthermore, an antibody encoding nucleic acid may comprise additional elements such as a phage packaging signal, an origin of replication or a selectable marker gene. In some preferred aspects the Ig encoding sequences are flanked by known sequences such that the Ig sequence may be amplified by PCR using primers that anneal to the known sequence. In some very specific cases a nucleic acid encoding an antibody may be the pMAZ 360-IgG vector such the one shown in FIG. 2.

In a further aspect of the invention a Gram negative bacterial cell is further defined as a population of bacterial cells wherein cells in the population comprise (a) an antibody-binding domain in the periplasm of the Gram negative bacterial cell and (b) a plurality of distinct antibodies bound to said antibody-binding domain. Furthermore, a population of bacterial cells may comprise a plurality or a library of nucleic acid molecules encoding distinct antibodies. As used herein a "distinct antibody" may be defined as an antibody that differs form another antibody by as little as one amino acid. While, in some cases distinct antibodies may comprise differences in the sequence of a light or heavy chain constant region, in preferred aspects distinct antibodies comprise amino acid differences in a heavy chain variable domain, a light chain variable domain, both the light and heavy chains or a different combination of light chain and heavy chain. Methods for making a library of distinct antibodies or nucleic acids that encode antibodies are well known in the art and exemplified herein. In certain cases, a plurality of antibodies may comprise antibodies with a plurality of light and/or heavy chain variable domains cloned from a population of B-cells or B-cell precursors. However, in other aspects, a plurality of distinct antibodies may comprise light and/or heavy chain variable domains with essentially random amino acid sequences. Thus, in some aspects, a population of gram negative bacteria according to the invention may be defined as comprising at least about $1\times10^3$, $1\times10^4$, $1\times10^5$, $1\times10^6$, $1\times10^7$, $1\times10^8$, or more distinct antibodies. In some cases a population of Gram negative bacterial cells may be produced by a method comprising the steps of: (a) preparing a plurality of nucleic acid sequences encoding a plurality of distinct antibodies; and (b) transforming a population of Gram negative bacteria with said nucleic acids wherein the Gram negative bacteria comprise an antibody-binding domain anchored to bacterial inner membrane and wherein the antibodies are expressed in the periplasm.

A variety of antibody-binding domains are known in the art and may be used in the methods and compositions of the invention. In some aspects, an antibody-binding domain binds to the constant (Fc) domain of an antibody. It will be understood that such an antibody-binding domain may have specificity for a particular type or subtype of Ig, such as IgA, IgM, IgE or IgG (e.g., IgG1, IgG2a, IgG2b, IgG3 or IgG4). Thus, in some preferred cases the antibody-binding domain may be defined as an IgG binding domain. Some antibody-binding domains for use in the invention include but are not limited to a binding domain from one of the polypeptides of Table 1. For example, an antibody-binding domain may be an antibody-binding domain encoded by a FCGR2A, FCGR2B, FCGR2c, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa or spg gene. Furthermore, an antibody-binding domain may be defined as a mammalian, bacterial or synthetic binding domain. For instance, a bacterial antibody-binding domain may be a *S. aureus* protein A or protein G domain. In certain aspects a synthetic antibody-binding domain may be the ZZ polypeptide.

In some embodiments of the invention an antibody-binding domain is anchored to the inner membrane of a Gram negative bacteria. Methods and compositions for the anchoring of polypeptides to the inner membrane of Gram negative bacterial have previously been described (U.S. Pat. No. 7,094,571 and U.S. Patent Publ. 20050260736). Thus, in some aspects, an antibody-binding domain may be fused to a polypeptide that is associated with or integrated in a bacterial inner membrane. Such a fusion protein may comprise an N terminal or C terminal fusion with an antibody-binding domain and in some cases may comprise additional linker amino acids between the membrane anchoring polypeptide and the antibody-binding domain. In certain specific cases, a membrane anchoring polypeptide may be the first six amino acids encoded by the *E. coli* NlpA gene, one or more transmembrane □-helices from an *E. coli* inner membrane protein, a gene III protein of filamentous phage or a fragment thereof, or an inner membrane lipoprotein or fragment thereof. Thus, a membrane anchoring polypeptide may be an inner membrane lipoprotein or fragment thereof such as from AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, Dsb, B, DsbD, TouB, TatC, CheY, TraB, ExbD, ExbB or Aas. In some particular aspects of the invention, a membrane anchored antibody-binding domain may be a NlpA-ZZ fusion protein such as the one exemplified in SEQ ID NO:4.

Furthermore, in certain embodiments, the invention provides a nucleic acid sequence encoding a fusion protein wherein the fusion protein comprises an inner membrane anchoring polypeptide and an antibody-binding domain. Such nucleic acid vector may comprise a number of additional sequences including, but not limited to, an origin of replication, a promoter, a phage packaging signal or a selectable marker gene. In some very particular embodiments a nucleic acid sequence of the invention may encode a NlpA-ZZ fusion protein as exemplified by the pBAD33-NlpA-ZZ vector.

In a further embodiment of the invention, there is provided a method for isolating a genetic package comprising a nucleic acid encoding a ligand-binding polypeptide comprising (i) obtaining a population of genetic packages comprising a plurality of nucleic acid sequences encoding distinct ligand-binding polypeptides wherein said packages comprise the distinct ligand-binding polypeptides in complex with a second polypeptide that binds to the ligand-binding polypeptides, (iii) contacting said population with a target ligand and (iv) selecting at least one genetic package based on binding of a distinct ligand-binding polypeptide to the ligand. In some cases, the ligand-binding polypeptide is defined as an antibody or fragment thereof (e.g., as described herein). Thus, in certain aspects, the second polypeptide that binds to the ligand-binding polypeptide may be defined as an antibody-binding polypeptide or a polypeptide comprising an antibody-binding domain.

As used herein the term genetic package refers to a structure that enables association between a ligand-binding polypeptide and a nucleic acid encoding the ligand-binding polypeptide. Thus, in some embodiments, a genetic package may be a bacterial cell or a bacteriophage as further described supra. For example, in cases wherein the genetic package is a bacterial cell, such as a Gram negative bacterial cell, the distinct ligand-binding polypeptide may be expressed in the periplasm of the Gram negative bacterial cell. For example, a population of Gram negative bacterial cells may be produced by a method comprising (a) preparing a plurality of nucleic acid sequences encoding a plurality of distinct ligand-binding polypeptides and (b) transforming a population of Gram negative bacteria with said nucleic acid sequences wherein the Gram negative bacterial cells comprise the ligand-binding polypeptides in the periplasm along with a second polypeptide that binds to the ligand-binding polypeptides. In some further aspects, the second polypeptide that binds to the ligand-binding polypeptide may be anchored to the inner membrane of the bacterial cell thereby tethering the ligand-binding polypeptide to the bacterial inner membrane. Methods for anchoring a polypeptide to or in a bacterial inner membrane are known in the art and further described herein. Thus, in certain aspects, a method of the invention may further comprise (ii) disrupting the outer membrane of a bacterial cell(s) prior to or concomitantly with contacting the bacterial cell(s) with a target ligand.

Methods for selecting a genetic package based on binding (or lack thereof) to a target ligand are further described herein in the context of bacterial cells or bacteriophages, however such methods are applicable to selection of any genetic package. For example, a ligand used for selection may be immobilized or labeled to facilitate the selection process. Selection according to the invention may comprise two or more rounds of selection wherein the sub-population of genetic packages obtained in a first round of selection is subjected to at least a second round of selection based on the binding of the distinct ligand-binding polypeptide to the target ligand. Furthermore, in some cases a selection method of the invention is further defined as a method for producing a nucleic acid sequence encoding a ligand-binding polypeptide, further comprising (v) cloning a nucleic acid sequence encoding the ligand-binding polypeptide from a selected genetic package to produce a nucleic acid sequence encoding a ligand-binding polypeptide with a specific affinity for a target ligand. Furthermore, a nucleic acid cloned from a genetic package may be expressed in a cell to produce a ligand-binding polypeptide. Thus, in some aspects, methods of the invention may be defined as methods for producing a ligand-binding polypeptide with a specific binding affinity for a target ligand.

In yet a further embodiment there is provided a method of producing a bacterial cell comprising an antibody having specific affinity for a target ligand. The foregoing method may comprise (i) obtaining a population of Gram negative bacterial cells comprising (a) an antibody-binding domain in the periplasm of the Gram negative bacterial cell and (b) a plurality of distinct antibodies bound to said antibody-binding domain as described supra. Next the antibody is (iii) contacted with a target ligand under conditions wherein the target ligand contacts the antibody, and (iv) the bacterial cell is selected based on the binding of the candidate antibody to target ligand to produce a bacterial cell(s). In some specific aspects a method of the invention may additionally comprise the step of exposing the antibody to the extra cellular environment by (ii) disrupting the outer membrane of the bacterial cell (e.g., forming a spheroplast). Thus, in certain cases the antibody binding domain may be anchored to the inner membrane of the bacterial cell as described supra. The skilled artisan will readily understand that in some cases the bacterial cell produced may be amplified by allowing the isolated cell or cell population to propagate under permissible conditions. Furthermore, a bacterial cell produced by the methods of the invention is included as part of the instant invention. Preferably, Gram negative bacterial cells for use in methods of the invention comprise an expression vector encoding a plurality of distinct antibodies. Such cells may be non-viable, but in a preferred embodiment the cells are viable and thus capable of being grown following production/isolation.

The skilled artisan will understand that methods for selecting cells based upon their interaction (binding) with a ligand are well known in the art. For example, a ligand may be immobilized on a column or bead (e.g., a magnetic bead) and the bacterial cell binding to the ligand separated by repeated washing of the bead (e.g., magnetic separation) or column. Furthermore, in some aspects a target ligand may be labeled such as with a fluorophor, a radioisotope or an enzyme. Thus, bacterial cells may, in some cases, be selected by detecting a label on a bound ligand. For example, a fluorophore may be used to select cells using fluorescence activated cell sorting (FACS). Furthermore, in some aspects, bacterial cells may be selected based on binding or lack of binding two or more ligands. For instance, bacteria may be selected that display antibodies that bind to two ligands, wherein each ligand is used to select the bacterial sequentially. Conversely, in certain aspects, bacteria may be selected that display antibodies that bind to one ligand (such as a ligand comprising a first label) but not to a second ligand (e.g., comprising a second label). The foregoing method may be used, for example, to identify antibodies that bind to a specific ligand from a family of two or more related ligands.

In further embodiments, methods for producing bacteria of the invention, may comprising at least two rounds of selection (step iv) wherein the sub-population of bacterial cells obtained in the first round of selection is subjected to at least a second round of selection based on the binding of the candidate antibody to target ligand. Furthermore in some aspects the sub-population of bacterial cells obtained in the first round of selection may be grown under permissive conditions prior to a second selection (to expand the total number of cells). Thus, in some aspects, methods of the invention may comprise 2, 3, 4, 5, 6, 7, 8, 9, 10 or more rounds of selection. Furthermore, in some aspects, a sub-population of bacterial cells obtained from each round of selection will be grown under permissive conditions before a subsequent round of selection. In some cases, selection will be performed after removing target ligand that is not bound to the antibody. Furthermore, in some cases the stringency of selection may be modified by adjusting the pH, salt concentration, or temperature of a solution comprising bacteria that display antibodies. Thus, in some aspects, it may be preferred that a bacterial cell of the invention is grown at a sub-physiological temperature such as at about 25° C.

A target ligand for use according to the invention may be any molecule that can be bound by an antibody. For example, the ligand may be a carbohydrate, a lipid moiety, a polypeptide, an organic polymer, a small molecule, or mixture thereof. In some aspects a target ligand may be a cancer-associated protein, a cell surface protein, an enzyme, a virus, a glycoprotein or a cell receptor ligand. Methods for labeling a target ligand are well know in the art and may comprise covalent or non-covalent modification a ligand (see U.S. Pat. No. 7,094,571).

In still further aspects, a method of producing a bacterial cell according to the invention may be further defined as a method of producing a nucleic acid sequence encoding an antibody having a specific affinity for a target ligand. Thus, a bacterial cell produced by the methods herein may be used to clone a nucleic acid sequence encoding the candidate antibody having a specific affinity for a target ligand. Method for isolating and amplifying such a nucleic acid from a cell for example by PCR are well known in the art and further described below. Thus, a nucleic acid sequence produced by the forgoing methods is included as part of the instant invention. Furthermore, such a sequence may be expressed in a cell to produce an antibody having a specific affinity for a target ligand. Thus, in some aspects, the invention provides a method for producing an antibody having a specific affinity for a target ligand. Furthermore, the invention includes antibodies produced by the methods of the invention. It will be understood however that the antibody variable VH and VL domains produced by such a screen may be moved into a different antibody type (e.g., comprising a different constant regions) and these antibodies are also included as part of the invention. Thus, in some aspects the invention provides an antibody VH and VL polypeptide produced by the methods of the invention. For example, in some aspects, the invention provides the VH and VL polypeptides of PA binding antibodies such as YMB2, YMD1, YMF10, YMC3 or YMH2. Furthermore the invention provides intact PA binding antibodies such as YMB2, YMD1, YMF10, YMC3 or YMH2.

In a further embodiment the invention provides a bacteriophage comprising (a) at least one coat protein fused to an antibody-binding domain wherein the antibody-binding domain is displayed on the surface of the bacteriophage particle. For example, in certain aspects a bacteriophage of the invention may be a filamentous bacteriophage such as M13. Thus, in some cases an antibody-binding domain is fused to a p3 coat protein, such as an antibody-binding domain fused to C-terminus of the p3 protein. An antibody-binding domains for display on phage particles may be any of those described herein such as the antibody-binding domain from one of the polypeptides in Table 1. In some preferred aspects, an antibody-binding domain is an Fc binding domain such as an IgG Fc binding domain. Furthermore, an antibody-binding domain may comprise a mammalian, bacterial or synthetic binding domain, such as the synthetic ZZ polypeptide. Furthermore, a nucleic acid sequence encoding a bacteriophage coat protein fused to an antibody-binding domain is also included as part of the invention. For instance, a nucleic acid sequence may comprise a infectious clone encoding a bacteriophage coat protein fused to an antibody-binding domain along with all of the other essential genes for phage production (e.g., as exemplified by the fUSE5-ZZ vector).

In still further embodiments there is provided a bacteriophage comprising (a) at least one coat protein fused to an antibody-binding domain wherein the antibody-binding domain is displayed on the surface of the bacteriophage and (b) a nucleic acid sequence encoding an antibody wherein the nucleic acid sequence is packaged or encapsulated in the bacteriophage. A nucleic acid sequence encoding an antibody may be any of those described herein, for example, a nucleic acid comprising an Ig light chain (L), an Ig heavy (H) chain or both. For instance, an Ig heavy and light chain may be encoded by a dicistronic expression vector such as pMAZ 360-IgG. Preferably, an antibody encoded by such a nucleic acid sequence is an intact antibody.

In a further embodiment there is provided a bacteriophage of the invention further comprising an antibody bound to the antibody-binding domain displayed on the surface of the bacteriophage. Preferably, a bacteriophage that displays a bound antibody comprises a nucleic acid sequence encoding an antibody packaged within the phage. Thus, in some highly preferred embodiments, the antibody bound (to the antibody-binding domain) on the surface of the bacteriophage is the same antibody encoded by the nucleic acid sequence packaged in the bacteriophage. Methods for making such a bacteriophage are exemplified herein for instance see FIG. 14. In some aspects such a method may comprise (a) obtaining a bacteriophage wherein the genome of the phage comprise sequences encoding a coat protein fused to an antibody-binding domain such that the antibody-binding domain is displayed on the surface of the bacteriophage; (b) infecting a bacterial cell comprising an antibody expressed in the periplasm and an antibody expression vector wherein the antibody expression vector comprises a phage packaging signal; and (c) allowing the phage to replicate thereby producing phage antibody complexes with an encapsulated antibody expression vector.

In still a further embodiment a bacteriophage of the invention may be further defined as a population of bacteriophages. Such a population may collectively comprise a plurality of nucleic acid sequences encoding distinct antibodies (packed within the phage). Thus, in some aspects, a population of bacteriophages according to the invention may be defined as comprising at least about $1\times10^3$, $1\times10^4$, $1\times10^5$, $1\times10^6$, $1\times10^7$, $1\times10^8$, or more distinct antibodies and/or antibody expression vectors. Preferable at least about 90%, 95%, 98%, 99%, 99.9% or more of bacteriophages in a population that comprise an antibody expression vector display the same antibody encoded by the vector on their surface.

In yet a further embodiment there is provided a method of producing a bacteriophage comprising an antibody having specific affinity for a target ligand. The foregoing method may comprise (i) obtaining a population of bacteriophages comprising (a) at least one coat protein fused to an antibody-binding domain wherein the antibody-binding domain is displayed on the surface of the bacteriophages, (b) a plurality of nucleic acid sequences encoding distinct antibodies wherein the nucleic acid sequences are packaged in the bacteriophages and the encoded antibodise are displayed on the surface of the bacteriophages. Next, (ii) the bacteriophages are contacted with a target ligand under conditions wherein the target ligand contacts the antibody, and (iii) a bacteriophage(s) is selected based on the binding of the distinct antibody to target ligand thereby producing a bacterial cell. The skilled artisan will readily understand that in some cases the bacteriophage(s) produced may be amplified by allowing the isolated phages to propagate in permissive bacterial cells. Furthermore, in some aspects the propagation of said bacteriophage(s) may be facilitated by the use of a helper phage or in bacterial cells that encode phage proteins in trans. Preferably bacteriophages for use in methods of the invention comprise an expression vector encoding a plurality of distinct antibodies wherein an expression vector encoding the displayed antibody is encapsulated within the phage. Bacteriophages produced by the methods of the invention are included as part of the instant invention.

A target ligand for use according to the invention may be any molecule that may be bound by an antibody as described herein. The skilled artisan will understand that methods for selecting bacteriophages based upon their interaction (binding) with a ligand are well known in the art. For example, a ligand may be immobilized on a column or bead (e.g., a magnetic bead) and the bacteriophages binding to the ligand separated by repeated washing of the bead (e.g., magnetic seperation) or column. Furthermore, in some aspects, bacteriophages may be selected based on binding or lack of binding two or more ligands. For instance, bacteriophages may be selected that display an antibody that binds to two ligands. Conversely, in certain aspects, bacteriophages may be selected that display antibodies that bind to one ligand but not to a second ligand. For example, bacteriophages may be selected based upon binding or lack of binding to an immobilized ligand and then subjected to a second selection for binding or lack of binding using a second immobilized ligand. The foregoing method may be used, for example, to identify antibodies that bind to a specific ligand from a family of two or more related ligands.

In further embodiments, methods for producing bacteriophages of the invention, may comprise at least two rounds of selection (step iii) wherein the sub-population of bacteriophages obtained in the first round of selection is subjected to at least a second round of selection based on the binding of the candidate antibody to target ligand. Furthermore in some aspects the sub-population of bacteriophages obtained in the first round of selection may be grown under permissive (e.g., in bacterial cells that may comprise phage trans genes or be coinfected with helper phage) conditions prior to a second selection (to expand the total number of cells). Thus, in some aspects, methods of the invention may comprise 2, 3, 4, 5, 6, 7, 8, 9, 10 or more rounds of selection. Furthermore, in some aspects, the sub-population of bacteriophages obtained for a round of selection may be grown under permissive conditions prior to subsequent round of selection. Furthermore, in some cases the stringency of selection may be modified by adjusting the pH, salt content, or shear force (flow rate) or temperature in a solution comprising bacteriophages that display antibodies.

In still further aspects, the invention concerns a method of producing a bacteriophage according to the invention, wherein the bacteriophage comprises a nucleic acid sequence encoding an antibody having a specific affinity for a target ligand. Thus, a bacteriophage produced by the methods herein may be used to clone a nucleic acid sequence encoding a distinct antibody having a specific affinity for a target ligand. Methods for isolating and amplifying such a nucleic acid from a bacteriophage or bacteriophage-infected cell (e.g., by PCR) are well known in the art. Thus, a nucleic acid sequence produced by the foregoing methods is included as part of the instant invention. Furthermore, such a nucleic acid sequence may be expressed in a cell to produce an antibody having a specific affinity for a target ligand. Thus, in some aspects, the invention provides a method for producing an antibody having a specific affinity for a target ligand. Furthermore, the invention includes antibodies produced by the methods of the invention. It will be understood however that the antibody variable VH and VL domains produced by such a screen may be moved into a different antibody type (e.g., comprising different constant regions) and these antibodies are also included as part of the invention. Thus, in some aspects the invention provides an antibody VH and VL polypeptide produced by the methods of the invention.

Embodiments discussed in the context of a methods and/or composition of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. Antibodies can be efficiently produced and purified from bacterial cells. Upon. IPTG induction E. coli JUDE1 cells efficiently produced soluble intact antibodies as shown by SDS/PAGE Western blot under non-reducing (FIG. 3A) or reducing conditions (FIG. 3B). Furthermore, IgG antibodies may be efficiently isolated by protein-A purification as shown by SDS/PAGE and staining analysis under non-reducing (FIG. 3C) or reducing conditions (FIG. 3D).

FIG. 4A-D. Binding of IgG to spheroplasts displaying the protein ZZ domain. Spheroplasts expressing either the NlpA-ZZ fusion or NlpA-80R(scFv) as a control were labeled with IgG-FITC and were analyzed by FACS. The data show that spheroplasts displaying the ZZ protein as an NlpA fusion specifically bind and become decorated with human IgG. FIG. 4A, Fluorescence histogram of spheroplasts expressing NlpA-ZZ and incubated with Human IgG-FITC; FIG. 4B, NlpA-80R+Human IgG-FITC (negative control); FIG. 4C, NlpA-ZZ+purified recombinant M18.1 IgG together with its fluorescently labeled antigen, PA-FITC; FIG. 4D, NlpA-80R+purified recombinant M18.1 IgG together with its fluorescently labeled antigen, PA-FITC.

FIG. 6A-D. Flow cytometry (FC) analysis of spheroplasts co-expressing the NlpA-ZZ and recombinant IgG in the same host cell. E. coli JUDE-1 expressing NlpA-ZZ cells were transformed with plasmids pMAZ360-M18.1 Hum-IgG (filled) and pMAZ360-26.10-IgG (clear), protein synthesis induced, the cells were converted to spheroplasts and then labeled with (FIG. 6A) PA-FITC or with (FIG. 6B) digoxigenin-BODIPY™. To confirm the specificity of IgG binding, spheroplasts were incubated with 10 fold molar excess of non-labeled PA (FIG. 6C) or BSA-digoxin (FIG. 6D) for 1 h at RT prior to incubation with the fluorescent probe. In FIG. 6C,D, filled area represents the binding without pre-incubation with unlabeled competitor while clear area represents the FC signal obtained followed the pre-incubation with the competitor.

FIG. 8A right panel, represent Western-blot analysis of 10 VH library clones selected at random. HRP-conjugated goat anti-human IgG was used to detect IgG expression. The membrane was developed using the renaissance Western blot chemiluminescence reagent (NEN, USA) according to the supplier's instructions. FIG. 8B right panel, represent the same experiment with the complete VH-VL library.

FIG. 10. Table shows the amino acid sequences of the VH and VL domains of PA binding antibodies. YMB2, VH is SEQ ID NO: 19 and VL is SEQ ID NO: 20. YMD1, VH is SEQ ID NO: 21 and VL is SEQ ID NO: 22. YMF10, VH is SEQ ID NO: 23 and VL is SEQ ID NO: 24. YMC3, VH is SEQ ID NO: 25 and VL is SEQ ID NO: 26. YMH2, VH SEQ ID NO: 27 and VL is SEQ ID NO: 26.

FIG. 12A-B. Full length IgG antibodies produced by methods of the invention are efficiently expressed. The five PA binding antibodies were expressed in bacteria, purified by protein-A chromatography and analyzed by SDS/PAGE and gel staining under non-reducing (FIG. 12A) or reducing conditions (FIG. 12B). In each case, gels were visualized by staining with GELCODE® Blue, lane 1: Clone YMB2; lane 2: Clone YMC3; lane 3: Clone YMD1; lane 4: Clone YMF10; lane 5: Clone YMH2; lane 6: standard commercial human IgG1

FIG. 13A-B. Analysis of binding affinities of the selected anti-PA IgG clones. FIG. 13A, a table of binding kinetics acquired by SPR. FIG. 13B, an example of kinetic analysis of YMF10 IgG toward PA-63 using the IgG capture method. PA-63 was injected in duplicate at concentrations of 15, 5, 1.5 and 0 nM over YMF 10 IgG captured by anti human IgG1 Fcγ fragment specific antibody. Approximately 200 RU of IgG was captured for each concentration of PA-63 analyzed, followed by a 5 minute stabilization period prior to the injection of PA-63 to determine kinetics (inset). Enlarged portion from inset displays association and dissociation of PA-63. The Y-axis was transformed to a baseline of 0 response units prior to the association phase to aid in kinetic analysis.

FIG. 15A-B. Bacteriophages displaying antibodies efficiently bind to antibody ligands and compete with free IgG. Phage particles displaying either anti-PA or anti-Digoxin antibody specifically bound to ELISA plates coated with PA (FIG. 15A) or Digoxin-BSA (FIG. 15B).

FIG. 16A-B. Bacteriophages displaying antibodies to a target ligand can be efficiently produced by methods of the invention. Mixed phages populations can be enriched for phages displaying anti-PA or anti-Digoxin antibodies by panning with the appropriate ligand as indicated. Figure indicated optical density by ELISA with plates coated with PA (FIG. 16A) or Digoxin (FIG. 16B).

FIG. 18A-B. Representative flow cytometry data. (A) Control JUDE-1 cells expressing only NlpA-ZZ proteins, double-labeled with FITC-conjugated Human Annexin V and Alexa Flour 647-Chicken anti-Human IgG Fc. (B) library cells labeled for the initial round of FACS sorting. Cells are double-labeled with FITC-conjugated Human Annexin V and Alexa Flour 647-Chicken anti-Human IgG Fc to evaluate for antigen binding and IgG expression, respectively. The thick outline indicates a typical sort gate collecting approximately the top 5% of the population displaying the highest fluorescent intensities.

DESCRIPTION OF ILLUSTRATIVE EMBODIMENTS

The present invention presents a completely novel concept that enables the screening of intact libraries of aglycosylated IgG proteins in bacteria. In all the known display technologies the protein of interest must be expressed as either a C- or N-terminal fusion to a display protein. However, this requirement imposes significant limitations that can adversely affect protein function or stability. As a result, many of the proteins that are isolated following library screening can only fold in the context of a fusion protein and cannot be expressed independently. In the present invention the IgG antibodies are initially expressed in their native form as soluble non-fusion proteins in the periplasmic space of *E. coli*. Consequently these proteins are not selected to fold or be expressed together with a fusion partner protein as is the case with earlier display technologies.

Furthermore, the methodology described herein overcomes the requirements of post-isolation manipulation related with antibody fragments prior to increasing their affinity/stability/avidity characteristics, thereby facilitating the isolation of antibody clones with a broad range of affinities to antigens of interest. Finally, in the present invention the IgG library screening vector is also utilized as the expression vector. Therefore, isolated antibodies can be readily expressed in bacteria and employed for target binding and neutralization in animal experiments directly. This feature is likely to represent important time savings for the pharmaceutical industry.

Figure 1:
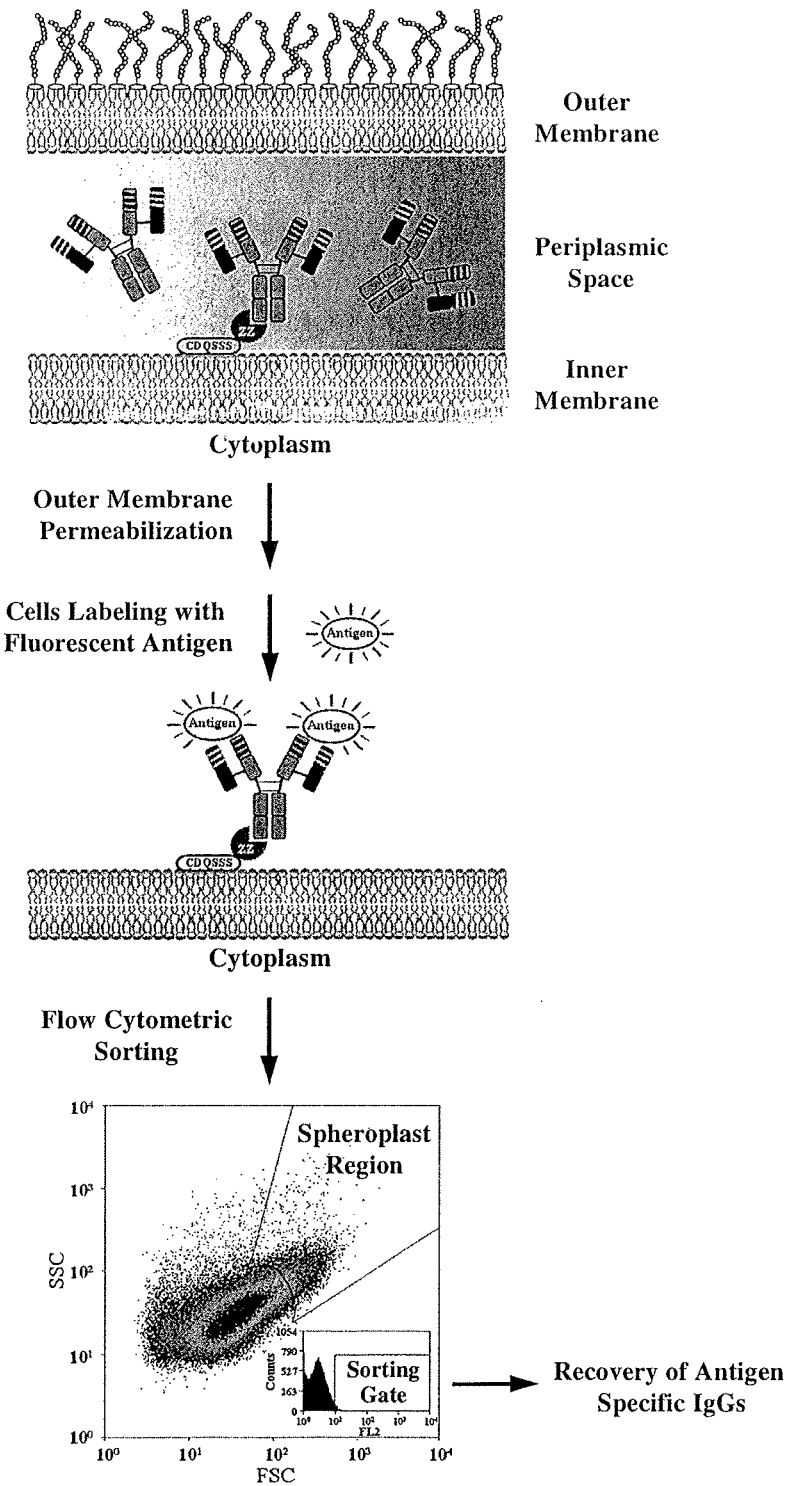
FIG. 1. A schematic diagram showing an example of an antibody screening method of the invention.
Figure 2:
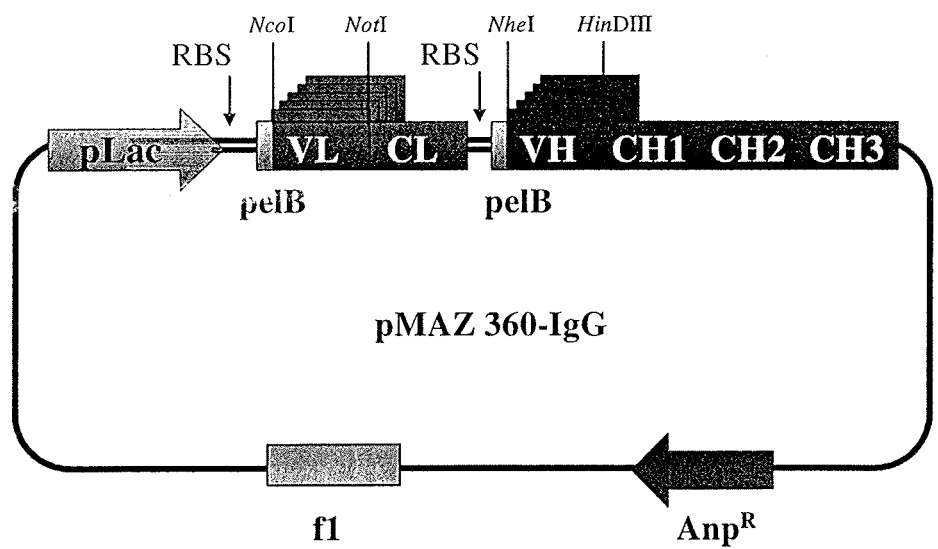
FIG. 2. A schematic diagram depicting the pMAZ 360-IgG vector.

In this invention the efficient expression of soluble fully assembled intact IgG antibody libraries in *E. coli* periplasm was carried out by constructing the pMAZ360-IgG expression vector for convenient cloning of VH and Vκ domains linked to human γ1 and κ constant domains, respectively (FIG. 2). This plasmid also contains the packaging signal of f1 that enables the packaging of the plasmid as ssDNA in the presence of helper phage. Libraries of IgG antibodies expressed in *E. coli* have now been screened using two different approaches: (i) microbial display and (ii) phage display. For both screening strategies the IgG molecules in the periplasm are captured by cells or by phage, respectively. In one embodiment the IgG is capture by cells or phage via an IgG bound protein that is anchored onto an exposed site on the cell or phage, respectively. It has also been shown however, that IgG can be captured by bacterial cells via non-specific interactions with cell wall components. Thus as a result, IgG molecules remain associated with cells and can bind antigen even when the outer membrane of the bacteria has been removed.

In one embodiment, cells expressing full length IgG in the periplasm are bound to the outer surface of the periplasmic membrane of *E. coli* or other Gram negative bacteria by means of an IgG binding protein. Many IgG binding proteins have been described in the literature and can be used for the purpose of capturing IgG (Table 1). A preferred embodiment utilizes an engineered *S. aureus* Protein A domain called the ZZ domain which binds to the Fc region of IgG. The ZZ domain or any other suitable IgG binding protein is expressed as a fusion protein that renders it anchored or strongly associated with components of the cell envelope. Anchoring or strong association with the cell envelope is such that, upon removal of the outer membrane by chemical, environmental or genetic treatment the IgG binding protein remains stably attached to the cell. As an example, a method for anchoring an IgG protein onto the cell envelope involves the fusion of said protein with the leader peptide and six amino acid N-terminal portion of an *E. coli* lipoprotein. One such sequence is (SEQ ID NO:4) derived from the *E. coli* lipoprotein NlpA. Fusions to this sequence become fatty acylated in vivo and as a result they are anchored to the membrane via the fatty acid moiety. The association of lipoproteins with the membrane is very stable and is not disrupted unless the cells are treated with strong detergents or with enzymes which result in cell lysis. While this sequence (SEQ ID NO:4) serves as an example it should be understood that any other sequence capable of providing a strong association between the cell and the IgG anchoring protein, whether covalent or non-covalent, can be used for the purposes described henceforth in this application.

In one embodiment, IgG antibodies are cloned into the pMAZ360-IgG expression vector for periplasmic expression (SEQ ID NO:1). This vector directs the expression of both the heavy and light chains form the same promoter. The heavy and light chains are secreted into the periplasm where they fold and associate to form a tertameric IgG molecule. Biochemical analysis has revealed that such molecules are completely functional and the IgG exhibits the expected binding affinity to antigen.

The IgG molecules are expressed in soluble form in the periplasm. In other words the polypeptide product is an intact IgG which does not contain any extraneous amino acids or is fused to unrelated polypeptides. In the periplasm the IgG interacts with and becomes bound to the IgG-binding protein which, as described above is in turn expressed in a form that remains associated with the cell. The next step is treatment of the cells to disrupt the outer membrane which normally serves as a barrier that restricts access of the periplasmic IgG to externally added antigens within the extracellular fluid. Disruption of the outer membrane normally results in the leakage of periplasmic proteins from the cells. However, in this case the IgG protein is bound onto the cell by the cell enveloping-attached IgG binding protein. In the preferred embodiment, the membrane anchored (NlpA-ZZ) fusion binds to the periplasmic IgG which thus remains cell-associated even after the outer membrane has been disrupted or even completely removed.

Once the outer membrane has been disrupted or removed the cells are then incubated with fluorescently labeled antigen. Cells expressing IgG antibodies that recognize the antigen become fluorescent. The fluorescent cells can be readily distinguished by fluorescence activated cell sorting (FACS). FACS is a very powerful technique for library screening purposes (Georgiou, 2000). FACS can be used to screen libraries of billions of bacterial cells with high efficiency.

A surprising finding by the inventors is that the binding of NlpA-ZZ to IgG is kinetically very stable. The ZZ domain exhibits a modest affinity for IgG in solution (Nilsson et al., 1987; Hober et al., 2006). However, the inventors found that cells expressing NlpA-ZZ bind and retain periplasmically expressed IgG antibodies for very long times. In one example the inventors found that NlpA-ZZ displaying cells that were first incubated with low concentration of fluorescently-labeled IgGs and then subjected to extensive washing steps, retained stable fluorescence signal for as long as three consecutive days. In another example the inventors determined the binding equilibrium of the NlpA-ZZ-IgG complex by means of direct cell-ELISA and found that the apparent affinity of the NlpA-ZZ moiety to the Fc of IgGs was in the sub-nanomolar range. The affinity obtained differs by approximately two orders of magnitude from the value for the interaction of the two proteins in solution. This difference arises from avidity effects from the high density of NlpA-ZZ fusion proteins expressed on the periplasmic membrane.

A second screening method for the isolation of IgG antibodies from combinatorial libraries utilizes phage display. In this embodiment the IgG molecules are expressed as soluble, proteins in *E. coli* periplasm using the expression vector pMAZ360-IgG described herein. Cells expressing IgG are simultaneously infected by FUSE5-ZZ phage particles (Yacoby et al., 2006). These phage particles allow polyvalent display of the IgG-binding protein ZZ, on all copies of the p3 minor coat protein of filamentous bacteriophage. In other words the ZZ moiety is genetically fused to the g3 gene located on the phage genome. Therefore, phage particles assembled in the *E. coli* periplasm covalently display the ZZ moiety or any other IgG binding protein on all 3-5 copies of the phage p3 coat protein. In one example, intact IgGs becomes bound p3-ZZ in the periplasm and then the p3-ZZ-IgG complex becomes incorporated into phage to form FUSE5-ZZ-IgG phage particles. In the preferred embodiment the pMAZ360-IgG expression vector performs also as phagemid. A phagemid is defined as a plasmid containing the packaging and replication origin of the filamentous bacteriophage. This latter property allows the packaging of the phagemid into a phage coat when it is present in an *E. coli* host strain infected with a filamentous phage (superinfection). In the preferred embodiment FUSE5-ZZ-IgG phage particles preferentially to package the high copy number pMAZ360-IgG phagemid over the replication-defective FUSE5-ZZ genome (Scott and Smith, 1990). Next, packaged particles produced, harboring the phagemid, display the p3-ZZ-IgG fusion protein on the surface of the particles and are secreted into the medium. Such packaged particles are able to inject their phagemid into a new host bacterium, where they can be propagated. The special property of the system lies in the fact that since the packaging takes place in individual cells usually infected by a single variant FUSE5-ZZ phage, the particles produced on propogation contain the gene encoding the particular IgG variant displayed on the particle's surface. Several cycles of affinity selection for clones exhibiting the required binding properties, e.g., binding to a particular target molecule immobilized on a surface, followed by amplification of the enriched clones leads to the isolation of antigen-specific IgG antibodies. The inventors found that the IgG captured by the ZZ-displaying phage is kinetically very stable. Competition of the bound IgGs by excess of soluble IgG competitors resulted in a very mild substitution. The inventors attribute the stable interaction of the complex ZZ-IgG to the character of the FUSE5-ZZ phage that display the ZZ moiety on all copies of the phage p3 coat protein. Hence the adjacent ZZ molecules contribute by avidity manners to capture and retain the IgG molecules in a very stable way. It should be understood that in addition to filamentous bacteriophages described herein, other bacterial phages including lytic phages such as lambda and the T series phages can be employed for the display of IgG antibodies and for the screening of IgG libraries.

I. Anchored Periplasmic Expression

In some aspects of the invention antibodies are expressed in the periplasmic space bound to antibody-binding domains that serve as anchors to the periplasmic face of the inner membrane. Such a technique may be termed "Anchored Periplasmic Expression" or "APEx".

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations ($Mg^{2+}$ and $Ca^+$) and link each other electrostatically to form a highly ordered quasi-crystalline ordered "tiled roof" on the surface (Labischinski et al., 1985). The membrane forms a very strict permeability barrier allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Nikaido and Nakae, 1979; Nikaido and Vaara, 1985). With such strict physiological regulation of access by molecules to the periplasm it may appear, at first glance, inconceivable that APEx should work unless the ligands employed are at or below the 650 Da exclusion limit or are analogues of normally permeant compounds. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, as is described herein below.

II. Permeabilization of the Outer Membrane

In one embodiment of the invention, methods are employed for increasing the permeability of the outer membrane to one or more labeled ligand. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Such a mechanism has been adopted to selectively label the periplasmic loops of a cytoplasmic membrane protein in vivo with a polymyxin B nonapeptide (Wada et al., 1999). Also, certain long chain phosphate polymers (100 Pi) appear to bypass the normal molecular sieving activity of the outer membrane altogether (Rao and Torriani, 1988).

Conditions have been identified that lead to the permeation of ligands into the periplasm without loss of viability or release of the expressed proteins from the cells, but the invention may be carried out without maintenance of the outer membrane. By anchoring candidate binding polypeptides to the outer side of the inner (cytoplasmic) membrane using fusion polypeptides, the need for maintenance of the outer membrane (as a barrier to prevent the leakage of the biding protein from the cell) to detect bound labeled ligand is removed. As a result, cells expressing binding proteins anchored to the outer (periplasmic) face of the cytoplasmic membrane can be fluorescently labeled simply by incubating with a solution of fluorescently labeled ligand in cells that either have a partially permeabilized membrane or a nearly completely removed outer membrane.

The permeability of the outer membrane of different strains of bacterial hosts can vary widely. It has been shown previously that increased permeability due to OmpF overexpression was caused by the absence of a histone like protein resulting in a decrease in the amount of a negative regulatory mRNA for OmpF translation (Painbeni et al., 1997). Also, DNA replication and chromosomal segregation is known to rely on intimate contact of the replisome with the inner membrane, which itself contacts the outer membrane at numerous points. A preferred host for library screening applications is *E. coli* ABLEC strain, which additionally has mutations that reduce plasmid copy number.

The inventors have also noticed that treatments such as hyperosmotic shock can improve labeling significantly. It is known that many agents including, calcium ions (Bukau et al., 1985) and even Tris buffer (Irvin et al., 1981) alter the permeability of the outer-membrane. Further, the inventors found that phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt and phage, a high degree of permeability was achieved (Daugherty et al., 1999). Cells comprising anchored binding polypeptides bound to fluorescently labeled ligands can then be easily isolated from cells that express binding proteins without affinity for the labeled ligand using flow cytometry or other related techniques. However, it will typically be desired to use less disruptive techniques in order to maintain the viability of cells. EDTA and Lysozyme treatments may also be useful in this regard.

III. Anchored Antibody-Binding Domains

In one embodiment of the invention, bacterial cells are provided expressing fusion polypeptides on the outer face of the inner membrane. Such a fusion polypeptide may comprise a fusion between an antibody-binding domain and a polypeptide serving as an anchor to the outer face of the inner membrane. It will be understood to those of skill in the art that additional polypeptide sequences may be added to the fusion polypeptide and not depart from the scope of the invention. One example of such a polypeptide is a linker polypeptide serving to link the anchor polypeptide and the antibody-binding domain. The general scheme behind the invention comprises the advantageous expression of a heterogeneous collection of candidate binding polypeptides.

Anchoring to the inner membrane may be achieved by use of the leader peptide and the first six amino acids of an inner membrane lipoprotein. One example of an inner membrane lipoprotein is NlpA (new lipoprotein A). The first six amino acid of NlpA can be used as an N terminal anchor for protein to be expressed to the inner membrane. NlpA was identified and characterized in *Escherichia coli* as a non-essential lipoprotein that exclusively localizes to the inner membrane (Yu, 1986; Yamaguchi, 1988).

As with all prokaryotic lipoproteins, NlpA is synthesized with a leader sequence that targets it for translocation across the inner membrane via the Sec pathway. Once the precursor protein is on the outer side of the inner membrane the cysteine residue of the mature lipoprotein forms a thioether bond with diacylglyceride. The signal peptide is then cleaved by signal peptidase II and the cysteine residue is aminoacylated (Pugsley, 1993). The resulting protein with its lipid modified cysteine on its N terminus can then either localize to the inner or outer membrane. It has been demonstrated that this localization is determined by the second amino acid residue of the mature lipoprotein (Yamaguchi, 1988). Aspartate at this position allows the protein to remain anchored via its N terminal lipid moiety to the inner membrane, whereas any other amino acid in the second position generally directs the lipoprotein to the outer membrane (Gennity and Inouye, 1992). This is accomplished by proteins LolA, LolB and the ATP dependant ABC transporter complex LolCDE (Yakushi, 2000, Masuda 2002). NlpA has aspartate as its second amino acid residue and therefore remains anchored within the inner membrane.

It has been reported that by changing amino acid 2 of lipoproteins to an Arginine (R) will target them to reside in the inner membrane (Yakushi, 1997). Therefore all lipoproteins in *E. coli* (and potentially other Gram negative bacteria) can be anchor sequences. All that is required is a signal sequence and an arginine at amino acid 2 position. This construct could be designed artificially using an artificial sec signal sequence followed by the sec cleavage region and coding for cysteine as amino acid 1 and arginine as amino acid 2 of the mature protein. Transmembrane proteins could also potentially be used as anchor sequences although this will require a larger fusion construct.

Examples of anchors that may find use with the invention include lipoproteins, Pullulanase of *K. pneumoniae*, which has the CDNSSS mature lipoprotein anchor, phage encoded celB, and *E. coli* acrE (envC). Examples of inner membrane proteins which can be used as protein anchors include: AraH, MglC, MalF, MalG, Mal C, MalD, RbsC, RbsC, ArtM, ArtQ, GlnP, ProW, HisM, HisQ, LivH, LivM, LivA, Liv E, Dpp B, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, PhnM, LacY, SecY, TolC, Dsb,B, DsbD, TonB, TatC, CheY, TraB, Exb D, ExbB and Aas. Further, a single transmembrane loop of any cytoplasmic protein can be used as a membrane anchor.

The preparation of diverse populations of fusion proteins in the context of phage display is known (see, e.g., U.S. Pat. No. 5,571,698). Thus, these techniques may be used to generate a fusion protein between a phage coat protein and an antibody-binding domain. Similar techniques may be employed with the instant invention by linking the protein of interest to an anchor for the periplasmic face of the cytoplasmic membrane instead of, for example, the amino-terminal domain of the gene III coat protein of the filamentous phage M13, or another surface-associated molecule. Such fusions can be mutated to form a library of structurally related fusion proteins that are expressed in low quantity on the periplasmic face of the cytoplasmic membrane in accordance with the invention. As such, techniques for the creation of heterogeneous collections of candidate molecules which are well known to those of skill in the art in conjunction with phage display, can be adapted for use with the invention. Those of skill in the art will recognize that such adaptations will include the use of bacterial elements for expression of fusion proteins anchored to the periplasmic face of the inner membrane, including, promoter, enhancers or leader sequences. The current invention provides the advantage relative to phage display of not requiring the use of phage or expression of molecules on the outer cell surface, which may be poorly expressed or may be deleterious to the host cell.

Antibody-binding domains are also well known in the art. Such domains may be mammalian, bacterial or synthetic domains. For instance Table 1 exemplifies some the antibody-binding polypeptides/genes that are contemplated for use according to the instant invention. However, fragments comprising only the antibody binging sequences of the polypeptide of Table 1 may also be used according to the invention.

TABLE 1

Selected Antibody-binding Polypeptides

| Protein name | Gene name | Description | Organisms | Length (aa) | Reference |
| --- | --- | --- | --- | --- | --- |
| Fc-gamma RII-a | FCGR2A | Low affinity immunoglobulin gamma Fc region | *Homo sapiens* (Human) | 317 | (Stuart et al., 1987) |

TABLE 1-continued

Selected Antibody-binding Polypeptides

| Protein name | Gene name | Description | Organisms | Length (aa) | Reference |
|---|---|---|---|---|---|
| Fc-gamma RII-a | FCGR2A | receptor II-a precursor Low affinity immunoglobulin gamma Fc region receptor II-a precursor | *Pan troglodytes* (Chimpanzee) | 316 | |
| Fc-gamma RII-b | FCGR2B | Low affinity immunoglobulin gamma Fc region receptor II-b precursor | *Homo sapiens* (Human) | 310 | (Stuart et al., 1989) |
| Fc-gamma RII-c | FCGR2C | Low affinity immunoglobulin gamma Fc region receptor II-c precursor | *Homo sapiens* (Human) | 323 | (Stuart et al., 1989) |
| Fc-gamma RIIIa | FCGR3A | Low affinity immunoglobulin gamma Fc region receptor III-A precursor | *Homo sapiens* (Human) | 254 | (Ravetch and Perussia, 1989) |
| Fc-gamma RIIIb | FCGR3B | Low affinity immunoglobulin gamma Fc region receptor III-B precursor | *Homo sapiens* (Human) | 233 | (Ravetch and Perussia, 1989) |
| Fc-gamma RI) | FCGR1A | High affinity immunoglobulin gamma Fc receptor I precursor | *Homo sapiens* (Human) | 374 | (Allen and Seed, 1988) |
| Fc-gamma RI | Fcgr1 | High affinity immunoglobulin gamma Fc receptor I precursor | *Mus musculus* (Mouse) | 404 | (Sears et al., 1990) |
| Fc-gamma RII | FCGR2 | Low affinity immunoglobulin gamma Fc region receptor II precursor | *Bos taurus* (Bovine) | 296 | (Zhang et al., 1994) |
| Fc-gamma RII | FCGR2 | Low affinity immunoglobulin gamma Fc region receptor II precursor | *Cavia porcellus* (Guinea pig) | 341 | (Tominaga et al., 1990) |
| Fc-gamma RII | Fcgr2 | Low affinity immunoglobulin gamma Fc region receptor II precursor | *Mus musculus* (Mouse) | 330 | (Ravetch et al., 1986) |
| Fc-gamma RII | Fcgr2 | Low affinity immunoglobulin gamma Fc region receptor II precursor | *Rattus norvegicus* (Rat) | 285 | (Bocek and Pecht, 1993) |
| Fc-gamma RIII | FCGR3 | Low affinity immunoglobulin gamma Fc region receptor III precursor | *Bos taurus* (Bovine) | 250 | (Collins et al., 1997) |
| Fc-gamma RIII | FCGR3 | Low affinity immunoglobulin gamma Fc region receptor III precursor | *Macaca fascicularis* (Crab eating macaque) (Cynomolgus monkey) | 254 | |
| Fc-gamma RIII | Fcgr3 | Low affinity immunoglobulin gamma Fc region receptor III precursor | *Mus musculus* (Mouse) | 261 | (Ravetch et al., 1986) |

TABLE 1-continued

Selected Antibody-binding Polypeptides

| Protein name | Gene name | Description | Organisms | Length (aa) | Reference |
|---|---|---|---|---|---|
| Fc-gamma RIII | FCGR3 | Low affinity immunoglobulin gamma Fc region receptor III precursor | *Sus scrofa* (Pig) | 257 | (Halloran et al., 1994) |
| Fc-gamma RIII | Fcgr3 | Low affinity immunoglobulin gamma Fc region receptor III precursor | *Rattus norvegicus* (Rat) | 267 | (Zeger et al., 1990) |
| FcRn | FCGRT | IgG receptor transporter FcRn large subunit p51 precursor | *Homo sapiens* (Human) | 365 | |
| FcRn | FCGRT | IgG receptor transporter FcRn large subunit p51 precursor | *Macaca fascicularis* (Crab eating macaque) (Cynomolgus monkey) | 365 | |
| FcRn | Fcgrt | IgG receptor transporter FcRn large subunit p51 precursor | *Mus musculus* (Mouse) | 365 | (Ahouse et al., 1993) |
| FcRn | Fcgrt | IgG receptor transporter FcRn large subunit p51 precursor | *Rattus norvegicus* (Rat) | 366 | (Simister and Mostov, 1989) |
| MRP protein | mrp4 | Fibrinogen- and Ig-binding protein precursor | *Streptococcus pyogenes* | 388 | (Stenberg et al., 1992) |
| Protein B | | cAMP factor | *Streptococcus agalactiae* | 226 | (Ruhlmann et al., 1988) |
| protein A | spa | Immunoglobulin G-binding protein A precursor | *Staphylococcus aureus* (strain NCTC 8325) | 516 | (Uhlen et al., 1984) |
| protein A | spa | Immunoglobulin G-binding protein A precursor | *Staphylococcus aureus* | 508 | (Shuttleworth et al., 1987) |
| protein A | spa | Immunoglobulin G-binding protein A precursor | *Staphylococcus aureus* (strain Mu50/ATCC 700699) | 450 | (Kuroda et al., 2001) |
| protein A | spa | Immunoglobulin G-binding protein A precursor | *Staphylococcus aureus* (strain N315) | 450 | (Kuroda et al., 2001) |
| protein G | spg | Immunoglobulin G-binding protein G precursor | *Streptococcus* sp. group G | 448 | (Fahnestock et al., 1986) |
| protein G | spg | Immunoglobulin G-binding protein G precursor | *Streptococcus* sp. group G | 593 | (Olsson et al., 1987) |
| protein H | | Immunoglobulin G-binding protein H precursor | *Streptococcus pyogenes* serotype M1 | 376 | (Gomi et al., 1990) |
| Protein sbi | sbi | Immunoglobulin G-binding protein sbi precursor | *Staphylococcus aureus* (strain NCTC 8325-4) | 436 | (Zhang et al., 1998) |
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |

Methods for creation of fusion proteins are well known to those of skill in the art (see, for example, U.S. Pat. No. 5,780,279). One means for doing so comprises constructing a gene fusion between a candidate binding polypeptide and an anchor sequence and mutating the binding protein encoding nucleic acid at one or more codons, thereby generating a family of mutants. The mutated fusion proteins can then be expressed in large populations of bacteria. Those bacteria in which a target ligand binds, can then be isolated and the corresponding nucleic acid encoding the binding protein can be cloned.

IV. Antibody Libraries

Examples of techniques that could be employed in conjunction with the invention for creation of diverse antibody-binding domain and/or antibodies include the techniques for expression of immunoglobulin heavy chain libraries described in U.S. Pat. No. 5,824,520. In this technique, a single chain antibody library is generated by creating highly divergent, synthetic hypervariable regions. Similar techniques for antibody display are given by U.S. Pat. No. 5,922,545. These techniques may be adapted to generate intact or full length antibody libraries as described herein.

In certain embodiments, libraries of semi-synthetic antibodies can be prepared. Semi-synthetic antibodies contain a fully or partially randomized stretch of amino acid within the variable domain of an immunoglobulin heavy chain, light chain, or both. A polypeptide or polypeptide sequence is "randomized" when it has one or more regions, each containing a fully or partially random amino acid sequence. In a fully randomized sequence, all 20 of the naturally occurring, genetically encoded amino acids can be present at each amino acid position in the random sequence. In a partially randomized sequence, less than 20 of the naturally occurring, genetically encoded amino acids are present at each amino acid position in the random sequence.

The variable domains of both immunoglobulin heavy and light chains contain three hypervariable regions called complementarity determining regions ("CDRs") which alternate with four conserved regions called framework regions ("FRs"). The different regions are arranged from N- to C-terminus as FR1-CDR1-FR2-CDR2-FR3-CDR3-FR4. Hypervariable and framework regions can be defined by reference to a conventional numbering scheme (the Kabat numbering scheme) and standard texts describing antibody structure, e.g., Kabat et al "Sequences of Proteins of Immunological Interest: 5th Edition" U.S. Department of Health and Human Services, U.S. Government Printing Office (1991). In certain embodiments of the present invention, the CDR3 region of an immunoglobulin heavy or light chain, or both, is fully or partially randomized To produce randomized antibodies, double stranded nucleic acid molecules encoding randomized nucleotide sequences can be prepared and cloned in expression vectors. A nucleic acid, such as an oligonucleotide or polynucleotide, or a nucleic acid sequence is randomized when it has one or more regions, each containing a fully or partially random nucleic acid sequence. A fully randomized nucleic acid sequence is a sequence in which each base (A, T, C, and G) is present at each position in the random sequence. In a partially randomized sequence, less than four of the bases are present at each position in the random sequence. Standard symbols used to designate randomized bases in nucleic acid sequences are: R=A,G; Y=C,T; M=A,C; K=G,T; W=A,T; S=C,G; B=C, G,T; D=A,G,T; H=A,C,T; V=A,C,G; and N=A,C,G,T.

In essence, a randomized oligonucleotide, polynucleotide or polypeptide is a set of oligonucleotides, polynucleotides or polypeptides, respectively, each member of which corresponding to one of the sequences making up the randomized region. Thus, a randomized antibody is represented by a collection of antibodies, each comprising one of the amino acid sequences of the randomized region.

V. Screening Distinct Antibodies

The present invention provides methods for identifying molecules capable of binding a target ligand. The binding polypeptides screened may comprise large libraries of diverse candidate substances, or, alternatively, may comprise particular classes of compounds selected with an eye towards structural attributes that are believed to make them more likely to bind the target ligand. In one embodiment of the invention, the candidate binding protein is an antibody, or a fragment or portion thereof. In other embodiments of the invention, the candidate molecule may be another binding protein.

To identify a candidate molecule capable of binding a target ligand in accordance with the invention, one may carry out the steps of: providing a population of Gram negative bacterial cells or phages that display a distinct antibody; admixing the bacteria or phages and at least a first labeled or immobilized target ligand capable of contacting the antibody and identifying at least a first bacterium or phage expressing a molecule capable of binding the target ligand.

In some aspects of the aforementioned method, the binding between antibody and a labeled ligand will prevent diffusing out of a bacterial cell. In this way, molecules of the labeled ligand can be retained in the periplasm of the bacterium comprising a permeablized outer membrane. Alternatively, the periplasm can be removed, whereby the displayed antibody will cause retention of the bound candidate molecule. The labeling may then be used to isolate the cell expressing a binding polypeptide capable of binding the target ligand, and in this way, the gene encoding the binding polypeptide isolated. The molecule capable of binding the target ligand may then be produced in large quantities using in vivo or ex vivo expression methods, and then used for any desired application, for example, for diagnostic or therapeutic applications, as described below.

Binding polypeptides or antibodies isolated in accordance with the invention also may help ascertain the structure of a target ligand. In principle, this approach yields a pharmacophore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacophore. Anti-idiotypes may be generated using the methods described herein for producing antibodies, using an antibody as the antigen. On the other hand, one may simply acquire, from various commercial sources, small molecule libraries that are believed to meet the basic criteria for binding the target ligand. Such libraries could be provided by way of nucleic acids encoding the small molecules or bacteria expressing the molecules.

A. Cloning of Binding Protein Coding Sequences

The binding affinity of an antibody or other binding protein can, for example, be determined by the Scatchard analysis of Munson & Pollard (1980) or by Surface Plasmon Resonance Spectrometry using commercially available instruments and microfluidic chips. After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein).

Once isolated, the antibody or binding protein DNA may be placed into expression vectors, which can then be transfected into host cells such as simian COS cells, Chinese hamster ovary (CHO) cells, or myeloma cells that do not otherwise produce immunoglobulin protein, to obtain the synthesis of binding protein in the recombinant host cells. The DNA also may be modified, for example, by substituting the coding sequence for human heavy and light chain constant domains in place of the homologous murine sequences (Morrison, et al., 1984), or by covalently joining to the immunoglobulin coding sequence all or part of the coding sequence for a non-immunoglobulin polypeptide. In that manner, "chimeric" or "hybrid" binding proteins are prepared to have the desired binding specificity.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for the target ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

B. Maximization of Protein Affinity for Ligands

In a natural immune response, antibody genes accumulate mutations at a high rate (somatic hypermutation). Some of the changes introduced will confer higher affinity, and B cells displaying high-affinity surface immunoglobulin. This natural process can be mimicked by employing the technique known as "chain shuffling" (Marks et al., 1992). In this method, the affinity of "primary" human antibodies obtained in accordance with the invention could be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large antibody repertoires was described by Waterhouse et al., (1993), and the isolation of a high affinity human antibody directly from such large phage library was reported by Griffith et al., (1994). Gene shuffling also can be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by the phage display technique is replaced with a repertoire of human V domain genes, creating rodent-human chimeras. Selection of the antigen results in isolation of human variable regions capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

C. Labeled Ligands

In one embodiment of the invention, an antibody or binding protein is isolated which has affinity for a labeled ligand. By permeabilization and/or removal of the periplasmic membrane of a Gram negative bacterium in accordance with the invention, labeled ligands of potentially any size could be screened. In the absence of removal of the periplasmic membrane, it will typically be preferable that the labeled ligand is less that 50,000 Da in size in order to allow efficient diffusion of the ligand across the bacterial periplasmic membrane.

As indicated above, it will typically be desired in accordance with the invention to provide a ligand which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Magnetic screening techniques are well known to those of skill in the art (see, for example, U.S. Pat. No. 4,988,618, U.S. Pat. No. 5,567,326 and U.S. Pat. No. 5,779,907). Examples of paramagnetic ions that could be used as labels in accordance with such techniques include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of ligand conjugate contemplated in the present invention are those where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, ligands can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). Ligands also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

The ability to specifically label periplasmic expressed proteins with appropriate fluorescent ligands also has applications other than library screening. Specifically labeling with fluorescent ligands and flow cytometry can be used for monitoring production during protein manufacturing. While flow cytometry has been used previously for the analysis of bacterial cells, it has not been used for the specific labeling and quantitation of periplasmic proteins. However, a large number of commercially important proteins including IGF-1, several interleukins, enzymes such as urokinase-type plasminogen activator, antibody fragments, inhibitors (e.g., bovine pancreatic trypsin inhibitor) are expressed in recombinant bacteria in a form secreted into the periplasmic space. The level of production of such proteins within each cell in a culture can be monitored by utilizing an appropriate fluorescent ligand and flow cytometric analysis, according to the techniques taught by the present invention.

Generally, monitoring protein expression requires cell lysis and detection of the protein by immunological techniques or following chromatographic separation. However, ELISA or western blot analysis is time-consuming and does not provide information on the distribution of expression among a cell population and cannot be used for on-line monitoring (Thorstenson et al., 1997; Berrier et al., 2000). In contrast, FACS labeling is rapid and simple and can well be applied to online monitoring of industrial size fermentations of recombinant proteins expressed in Gram-negative bacteria. Similarly, the invention could be used to monitor the production of a particular byproduct of a biological reaction. This also could be used to measure the relative concentration or specific activity of an enzyme expressed in vivo in a bacterium or provided ex vivo.

Once a ligand-binding protein, such as an antibody, has been isolated in accordance with the invention, it may be desired to link the molecule to at least one agent to form a conjugate to enhance the utility of that molecule. For example, in order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Techniques for labeling such a molecule are known to those of skill in the art and have been described herein above.

Labeled binding proteins such as antibodies which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; and De Jager R et al., 1993, each incorporated herein by reference. Such techniques include binding assays such as the various types of enzyme linked immunosorbent assays (ELISAs) and/or radioimmunoassays (RIA) known in the art.

The ligand-binding molecules, including antibodies, prepared in accordance with the present invention may also, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

VI. Automated Screening with Flow Cytometry

In one embodiment of the invention, fluorescence activated cell sorting (FACS) screening or other automated flow cytometric techniques may be used for the efficient isolation of a bacterial cell comprising a labeled ligand bound to a candidate molecule and linked to the outer face of the cytoplasmic membrane of the bacteria. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MOFLO™ from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

VII. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences of fusion polypeptides comprising a candidate antibody or other binding protein having affinity for a selected ligand and the expression of such molecules on the cytoplasmic membrane of the Gram negative bacteria. In other embodiments of the invention, expression of such coding sequences may be carried, for example, in eukaryotic host cells for the preparation of isolated binding proteins having specificity for the target ligand. The isolated protein could then be used in one or more therapeutic or diagnostic applications.

A. Methods of Nucleic Acid Delivery

Certain aspects of the invention may comprise delivery of nucleic acids to target cells. For example, bacterial host cells may be transformed with nucleic acids encoding candidate molecules potentially capable binding a target ligand, In particular embodiments of the invention, it may be desired to target the expression to the cytoplasmic membrane of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

1. Electroporation

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectindegrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

2. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

B. Vectors

Vectors may find use with the current invention, for example, in the transformation of a Gram negative bacterium with a nucleic acid sequence encoding a candidate polypeptide which one wishes to screen for ability to bind a target ligand. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example of such promoter that may be used with the invention is the *E. coli* arabinose promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

E. Candidate Binding Proteins and Antibodies

In certain aspects of the invention, antibodies are expressed on the cytoplasmic or in the periplasmic space membrane of a host bacterial cell. By expression of a heterogeneous population of such antibodies, those antibodies having a high affinity for a target ligand may be identified. The identified antibodies may then be used in various diagnostic or therapeutic applications, as described herein.

As used herein, the term "antibody" is intended to refer broadly to any immunologic binding agent such as IgG, IgM, IgA, IgD and IgE. The term "antibody" is also used to refer to any antibody-like molecule that has an antigen binding region, and includes antibody fragments such as Fab', Fab, $F(ab')_2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference). However, in preferred aspects, an antibody for use in the invention is an intact antibody comprising a heavy chain constant domain.

Once an antibody having affinity for a target ligand is identified, the antibody or ligand-binding polypeptide may be purified, if desired, using filtration, centrifugation and various chromatographic methods such as HPLC or affinity chromatography. Fragments of such polypeptides, including antibodies, can be obtained from the antibodies so produced by methods which include digestion with enzymes, such as pepsin or papain, and/or by cleavage of disulfide bonds by chemical reduction. Alternatively, antibody or other polypeptides, including protein fragments, encompassed by the present invention can be synthesized using an automated peptide synthesizer.

A molecular cloning approach comprises one suitable method for the generation of a heterogeneous population of candidate antibodies that may then be screened in accordance with the invention for affinity to target ligands. In one embodiment of the invention, combinatorial immunoglobulin phagemid can be prepared from RNA isolated from the spleen of an animal. By immunizing an animal with the ligand to be screened, the assay may be targeted to the particular antigen. The advantages of this approach over conventional techniques are that approximately $10^4$ times as many antibodies can be produced and screened in a single round, and that new specificities are generated by H and L chain combination which further increases the chance of finding appropriate antibodies.

VIII. Manipulation and Detection of Nucleic Acids

In certain embodiments of the invention, it may be desired to employ one or more techniques for the manipulation, isolation and/or detection of nucleic acids. Such techniques may include, for example, the preparation of vectors for transformation of host cells as well as methods for cloning selected nucleic acid segments from a transgenic cell. Methodology for carrying out such manipulations will be well known to those of skill in the art in light of the instant disclosure.

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids comprising one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Vectors for Dicistronic Expression of Intact IgG Antibodies in *E. coli* Periplasm and for Fluorescence Detection of NlpA-ZZ-IgG Displaying Cells The pMAZ360-IgG expression vector was designed to allow efficient expression of soluble full-assembled IgG antibodies in *E. coli* periplasm. The plasmid facilitates convenient cloning of VH and Vκ genes linked to human γ1 and κ constant domains, respectively as a dicistronic operon downstream to a lac promoter (FIG. 2). Briefly, the first cistron comprised of the light chain fused to a pelB leader sequence for secretion into the periplasm. Two stop codons were engineered at the end of the light chain cistron, followed by approximately 20 nucleotides before the Shine-Dalgarno sequence of the next cistron. A second pelB leader sequence was incorporated to the N-terminus of the heavy chain for efficient secretion into the periplasm. VH domains are introduced into the vector via NheI/HindIII restriction sites, whereas, VL domains are cloned as NcoI/NotI restriction fragments. The plasmid contains an ampicillin selectable marker and the packaging signal of f1 that enables the packaging of the plasmid as ssDNA in the presence of a helper phage.

The variable domains of a humanized derivative of the anti-*Bacillus anthracis* Protective Antigen of M18.1 Hum (Harvey et al., 2004) were introduced into pMAZ360-IgG expression vector to construct plasmid pMAZ360-M18.1-Hum-IgG (SEQ ID NO:1). In the same way the murine anti-Digoxin 26.10 (Chen et al., 1999) variable domains were cloned into pMAZ360-IgG to construct plasmid pMAZ360-26.10-IgG (SEQ ID NO:2).

For expression of intact IgG antibodies in the bacterial periplasm, *E. coli* JUDE1 cells transformed with expression plasmids pMAZ360-M18.1-Hum-IgG or pMAZ360-26.10-IgG were grown in a 200 ml scale. Upon induction with IPTG, soluble cell extract fractions of cells expressing the M18.1 Hum IgG were tested for full-length IgG production by Western-blot analysis under non-reducing conditions (FIG. 3A) and reducing conditions (FIG. 3B). Soluble IgG antibodies were purified by passing the soluble cell extracts on a protein A column. Under these conditions, M18.1 Hum IgG and 26.10 IgG were purified to near-homogeneity as based upon separation on 12%/SDS-PAGE under non-reducing conditions (FIG. 3C) and reducing conditions (FIG. 3D) at yields of about 1 mg/l of cells. As seen by the Western-blot analysis (FIG. 3A) a low degree of intermediate partially assembled IgG products is also obtained. However the majority of the heavy and light molecules are presented as tetrameric full-assembled intact IgG.

For capturing soluble expressed intact IgGs via the ZZ moiety for display onto the periplasmic face of the inner-membrane plasmid pBAD33-NlpA-ZZ was constructed (SEQ ID NO:3). In this plasmid the ZZ gene was inserted in frame to the C-terminus of a sequence encoding the leader peptide and first six amino acids of the mature NlpA (containing the putative fatty acylation and inner membrane targeting sites). NlpA-ZZ fusion proteins expressed under the PBAD promoter are secreted to the periplasmic compartment and become tethered to the inner-membrane.

Figure 4A:
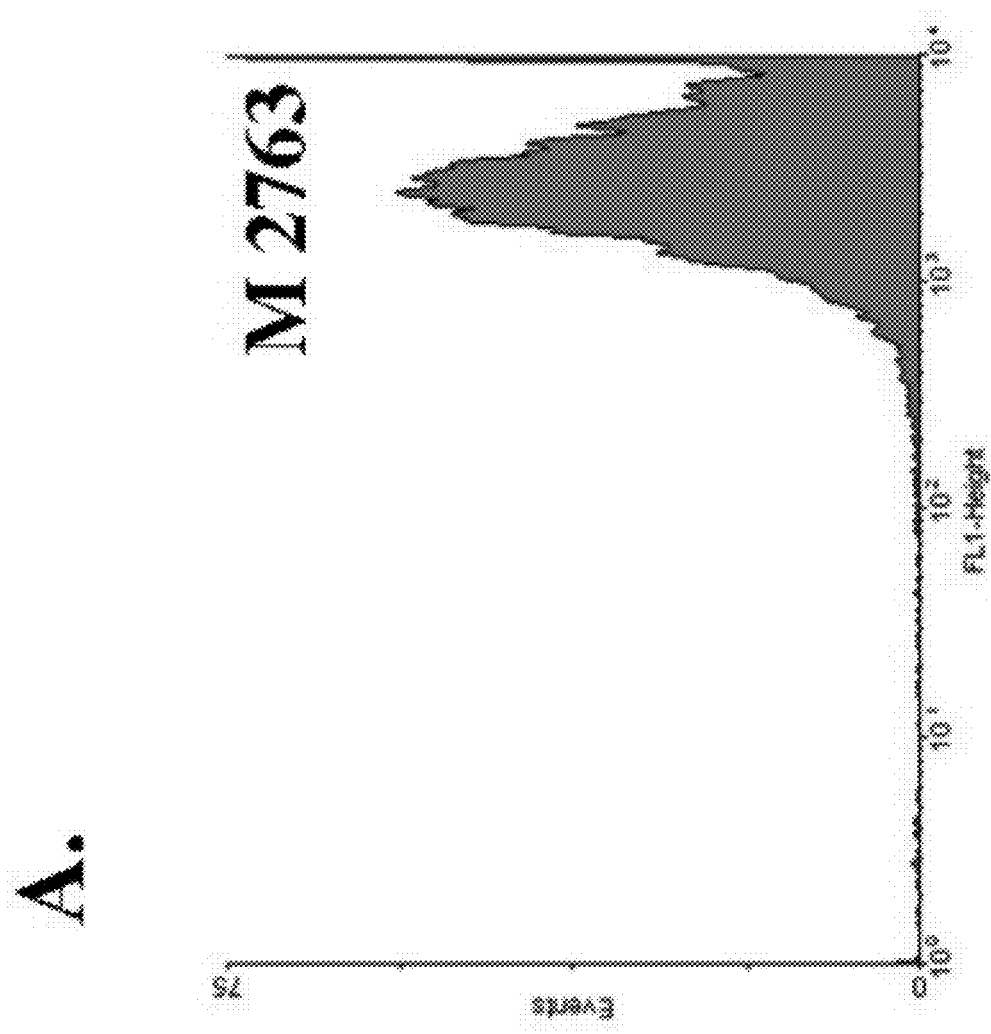
Figure 4C:
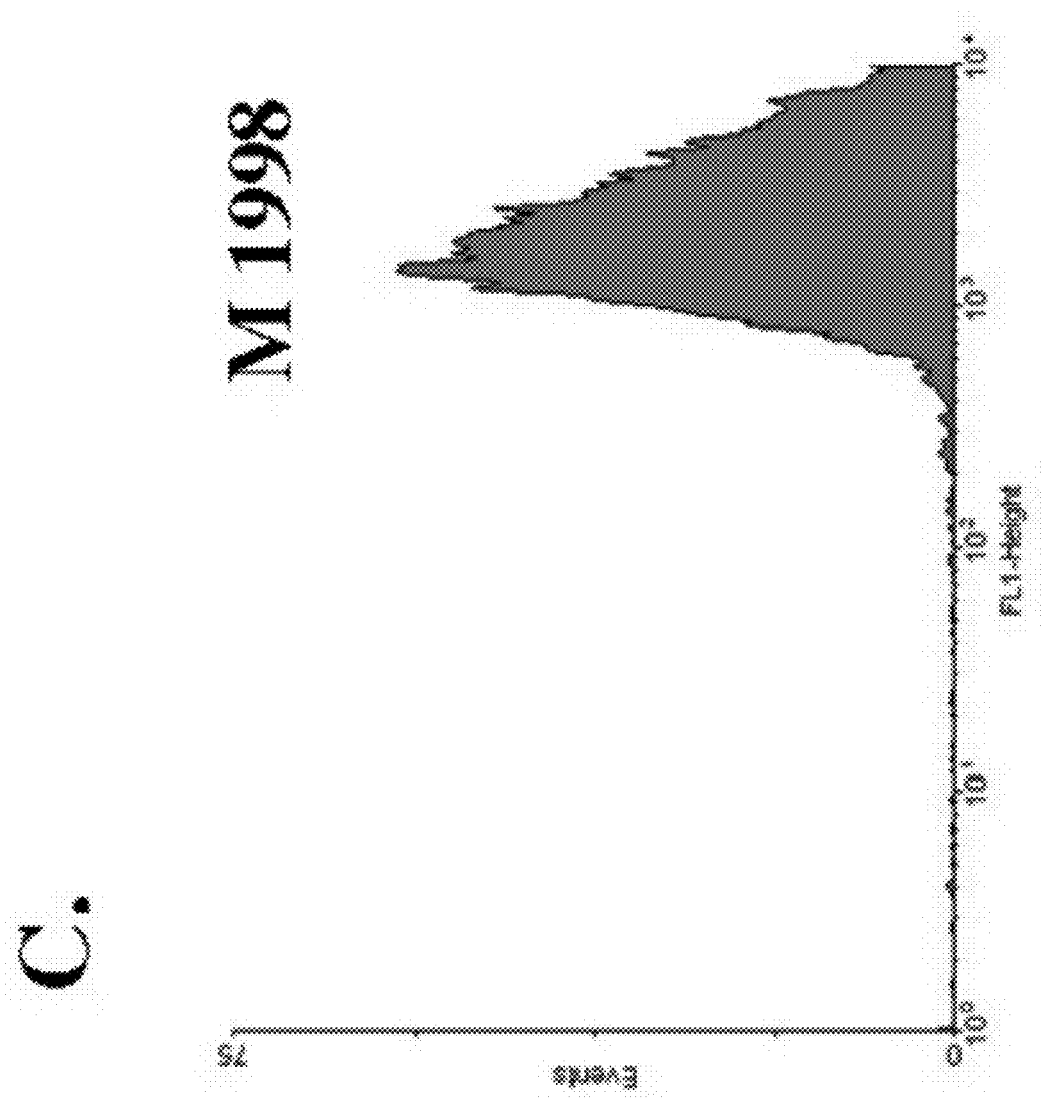
Figure 4D:
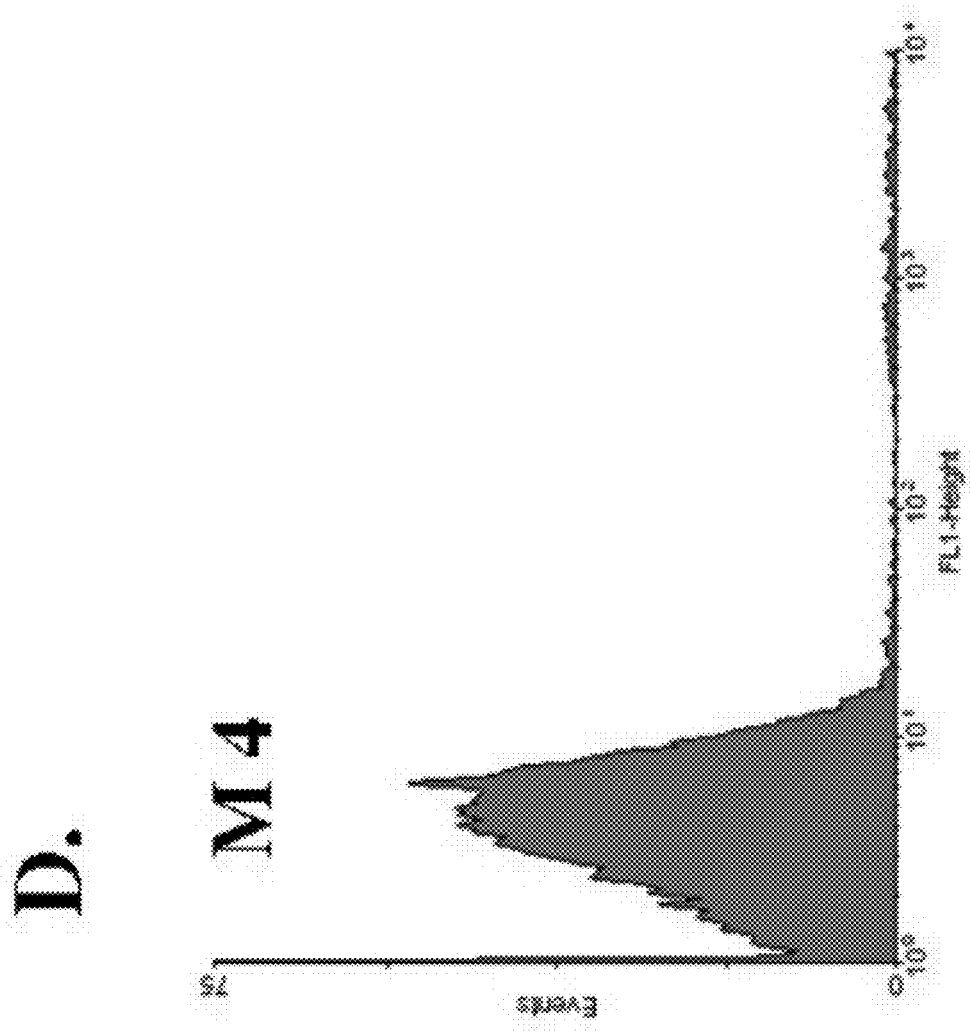

NlpA-ZZ displaying spheroplasts were initially evaluated for their ability to capture externally added IgG antibodies added to the extracellular fluid. Upon induction of protein synthesis with arabinose, the *E. coli* outer membrane was disrupted by incubation in Tris-EDTA and lysozyme and permeabilized spheroplasts were tested for capturing fluorescently-labeled commercial Human IgG antibodies (FIG. 4A) or bacterially expressed M18.1 Hum IgG antibodies followed by incubation with FITC-conjugated PA (FIG. 4C). The cell fluorescence was determined by means of flow cytometry (FC).

Spheroplasted cells displaying the NlpA-ZZ fusion were able to capture the fluorescently labeled Human IgG antibodies. In control experiments no labeling was detected with spheroplasts expressing an NlpA fusion to a protein (scFv) that does not bind IgG (FIG. 4B,D). Whole cell ELISA indicated that approximately, 7500 NlpA-ZZ molecules are presented on each spheroplasted cell. Determination of the equilibrium dissociation constant ($K_D$) of the complex NlpA-ZZ-IgG by half-maximal binding revealed a $K_D$ value of less then 100 pM. The $K_D$ values obtained in whole cells are much higher than the equilibrium dissociation constant for the ZZ:IgG complex measured in solution (estimated as 10 nM, Nilsson et al., 1987; Hober et al., 2006). This difference in affinity is most likely a consequence of avidity effects obtained from the high density of NlpA-ZZ fusion proteins expressed on the periplasmic membrane.

Figure 5:
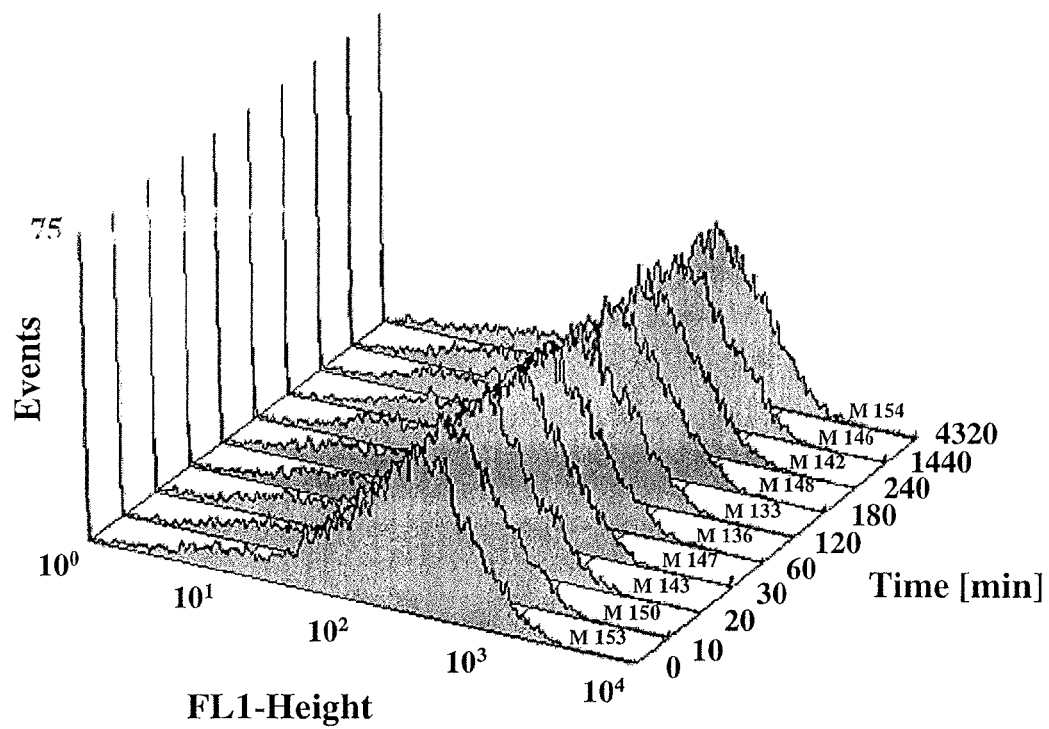
FIG. 5. IgG antibodies remain stably associated with ZZ. Fluorescently labeled IgG was incubated with spheroplasts comprising membrane anchored ZZ. Cell fluorescence was determined at various time intervals by FACS. Y-axis indicated number of events (cells), x-axis indicated fluorescence intensity and z-axis indicates incubation time.

The retention and stability of the NlpA-ZZ-IgG complexes on the surface of spheroplasts was determined by monitoring the cells fluorescence (arising from the fluorescently labeled IgG) as a function of time, by flow cytometry (FIG. 5). No reduction in fluorescence signal was obtained even after three days. Evidently, the high density of NlpA-ZZ molecules anchored on the periplasmic membrane results in high avidity binding of IgG molecules which in turn gives rise to a very high apparent binding constant for IgG on the spheroplasts.

Example 2

Expression of IgG in Bacteria

A. Construction of Bacterial pMAZ360-IgG Expression Vector and Cloning of Immunoglobulin Genes to be Expressed as Intact IgG in *E. coli* Periplasm.

Plasmid pMAZ360-IgG was designed for the efficient expression of soluble fully-assembled IgG antibodies in *E. coli* periplasm as a dicistronic operon transcribed from a single promoter. Initially, a HindIII site on pMoPac 16 (Hayhurst et al., 2003) was removed by site directed mutagenesis (Strategene, USA. QUICKCHANGE® Mutaganesis Kit) using primers HindIII-Mut-FOR and HindIII-Mut-REV (all PCR primers are listed in Table 2). Vectors containing the constant regions for the light and heavy chains of human IgG1 were kindly provided by Nancy Green (Albert Einstein College of Medicine, USA). The heavy chain gene of M18.1 Hum IgG was constructed by PCR. First, the human gamma 1 constant heavy chain region (CH1-CH3) was recovered by PCR using primers CH1-FOR and CH3-AscI-REV. In a second PCR reaction the VH region of M18.1 Hum was amplified using primers M18.1-VH-NheI-FOR and M18.1-VH-HindIII-REV. The former introduces a Shine Dalgarno and a silent mutation in the pelB leader incorporating a unique NheI site while the later introduces a sequence corresponding to the HindIII site on the N-terminus of the CH1 domain. The two PCR products were combined by an overlap extension PCR using primers M18.1-VH-NheI-FOR and CH3-AscI-REV to give the complete heavy chain gene. The light chain gene of M18.1 Hum IgG was also constructed by PCR. The human Kappa light chain was amplified using primers CK-FOR and CK-Stop-REV (Table 2). The later introduces two stops codons and overlap with the Shine Dalgarno and a pelB leader sequence on the N-terminus of the VH domain. The VL region of M18.1 Hum was amplified in a second PCR reaction using primers M18.1-VL-NcoI-FOR and M18.1-VL-Not-REV. The later incorporated a NotI site that corresponds with the NotI sequence on the N-terminus of the Ck domain. The two PCR products were combined by an overlap extension PCR using primers M18.1-VL-NcoI-FOR and CK-Stop-REV to give the complete light chain gene. Finally, the heavy and light gene templates were assembled to give a complete bicistronic IgG gene by overlap extension PCR using primers M18.1-VL-NcoI-FOR and CH3-AscI-REV. The resulting PCR product of ~2 kb was purified and digested with restriction enzymes NcoI and AscI and cloned into the pMoPac 16 vector recovered following digestion with the same enzymes. The resulting vector was named pMAZ360-M18.1-Hum-IgG. VH and VL domains are introduced to the pMAZ360-IgG vector as NheI/HindIII and NcoI/NotI restriction fragments, respectively. The VH and VL variable domains of the murine anti-Digoxin 26.10 (Chen et al., 1999) were introduced into plasmid pMAZ360-IgG as NheI/HindIII and SfiI/NotI restriction fragments, respectively. The resulting plasmid was named pMAZ360-26.10-IgG.

B. Expression and Purification of Intact IgGs in Bacterial Periplasm

For expression of soluble intact IgG, *E. coli* JUDE1 cells transformed with pMAZ360-M18.1 Hum-IgG and pMAZ360-26.10-IgG expression plasmids was inoculated overnight (ON) at 30° C. in Luria broth (LB) medium supplemented with 100 µg/ml ampicillin and 2% (w/v) glucose. The following day the cultures were diluted into 200 ml of Terrific broth (TB) medium supplemented with 100 µg/ml ampicillin and 2% (w/v) glucose to give a starting $A_{600}$ of 0.2 and grown at 30° C. When the cultures reached an $A_{600}$ of 1.0, the cells were pelleted for 15 min at 6000 rpm and resuspended in TB medium supplemented with 100 µg/ml ampicillin and 1 mM isopropyl-1-thio-D-galactopyranoside (IPTG). Cells were induced over night at 25° C. for expression of IgG. The following day cells were harvested and pelleted for 15 min at 6000 rpm. Cell extracts were prepared by resuspension of the pellet in 20 ml of BUGBUSTER™ HT Protein Extraction Reagent (NOVAGENE™, USA). Followed rotation head-over-head for two hours at room temperature (RT) the extracts were clarified by centrifugation at 12,000 rpm at 4° C. The clarified sample was diluted 1:1 with loading buffer (20 mM $Na_2HPO_4$, 2 Mm $NaH_2PO_4$) and loaded onto a 1-ml protein-A column at a flow rate of 0.5 ml/min. The column was extensively washed with loading buffer at a flow rate of 2 ml/min. Bound antibody was eluted at a flow rate of 0.5 ml/min with 0.1 M of citric acid (pH 3) and neutralized with 1 M Tris/HCl (pH 9). Protein-containing fractions were combined, dialyzed against 5 liters of PBS (16 h, 4□C), sterile filtered and stored at 4° C. Purified IgG antibodies were analyzed by 12%/SDS polyacrylamide gel electrophoresis under reducing and non-reducing conditions and stained with GELCODE® Blue (Pierce, USA). For Western blot, soluble cell extracts were separated by 12%/SDS polyacrylamide gel electrophoresis under reducing and non-reducing conditions and electro-transferred onto nitrocellulose membrane. Heavy and light IgG chains were detected with HRP-conjugated goat anti human antibodies (Jackson ImmunoResearch Laboratories, USA). The membrane was developed using the RENAISSANCE® Western blot Chemiluminescence Reagent (NEN, USA) according to the supplier's instructions.

C. Construction of Plasmid pBAD33-NlpA-ZZ

Plasmid pBAD33-NlpA-ZZ for expression of NlpA-ZZ fusion proteins was constructed as follows: A DNA fragment carrying the leader peptide and first six amino acids of the mature NlpA gene in frame with a scFv sequence was obtained as a XbaI/HindIII fragment from plasmid pAPEx 1 (Harvey et al., 2004) and introduced into plasmid pBAD33 that was linearized by the same enzymes. The resulting plasmid was named pBAD33-NlpA-scFv. Next, the ZZ gene flanked by NcoI and NotI sites was recovered from plasmid pET22-NN-ZZ-PE38 and inserted as NcoI/NotI fragment into plasmid pBAD33-NlpA-scFv digested with the same enzymes to generate the final pBAD33-NlpA-ZZ.

D. Flow Cytometry Analysis

Evaluation of the ability of NlpA-ZZ displaying spheroplasts to capture full length IgG antibodies added to the supernatant was performed as followed: *E. coli* JUDE-1 transformed with the pBAD33-NlpA-ZZ plasmid were inoculated in TB medium supplemented with 30 μg/ml chloramphenicol and 2% (w/v) glucose and grown at 30° C. When the cultures reached to an $A_{600}$ of 1.0, the cells were pelleted for 5 min at 4500 rpm and resuspended in TB medium supplemented with 30 μg/ml chloramphenicol and 0.2% arabinose. The cells were grown for 4 more hours at 25° C. Followed induction, spheroplasts were prepared by permeabilization of the cellular outer membrane. Cells equivalent to ~1 ml of $A_{600}$=5 were pelleted for 5 min at 8000 rpm in an microfuge and resuspended in 350 μl of ice-cold solution of 0.75 M sucrose/0.1 M Tris-HCl, pH=8. Next, 700 μl of ice-cold 1 mM EDTA were added gently followed by addition of 100 μg/ml hen egg lysozyme. The suspension was incubated at RT for 20 min, followed by addition of 50 μl of 0.5 M $MgCl_2$ and incubation on ice for additional 15 min. The suspension was pelleted by centrifugation for 10 min at 10,000 rpm at 4° C. and the resulting spheroplasts were resuspended in 1 ml of PBS. For labeling, cells equivalent to ~1 ml of $A_{600}$=1 were incubated with 50 nM of FITC-conjugated Human IgG antibodies or 100 nM of bacterially expressed M18.1 Hum IgG antibodies followed by incubation with 50 mM FITC-conjugated PA. For studying the NlpA-ZZ-IgG complex stability, labeling was done 5 nM of FITC-conjugated Human IgG antibodies and the residual fluorescence was analyzed by FC starting at time point zero and up to 72 hours incubation of the cells at 4° C. in the dark.

E. Whole Cell-ELISA

The number of NlpA-ZZ molecule presented on the inner-membrane of JUDE-1 induced cells and of the equilibrium dissociation constant (KD) of the complex NlpA-ZZ-IgG was determined by whole cell-ELISA assays as follows. NlpA-ZZ induced spheroplasts equivalent to ~1 ml of $A_{600}$=0.1 (108 cells) were incubated with a two-fold dilutions serial of HRP-conjugated-Rabbit IgG antibodies, starting with a concentration of 5 nM for 1 h at RT in PBS containing 1% BSA (1% BPBS). After washing three times with the same buffer detection of bound IgG antibodies was performed by addition of 0.5 ml of the chromogenic HRP substrate TMB (DAKO, USA) to each tube and color development was terminated with 0.25 ml of 1 M $H_2SO_4$. Finally, the tubes were centrifuged for 10 min at 4000 rpm and color intensity of supernatants was measured at 450 nm. The binding-affinity was estimated as the IgG concentration that generates 50% of the maximal signal. Estimation of the number of NlpA-ZZ molecule presented on the inner-membrane of *E. coli* JUDE-1 induced cells was based on the assumption that the binding stoichiometry of NlpA-ZZ to IgG is 1:1.

Example 3

Figure 6B:
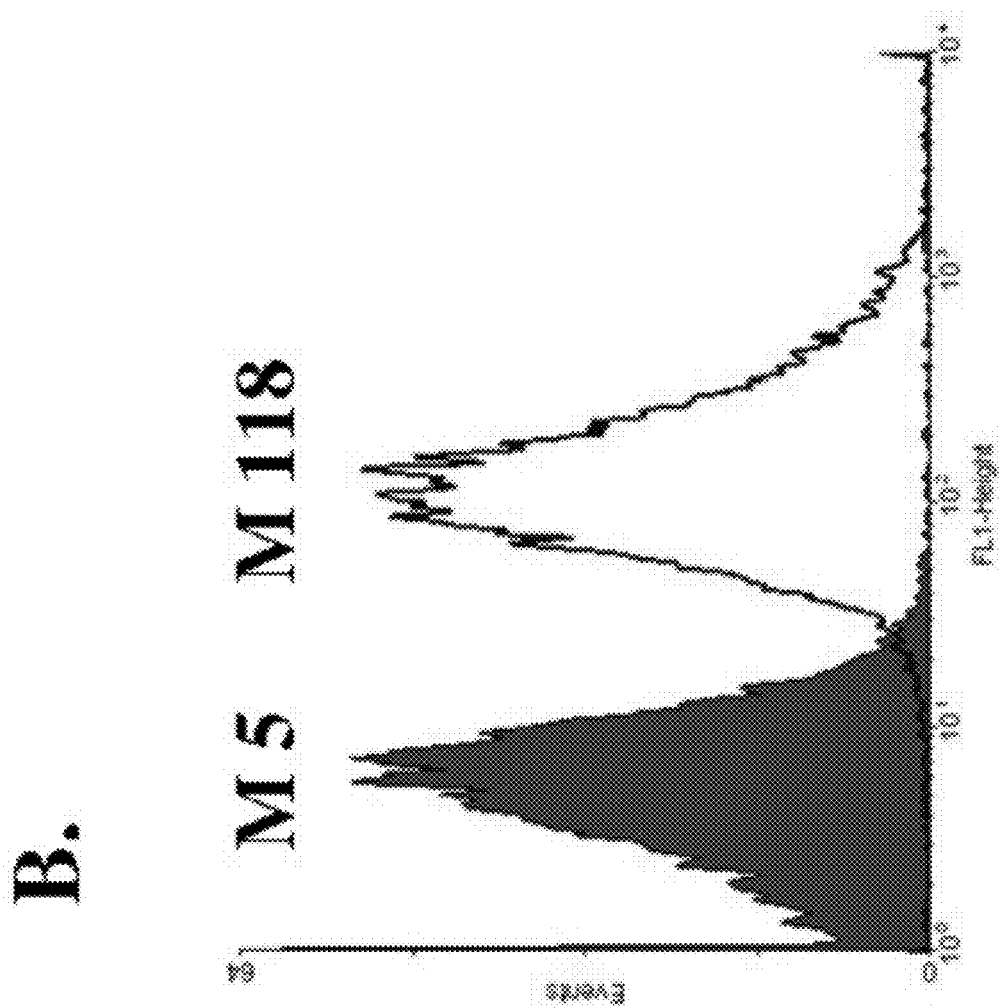
Figure 6C:
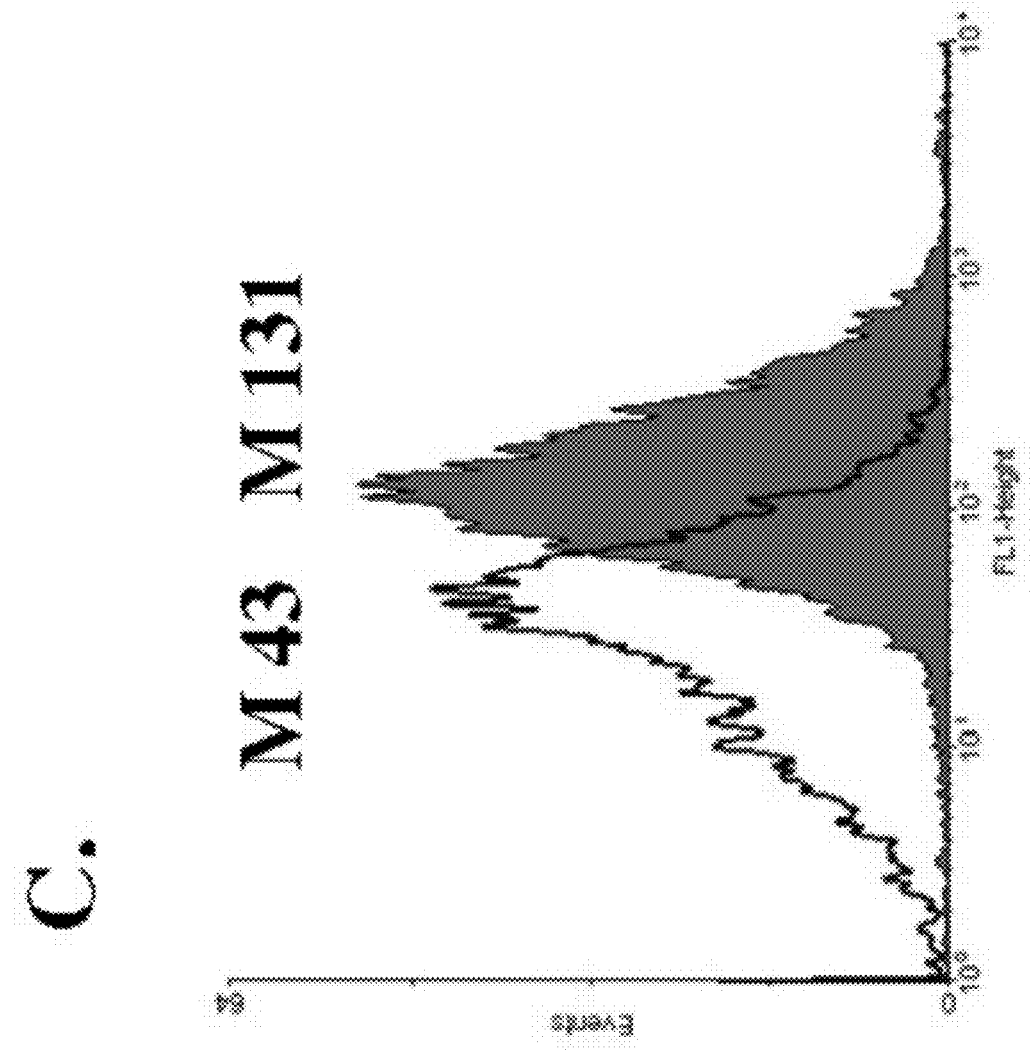
Figure 6D:
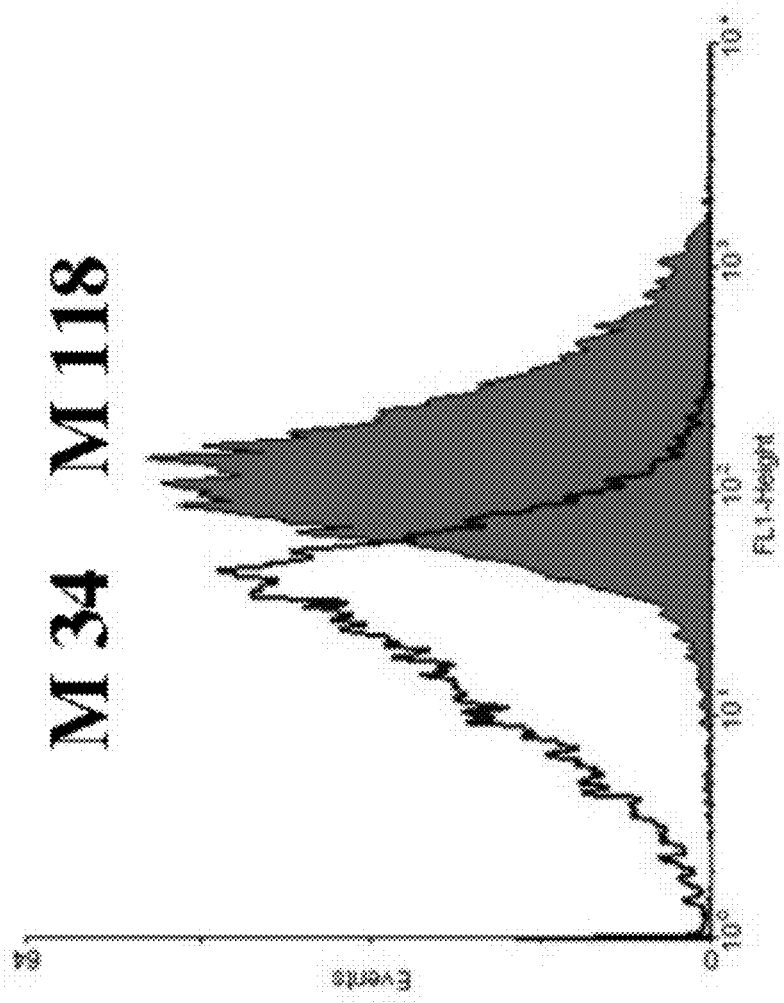

Evaluation of the APEx-ZZ-IgG System by Simultaneous Expression of the NlpA-ZZ and IgG in the Host Cells and Enrichment of Cells Expressing M18.1 Hum IgG Over Cells Expressing 26.10 IgG To evaluate the ability of NlpA-ZZ cells to capture IgG molecules expressed endogenously in the periplasm of the same host cell, *E. coli* harboring the pBAD33-NlpA-ZZ were introduced with pMAZ360-M18.1 Hum-IgG or pMAZ360-26.10-IgG and analyzed by FC for simultaneous expression and capturing of the IgG. As shown (FIG. 6A) when labeled with PA-FITC only cells that coexpressed the M18.1 IgG were fluorescent while cells co-expressing the 26.10 IgG which binds to an unrelated antigen, were not stained. Similarly, incubation with Digoxin-BODYPY™, resulted in labeling only of cells 26.10 IgG bound whereas those expression the M18.1 IgG gave background fluorescence (FIG. 6B). The specificity of the two antibodies to the relevant antigen was further confirmed (FIG. 6C, D).

Figure 7:
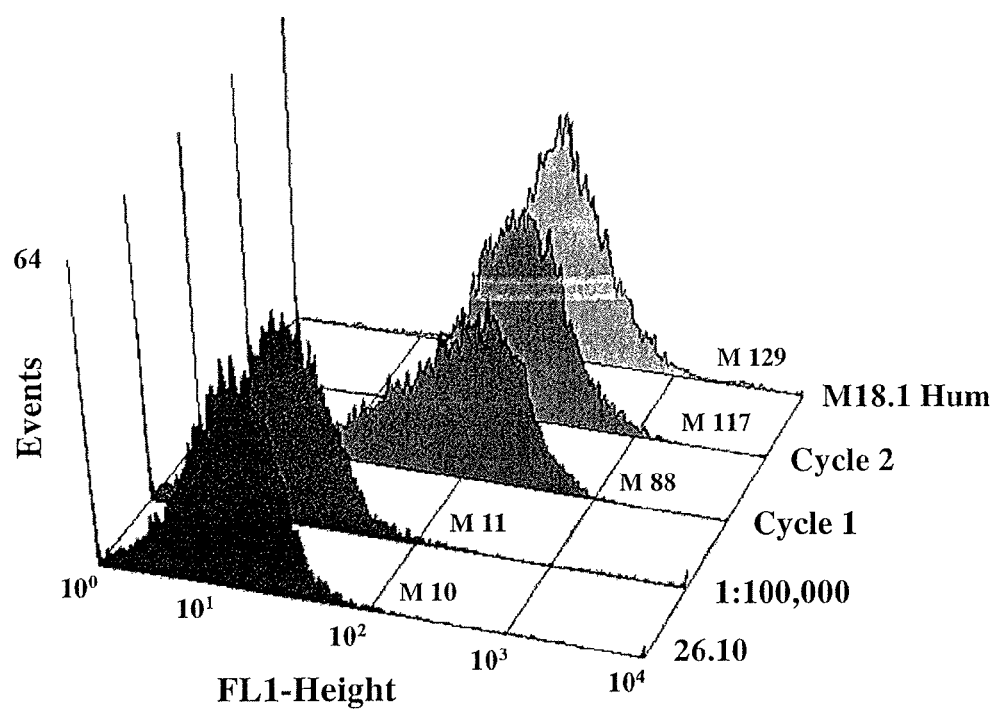
FIG. 7. Bacterial cells displaying an anti-PA antibody can be successfully selected from a mixed population. Z-axis indicated cell treatment conditions 26.10 (negative control for FITC-PA binding), M18.1 Hum (positive control for PA-FITC binding), 1:100,000 (mixed cell population or cell populations after 1 or 2 selection cycles with PA-FITC. FACS analysis is as indicated in FIG. 5.

It was further shown that NlpA-ZZ cells expressing the M18.1 IgG could be enriched from a large excess of cells expressing the 26.10 IgG. Specifically, spheroplasts expressing NlpA-ZZ and also displaying the M18.1 Hum IgG were mixed with a 100,000 fold excess of spheroplasts displaying the 26.10 IgG. Spheroplasts displaying the M18.1 Hum antibody were enriched by two rounds of sorting using a Cytomation MOFLO™ instrument, following labeling with fluorescent M18.1 Hum antigen, PA-FITC. Cells showing high fluorescence were collected and immediately resorted. Following each round of sorting, the IgG DNA was rescued by PCR and ligated into pMAZ360-IgG plasmid. Fresh NlpA-ZZ *E. coli* cells transformed with the resulting plasmids were grown, induced for IgG expression and subjected to next round of sorting against PA-FITC antigen. As shown in (FIG. 7) after two round of sorting M18.1 Hum IgG displaying cells were enriched to approximately 100% of the population. Sequence analysis revealed that following the first round of sorting 7/20 randomly clones were M18.1 Hum, while following the second round 10/10 came out as M18.1 Hum revealing complete enrichment of the desired population.

Example 4

Presentation of Expressed Antibodies

A. Flow Cytometry Analysis

The capture of IgG expressed in the periplasm by NlpA-ZZ expressed within the same cell was evaluated as followed: *E. coli* cells expressing NlpA-ZZ were co-transformed with plasmids pMAZ360-M18.1 Hum-IgG or with pMAZ360-26.10-IgG and single colonies were used to inoculate TB medium supplemented with 30 μg/ml chloramphenicol, 100 μg/ml ampicilin and 2% (w/v) glucose. Cultures were grown at 30° C. and when the optical density reached $A_{600}$=1.0, the cells were pelleted for 5 min at 4,500 rpm. The cells were resuspended in TB medium supplemented with 30 μg/ml chloramphenicol, 100 μg/ml ampicilin and isopropyl β-D-thiogalactoside (IPTG) to induce protein synthesis and growth was continued overnight at 25° C. The following day cells were induced with 0.2% arabinose for additional 3 hours at 25° C. for NlpA-ZZ expression. Following induction, spheroplasts were prepared as in example 2 and labeled with 50 nM of the appropriate fluorescent probe at RT for 45 min before evaluation by FACS. To confirm the specificity of the bacterially expressed IgGs, spheroplasts were incubated with 10 fold molar excess of non-cognizant antigen for 1 h at RT prior to incubation with the fluorescently labeled antigen.

B. Enrichment by FACS Sorting

Enrichment of NlpA-ZZ cells expressing the M18.1 Hum IgG from a 100,000 fold excess of cells expressing the 26.10 IgG was performed as follows: Following preparation of spheroplasts displaying different IgG antibodies, as described in example 4. A, $10^9$ 26.10 IgG displaying cells were mixed with $10^4$ cells displaying the M18.1 Hum IgG. The mixed culture was incubated with 100 nM of PA-FITC antigen for 45 min at RT and analyzed on a MOFLO™ droplet deflection flow cytometer by using a 488-nm Argon laser for excitation. Cells were selected based on increased fluorescence in the fluorescein emission wavelength using a 530/40 band-pass filter. A total of $1.5 \times 10^8$ cells were sorted at 25,000 s$^{-1}$ and $2.25 \times 10^6$ events (1.5%) were recovered. The collected events were immediately resorted through the flow cytometer at 250 s$^{-1}$ and $5 \times 10^4$ (6.5%) events were recovered. Subsequently, a DNA fragment corresponding to the VL-Ck-VH sequence of the IgG gene was amplified by PCR out of the sorted population using primers 5' VL amplifier-FOR and 3' VH amplifier-REV (Table 2). Once amplified, the resulting PCR products were then recloned into pMAZ360-IgG vector, retransformed into NlpA-ZZ cells, and grown overnight on agar plates at 30° C. The resulting clones were grown, induced for expression of IgG and subjected to a second round of sorting during which a population of $8 \times 10^7$ spheroplasts were sorted at a rate of at 25,000 s$^{-1}$ and $2 \times 10^5$ events (0.25%) were captured. Recovered spheroplasts were immediately resorted to recover a final of $5 \times 10^3$ events (17.5%) at 200 s$^{-1}$.

Example 5

Construction and Screening of an Immunized Anti-PA IgG Library

Mice were immunized with the PA antigen (PA-83). After booster immunization the antibody titer elevated antibody titer was detected. Total RNA was recovered and cDNA was prepared using standard methods (REF), heavy and light chain variable domains were amplified using a modification of a primer set designed for the construction of mouse scFv libraries (Krebber et al., 1997). The primer set was designed to facilitate efficient cloning of the VH and VL variable domains separately as NheI/HindIII and NcoI/NotI restriction fragments, respectively, into the pMAZ360-IgG expression vector.

Figure 8A:
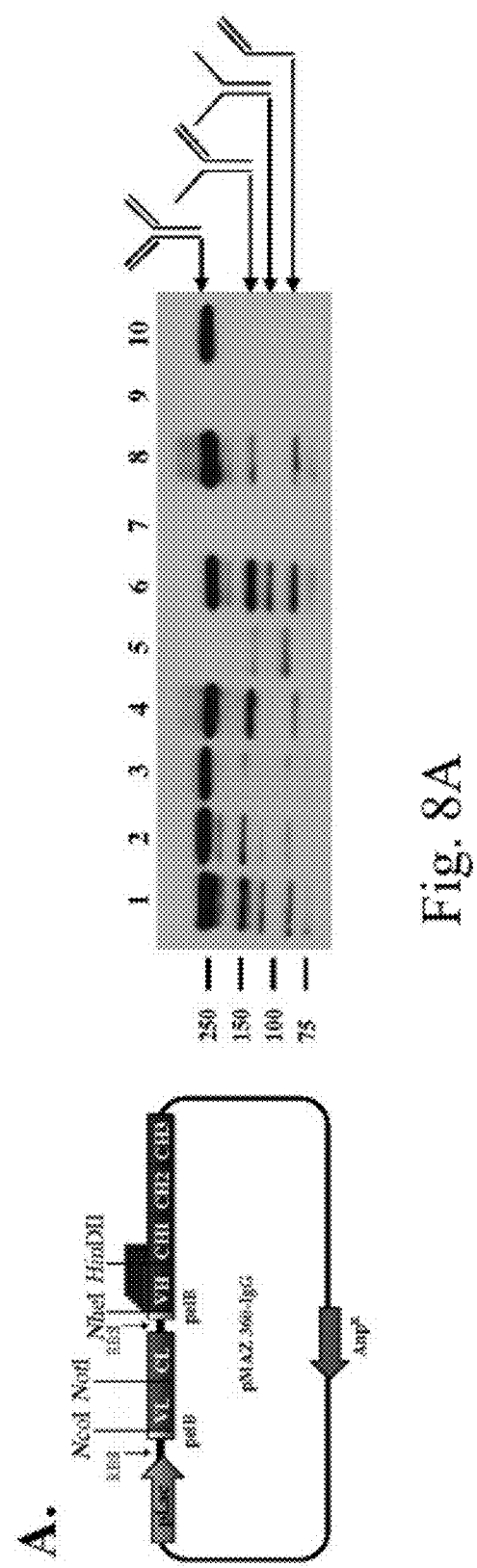
FIG. 8A-B. A schematic diagram showing the construction of a VH (FIG. 8A) or VH and VL (FIG. 8B) antibody library.
Figure 8B:
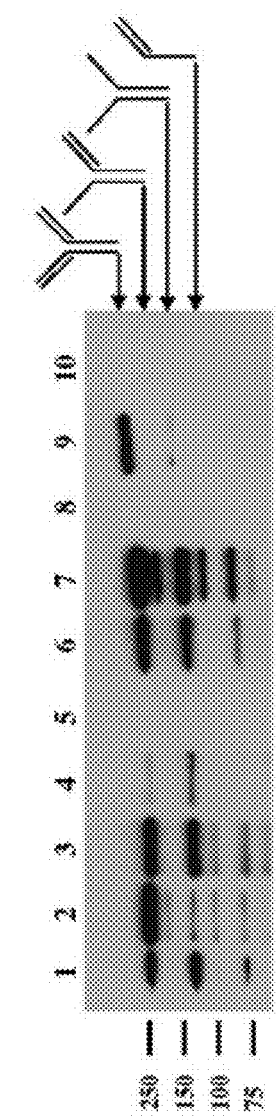
Figure 9:
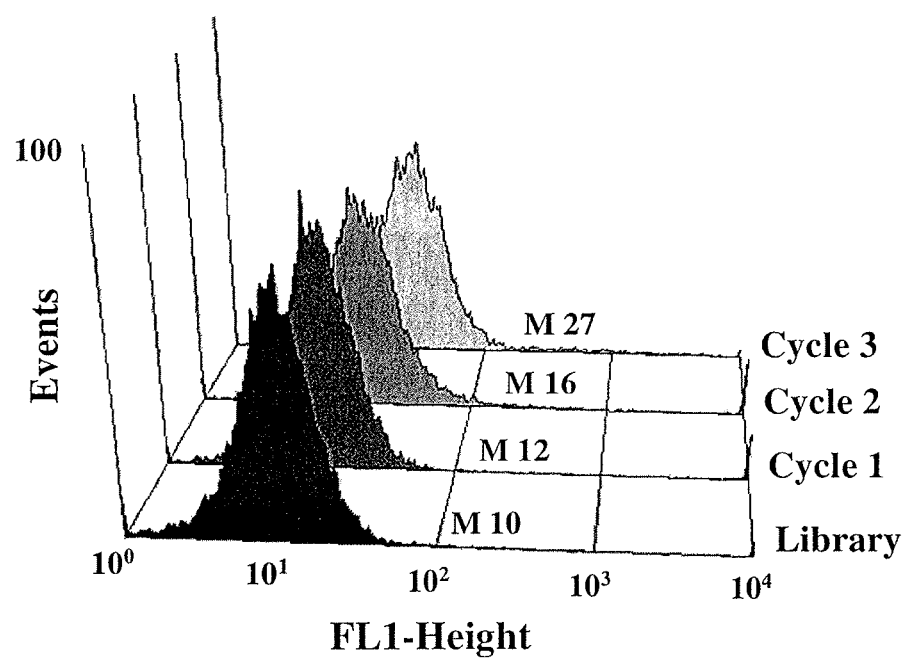
FIG. 9. Bacteria displaying a library of antibodies may be efficiently selected for ligand binding according to the invention. The number of cells that exhibit PA-FITC mediated fluorescence is increased with each selection cycle (as indicated on the z-axis). FACS analysis is displayed as in FIG. 5.

The anti-PA IgG library was constructed by two consecutive steps. First, the variable VH domains were ligated into the pMAZ360-IgG plasmid to generate a library of $10^7$ independent transformants. The VH library was evaluated for expression of full-length IgGs in *E. coli* periplasm by analyzing 10 library clones selected at random. Western-blot analysis showed that 70% of the randomly selected clones expressed intact IgGs (FIG. 8A). DNA analysis of 10 individual clones revealed that each encoded a different VH sequence, as expected. DNA from the library was pooled and the VL variable domains were cloned into the VH library vector to generate a final anti-PA IgG library of $10^7$ independent clones. The accomplished IgG library was analyzed for expression of full assembled IgG antibodies in the bacterial periplasm, showing 70% productivity for intact IgGs (FIG. 8B). DNA analysis of 10 randomly picked clones confirmed sequence variation within the library. The anti-PA IgG library was subjected to three rounds of sorting against PA antigen. Briefly, in each round library cells were grown under conditions facilitating induction and capturing of soluble IgG molecules in the bacterial periplasm, cells were treated with Tris-EDTA-lysozyme, washed and labeled with 100 nM of PA-FITC for affinity and Alexa Flour 647-Chicken anti-Human IgG for monitoring IgG expression. The library was subjected to three rounds of sorting using the MOFLO™ flow cytometer ending with a significant enrichment signal as indicated by FC (FIG. 9). For screening analysis 200 clones from second round of sorting and 400 clones from the third round of sorting were grown in 96-wells plates and induced for expression of IgG, soluble cell extract of the individual clones was analyzed for direct binding to PA antigen via ELISA. Following sequence alignment of a comprehensive set of positive clones, 5 individual clones were identified as unique (FIG. 10).

Example 6

Selection of Antibodies from an Expression Library

A. Construction of Immunized Anti-PA IgG Library

Construction of the anti-PA IgG library was performed as follow: Three female BALB/c mice of 6-8 weeks of age were immunized with the monomer subunit of *Bacillus anthracis* protective antigen (PA-83) (List Biological Labs, USA) in complete Freunds adjuvant. Mice were boosted three times at intervals of two weeks using 40 µg of PA-83 foe weeks 2 and 4 and a final booster of 100 μg at week 6. The mice were bled three days after each boost and the serum anti-PA antibody titer was determined by an ELISA. Total RNA was extracted from 59 mg of spleen tissue using MIRVANA™ miRNA Isolation Kit (AMBION®, USA). mRNA was recovered from total RNA using MICROPOLY(A)PURIST™ mRNA Purification Kit (AMBION®, USA) and cDNA was produced using SUPERSCRIPT™ III (INVITROGEN™, USA) with an anchored oligo-d(T) primer. Heavy and light chain variable domains were amplified in PCR using a set of primers that was designed to facilitate efficient cloning of the VH and VL variable domains separately into the pMAZ360-IgG expression vector. Construction of the anti-PA IgG library was performed in two consecutive steps, initially; the variable VH domains were introduced into plasmid pMAZ360-IgG as NheI/HindIII restriction fragments to generate a library of $10^7$ independent VH domains. Following sequence validation of the VH library the VL variable domains were cloned into the VH library vector as NcoI/NotI to generate a final anti-PA IgG library of $10^7$ independent clones. Determination of full-length IgG expression in *E. coli* periplasm among randomly selected clones was performed on a small scale of 1 ml essentially as described in example 2.B.

B. Library FACS Sorting.

Sorting of the anti-PA IgG library by FACS was performed as follow: Following preparation of spheroplast displaying IgGs as described in example 4.A, cells equivalent to ~1 ml of $A_{600}$=1 ($10^9$ cells) were incubated with 100 nM of PA-FITC antigen and Alexa Flour 647-Chicken anti-Human IgG Fc-specific (diluted 1:50) for 45 min at RT and analyzed on a MOFLO™ droplet deflection flow cytometer by using a 488-nm and a 633 nm Argon lasers for excitation. Cells were selected based on improved fluorescence in the fluorescein and Alexa Flour 647 emission spectrum detecting through a 530/40 and a 670/20 band-pass filter, respectively. The library was subjected to three consecutive rounds of sorting under the following conditions: in round one a total of $1.15\times10^8$ cells were sorted recovering $2.85\times10^6$ events (2.5%) at 25,000 $s^{-1}$. Next, $5.5\times10^5$ of the spheroplasts captured were immediately resorted through the flow cytometer recovering $1.35\times10^5$ events (22%) at 200 $s^{-1}$. The conditions for round two and three were as follow: sort 2; $6.45\times10^7/3.2\times10^5$ (0.5%) at 25,000 $s^{-1}$; resort 2 $3.55\times10^4/2.3\times10^4$ (65%) at 250 $s^{-1}$; sort 3; $6.5\times10^7/3.4\times10^5$ (0.5%) at 25,000 $s^{-1}$; resort 3 $2.25\times10^3/1.65\times10^3$ (72%) at 600 $s^{-1}$. Following each round of sorting a DNA fragment corresponding to the VL-Ck-VH sequence of the IgG gene was amplified out of the sorted population by PCR using primers 5' VL amplifier-FOR and 3' VH amplifier-REV (Table 2). Once amplified, the resulting PCR products were recloned into pMAZ360-IgG vector, retransformed into NlpA-ZZ cells, and grown overnight on agar plates at 30° C. The resulting clones were grown, induced for expression of IgG and subjected to additional round of sorting. Following three rounds of sorting the PCR recovered IgG genes were ligated into pMAZ360-IgG expression vector and transformed to fresh *E. coli* JUDE1 cells for expression of soluble non-captured IgG antibodies.

C. Library Screening by Direct Binding ELISA.

Randomly selected single colonies from B above were used to inoculate 200 µl of LB medium supplemented with 100 µg/ml ampicillin and 2% (w/v) glucose per well in U-bottom 96-well plates. Following over night growth at 30° C. with shaking at 150 rpm, the cutlers were subcultured by dilution of 1:20 to inoculate 200 µl of TB medium supplemented with 100 µg/ml ampicillin and 2% (w/v) glucose in fresh 96-well plates and grown for 3 hour at 30° C. with shaking at 150 rpm. Next, the plates were centrifuged for 15 mM at 4450 rpm and pellets were resuspended in TB medium supplemented with 100 µg/ml ampicillin and 1 mM isopropyl-1-thio-1-D-galactopyranoside (IPTG). Cells were induced ON at 25° C. with shaking at 150 rpm for expression of the selected IgG antibodies. The following day the plates were centrifuged and the cell were lysed in 200 µl of 20% BUGBUSTER™ HT Protein Extraction Reagent in PBS for 20 min at RT. The plates were centrifuged as above and of soluble cell lysates were tested for direct binding to the PA antigen as follows; ELISA plates were coated with 10 µg/ml of PA in PBS at 4° C. for 20 h and blocked with 2% (v/v) non-fat milk in PBS (MPBS) for 2 h at RT. Next, 25 µl of soluble cell lysates from library clones were applied into plates containing 75 µl of MPBS and incubated for 1 hour. Subsequently the plates were washed 3 times with PBST. Bound IgG was detected with HRP-conjugated goat anti human antibodies (×10,000 dilution in MPBS). The ELISA was developed using the chromogenic HRP substrate TMB and color development was terminated with 1 M $H_2SO_4$. The plates were read at 450 nm.

Example 7

Binding Characterization of Selected IgG Clones

Figure 11:
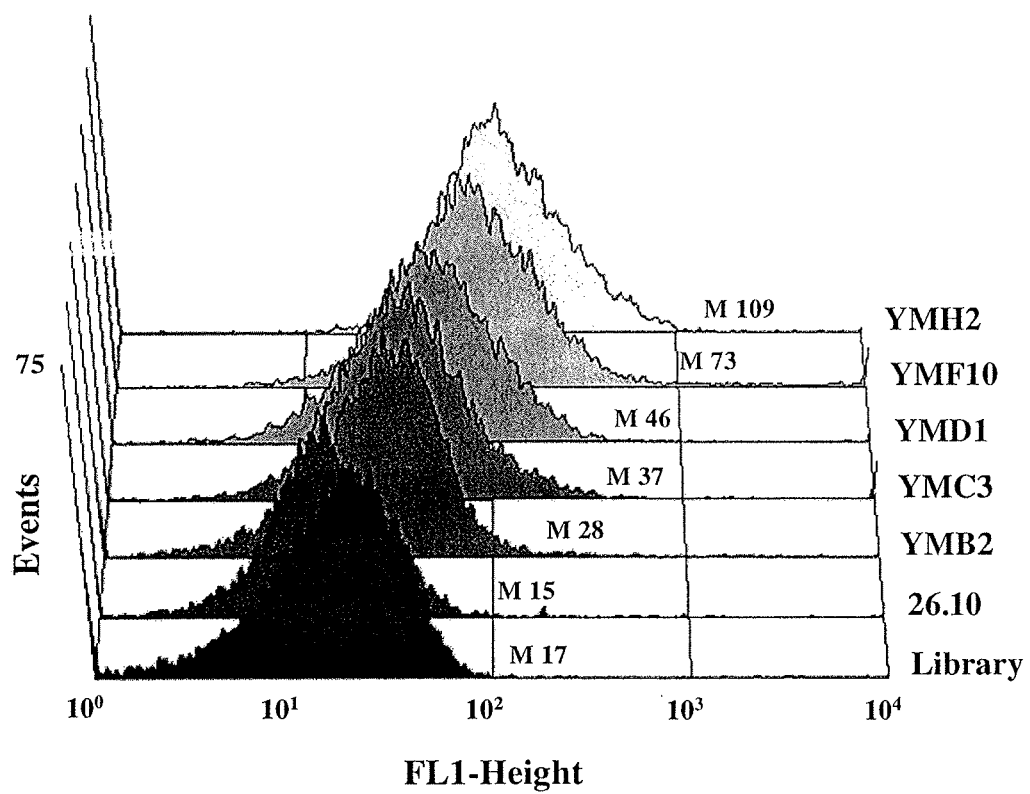
FIG. 11. Bacterial cells expressing each of the indicated antibodies or libraries (z-axis) were assessed for PA-FITC fluorescence by FACS. Data is graphed as indicted in FIG. 5.

Five clones that gave the highest ELISA signal were characterized further. First, the 5 selected anti-PA IgG clones were tested for binding to PA antigen by FACS (FIG. 11). The FACS signal exhibited by the various clones is a function of the expression level and the affinity for the PA antigen. To evaluate the expression levels and to determine the binding affinities, the 5 selected IgG antibodies were over expressed and purified on a protein A column. 12%/SDS-PAGE under non-reducing conditions (FIG. 12A) and reducing conditions (FIG. 12B) revealed that the expression yields of purified material were between 0.2-1 mg/l of cells.

Antigen association and dissociation rate constants and equilibrium dissociation constants were determined by Surface Plasmon Resonance analysis on a BIACORE® 3000 (BIACORE®) instrument using two different methods. The first is based on direct binding to antigen-immobilized chip, performed essentially as described in (Harvey et al., 2004). Briefly, 750 response units of PA-83 or PA-63 were coupled to a CM5 chip in the same way described above. BSA was similarly coupled and used for in-line subtraction and the second involved IgG capturing by anti-Fc antibody followed by injection of the antigen as analyte. The second method is a modification of a method described by (Canziani et al., 2004). Briefly, goat anti human IgG1 Fcγ fragment specific (Jackson Laboratories) was coupled to two in-line flow cells of a CM5 chip at 30 µl/min to an equivalent of 10,000 response unit by using 1-ethyl-3-(3-dimethylaminopropyl)carbodiimide/N-hydroxysuccinimide chemistry. Varying concentration of purified antibodies in Hepes-buffered saline-EP buffer (BIACORE®) were injected at a flow rate of 5 µl/min at 25° C. to achieve approximately 500 response units of captured IgGs. Buffer and antigen were then injected serially through in-line flow cells at a flow rate of 50 µl/min (5 minute stabilization, 1 minute association, 5 minute dissociation) and the surface was regenerated using two pulses of 100 mM $H_3PO_4$. Threefold dilution series of PA-63 starting at 15 nM were analyzed in duplicate using the BIAevaluation software (BIACORE®) with appropriate subtraction methods. All kinetic analysis were performed at 25° C. in Hepes-buffered saline-EP buffer at a flow rate of 100 ul/min and regeneration was performed with one injection of 4M $MgCl_2$. IgGs were injected at 10 nM and analyzed using BIAevaluation software.

Example 8

Screening of IgG Libraries by Phage Display

Figure 14A:
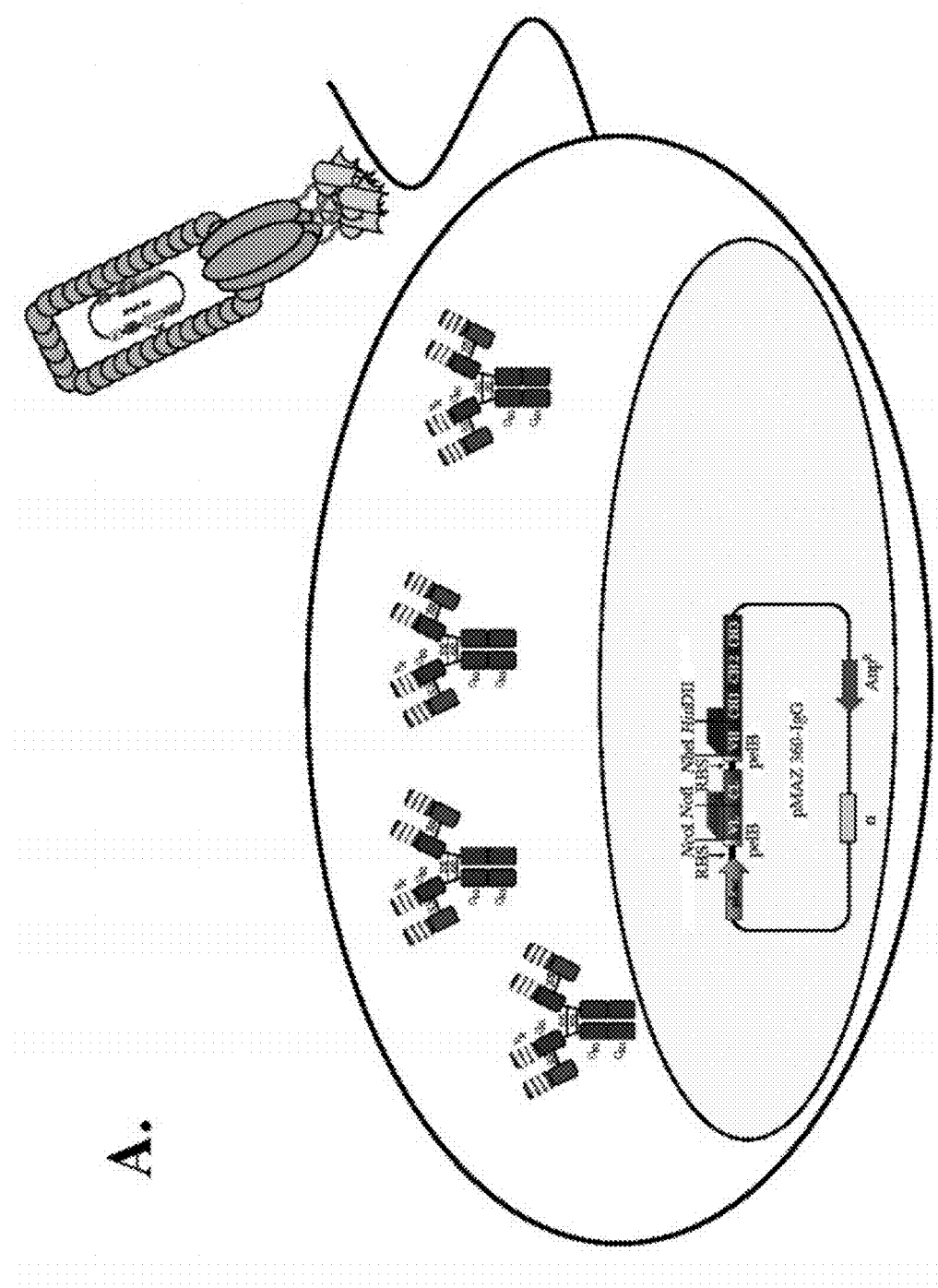
FIG. 14A-B. A schematic diagram showing antibody phage display methods of the invention. Bacteria expressing antibodies in the periplasmic space may be infected with a phage comprising a coat protein fused to an antibody-binding domain (FIG. 14A) thereby producing phage that displays the antibody and comprises a nucleic acid encoding the antibody (FIG. 14B).
Figure 14B:
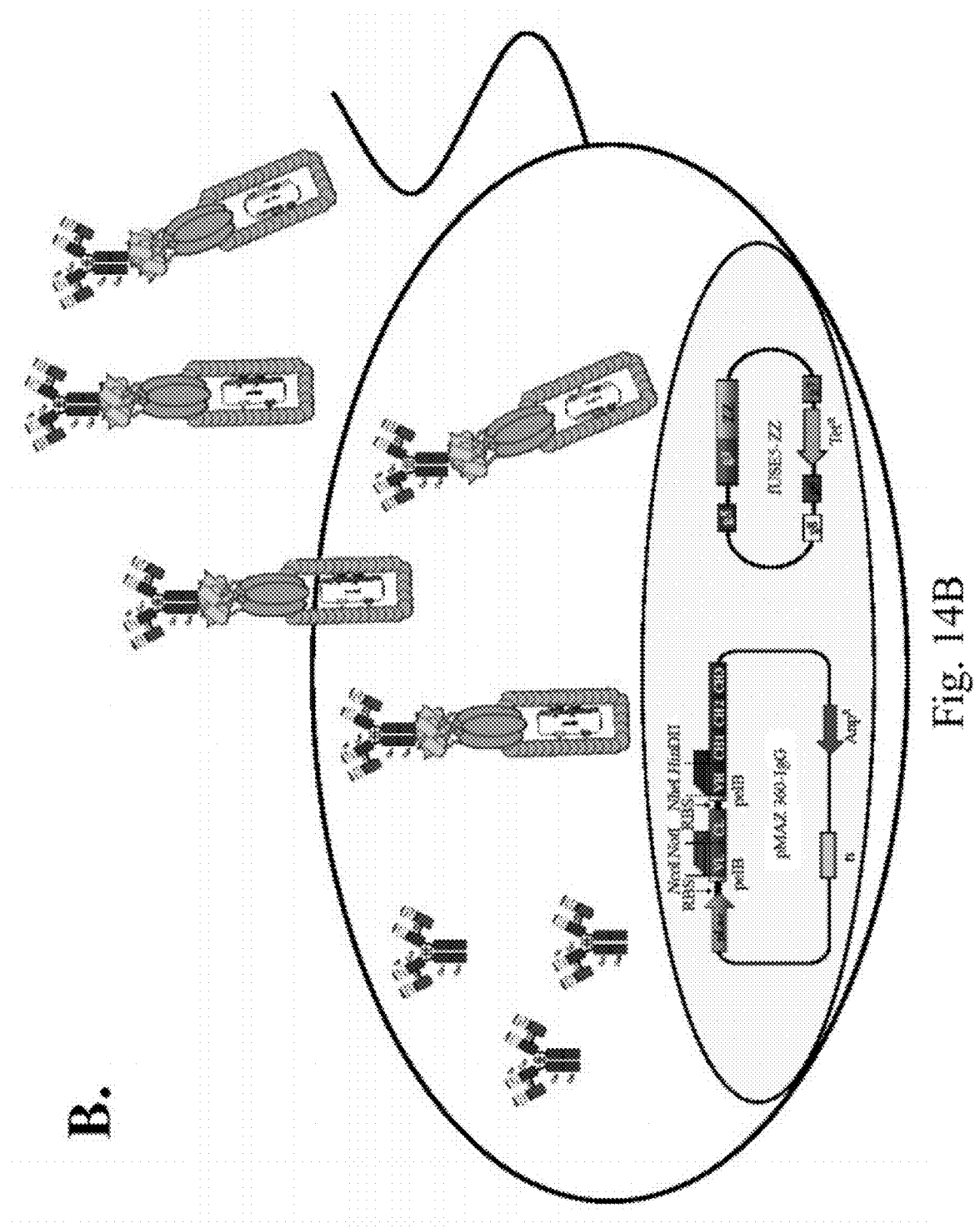

For IgG phage-display, *E. coli* K91K/F' cells (Smith and Scott, 1993) expressing soluble IgG antibodies in the periplasm were infected with FUSE5-ZZ phage (Yacoby et al., 2006). These phage particles allow polyvalent display of the IgG-Fc binding protein ZZ, on all copies of the p3 minor coat protein of filamentous bacteriophage. The FUSE5-ZZ phage in this system performs not only as helper phage but also in turn capture the IgG antibody in the periplasm via the ZZ moiety. Rescued FUSE5-ZZ-IgG phage particles (which preferentially harbor the high copy number pMAZ360-IgG phagemid over the replication-defective FUSE5-ZZ genome) are selected for antigen binding by several rounds of phage panning (FIG. 14). FUSE5-ZZ phage particles although displaying the ZZ protein on all copies of the p3 minor coat protein are well capable to infect and propagate in *E. coli*/F' cells.

For the evaluation of the IgG phage-display system the anti-PA M18.1 Hum IgG and the anti-digoxin 26.10 IgG served as models antibodies. Initially, purified FUSE5-ZZ phage particles were evaluated for their capabilities to capture IgG in solution. Phage particles were prepared and mixed with purified M18.1 Hum IgG or 26.10 IgG antibodies. After washing to remove any excess, unbound antibodies the phage particles were analyzed by ELISA. Phage that had captured the anti-PA and antidigoxin antibodies showed a strong signal on plates coated with the respective antigens but not on plates coated with unrelated antigens.

FUSE5-ZZ phage formed in cells that also express IgG antibodies within the periplasm were shown to be capable of capture of the antibodies. *E. coli* K91K/F' cells transformed with the phagemids pMAZ360-M18.1 Hum-IgG and with pMAZ360-26.10-IgG were grown under conditions permissive for phage infection. Following infection with FUSE5-ZZ phage, the cultures were allowed to grow over night under conditions favorable for phage production. The following day phage particles were precipitated and evaluated for specific binding by direct ELISA (FIG. 15). The results obtained confirmed that assembled FUSE5-ZZ produced in cells expressing the M18.1 Hum-IgG bound specifically to PA while phage produced in cells expressing the 26.10-IgG antibody bound specifically to plates coated with digoxin.

The IgG captured by the ZZ-displaying phage is kinetically very stable as competition of the bound IgGs by excess of unrelated IgG resulted in only a low reduction in the specific ELSA signal. The stable interaction of the complex ZZ-IgG although non-covalent is most likely attributed to the polyvalent display of the ZZ domain on all copies of the phage p3 coat protein. Hence, the adjacent ZZ molecules contribute by avidity manners to capture and retain the IgG molecules in a very stable way.

Example 9

Expression of Antibodies on Phage

A. Propagation of FUSE5-ZZ Phage

*E. coli* K91K/F' were grown at 37° C. and harvested in exponential (logarithmic) growth phase ($0.6 \leq A_{600}$ nm $\leq 0.8$) to maximize the expression of the F pili proteins. Cells transformed with FUSE5-ZZ DNA were inoculated ON at 30° C. in 5 ml of 2×YT medium supplemented with 20 µg/ml tetracycline and 50 µg/ml kanamycin. The following day cultures were diluted into 500 ml of 2×YT medium supplemented with 20 µg/ml tetracycline and grown overnight with shaking (250 rpm) at 30° C. Cells were pelleted at 6000 rpm for 15 min at 4° C. and the supernatant was filtered and mixed with ⅕ volume of PEG/NaCl and incubated for 2 hr or more on ice. Phage-precipitates were collected by centrifugation at 7,800 rpm for 30 min at 4 C and the supernatant was carefully aspirated off. The phages were resuspended in sterile and filtered PBS and kept at 4 □C. To titer the phage stock, 10-fold serial dilutions of the phages were made in sterile 2×YT medium. A logarithmic *E. coli* K91K/F' culture was infected with the diluted phages and the mixed culture was incubated for 30 min at 37° C. without shaking followed by incubation for 30 min at 37° C. with gentle shaking. Infected cells were plated on 2×YT plates supplemented with 20 µg/ml tetracycline and 50 µg/ml kanamycin and grown overnight at 37° C.

B. In vitro Coupling of Purified IgGs to FUSE5-ZZ Phage

A stock solution of $5 \times 10^{11}$ CFU/ml FUSE5-ZZ phage particles was mixed with 200 nM of purified M18.1 Hum IgG or 26.10 IgG in PBS. The mixture was rotated head-over-head for two hours at RT. Next, phage particles were precipitated with PEG-NaCl as described above; the supernatant was carefully aspirated off and the phage were resuspended in sterile and filtered PBS and kept at 4° C.

C. Preparation of FUSE5-ZZ-IgG Phage

For preparation of the FUSE5-ZZ-IgG phage particles, a single colony of *E. coli* K91K/F' cells transformed with phagemids pMAZ360-M18.1 Hum-IgG or with pMAZ360-26.10-IgG was grown ON at 30° C. in 5 ml of 2×YT medium supplemented with 100 µg/ml ampicillin, 50 µg/ml kanamycin and 2% glucose. The following day the culture was diluted 1:100 into 10 ml of 2×YT medium supplemented with 100 µg/ml ampicillin and 2% glucose. Cells were grown with shaking at 37° C. until $0.6 \leq A_{600} \leq 0.8$ followed by addition of FUSE5-ZZ helper phage at a ratio of 1:20 (number of bacterial cells: helper phage particles, taking into account that $A_{600}=1\sim10^9$ bacteria/ml). For infection, the cultures were incubated without shaking at 37° C. for 60 min and then transferred to a shaking 37° C. incubator at 110 RPM for 30 min. The infected cells were collected by centrifugation and resuspended in 40 ml of 2×YT medium supplemented with 100 µg/ml ampicillin and 20 µg/ml. For phages proliferation, the cultures were incubated with shaking (250 RPM) at 30° C. overnight. The following day, FUSE5-ZZ-IgG phage particles were precipitated with PEG-NaCl as described above; the supernatant was carefully aspirated off and the phage were resuspended in sterile and filtered PBS and kept at 4° C.

D. Phage-ELISA

ELISA plates were coated with 10 µg/ml of PA or 10 µg/ml of digoxin-BSA in PBS at 4° C. for 20 h and blocked with 2% (v/v) non-fat milk in PBS (MPBS) for 2 h at RT. Next, 50 µl of $10^{12}$ CFU/ml of FUSE5-ZZ-IgG phage particles were applied in a three-fold dilution series into plates already containing 100 µl of MPBS and incubated for 1 hour at RT.

To evaluate the stability of binding of IgG onto the phage, $10^{10}$ FUSE5-ZZ-IgG phage particles were incubated with 1 µM of commercial Human IgG as a competitor for 1 h at RT and then the mixture was applied onto ELISA plates. Following incubation the plates were washed 3 times with PBST. Bound phage particles were detected with HRP-conjugated goat anti M13 antibodies (×5,000 dilution in MPBS). The ELISA was developed using the chromogenic HRP substrate TMB and color development was terminated with 1 M $H_2SO_4$. The plates were read at 450 nm.

Example 10

Enrichment of FUSE5-ZZ-IgG Phage Particles by Antigen Bio-panning $10^{10}$ FUSE5-ZZ-M18.1 Hum-IgG phage particles were mixed with $10^4$ FUSE5-ZZ-26.10-IgG and vice versa. The two mixed phage populations were subjected to three rounds of bio-panning each on immunotubes coated with PA or digoxin-BSA, respectively. ELISA analysis of the isolated close revealed a significant enrichment of the respective phages (FIG. 16A, FIG. 16B). Thus, intact IgG molecules can be efficiently expressed in *E. coli* periplasm and subsequently be captured and displayed on phage articles that in turn can be screened for specific antigen enrichment. These experiments illustrate that IgG with a desired specificity can be selected directly from libraries.

Example 11

Selection of Antibody Presenting Phage

A. Phage Bio-pannin.

A 35 mm tissue-culture six-well plate was coated overnight at 4° C. with 75 µg/ml of PA or 100 µg/ml of digoxin-BSA in PBS in a total volume 0.7 ml. After discarding the excess solution, the wells were washed once with PBS and blocked with 3 ml of PBS containing 0.25% (w/v) gelatin (PBSG) for two hours at RT. Next, the wells were washed five times with PBS and incubated with the suitable phage population in a total volume of 0.7 ml on PBS and rocked gently at RT for two hours. Unbound phages were rinsed away and the plate was washed extensively ×10 with PBS containing 0.05% (v/v) Tween 20 (PBST) followed by ×5 washes with PBS. Bound phages were eluted with the addition of 400 µl of elution buffer (0.1 M HCl adjusted to pH 2.2 with glycine, 1 mg/ml of BSA) for ten minutes at room temperature with gentle agitation. The eluted phage particles were transferred into a 1.5 ml microfuge tube and neutralized with 75 µl of neutralizing buffer (1 M Tris-HCl, pH 9). The selected phages were used for re-infection of *E. coli* K91K/F' cells for enrichment. 0.5 ml of the neutralized eluted phages were mixed with 4.5 ml 2×YT medium and 5 ml of logarithmic K91K/F' cells. For infection, cultures were incubated without shaking at 37° C. for 60 min and then transferred to a shaking 37° C. incubator at 110 RPM for 30 min. The infected cells were spread on 2×YT plates supplemented with 100 µg/ml ampicillin, 50 µg/ml kanamycin and 2% glucose and grown overnight at 30° C. Titration of output and input phages was done after every panning cycle. Phages at 10-fold serial dilutions were used to infect logarithmic *E. coli* K91K/F' cells. The cultures were incubated for 30-60 min at 37° C. 10 ml samples were plated in duplicates on 2×YT plates supplemented with 100 μg/ml ampicillin, 50 μg/ml kanamycin and 2% glucose and grown overnight at 30° C.

Preparation of input phage was performed as follows: following incubation of the plates ON at 30° C., the cells were scraped and sub-cultured into 50 ml of 2×YT medium supplemented with 100 μg/ml ampicillin, 50 μg/ml kanamycin and 2% glucose to give a starting A600=0.1. The cultures were grown with shaking at 37° C. until $0.6 \leq A600 \leq 0.8$ followed be removal of 10 ml of each culture for infection with FUSE5-ZZ helper phage. Infection and production of FUSE5-ZZ-IgG phage particles was performed essentially as described in example 10.C. Evaluation of the enrichment of the two mixed population was performed by ELISA as described in example 10.D.

Example 12

Construction of a Semi-synthetic Chimeric IgG Library Based on a Single-framework Scaffold A very large semi-synthetic IgG library with a total size of $3 \times 10^9$ clones was constructed. The library was designed using the scaffold of the anti-PA YMF 10 IgG that was isolated from the immunized anti-PA library. Clone YMF10 variable $V_H$ and Vκ genes were selected as scaffold donors since the resultant full-length of this antibody demonstrated high expression levels in *E. coli* periplasm and efficient assembly of the heavy and light chain into full-length IgG. Further, this antibody belongs to the canonical family 12211 which is the most common among antibodies and is multispecific in its binding capabilities toward a variety of antigens, including binders to proteins, surface antigens, nucleic acids and small molecules such as haptens (Vargas-Madrazo et al., 1995).

For single-framework libraries, diversity depends solely on the degeneracy of synthetic DNA used to vary the CDR loop sequences. Randomization was introduced to both CDR3 regions of YMF10 $V_H$ and Vκ genes simultaneously, since these two regions form the inner-circle of the antigen binding site, and therefore show the highest frequency of antigen contacts in structurally known antibody-antigen complexes. In this example the DNA sequence of clone YMF10 variable genes was aligned with all functional sequences of antibodies deposited in the IgBLAST data base (on the World Wide Web at ncbi.nlm.nih.gov/igblast/) and the CDR3 sequences of approximately 500 clones that scored the highest homology were aligned and at each position the amino acids were ranked by the frequency of occurrence in CDRH3 (Table 3) and CDRL3 (Table 4). The rational behind this approach is that within the CDRs, particular residue positions are not as hypervariable as classified. For example, in naturally occurring CDRs a propensity towards the occurrence of Tyr, Ser, Trp, Gly and Asn residues is notable (de Kruif et al., 1995; Fellouse et al., 2007). These residues possess structural and functional characteristics that appear highly desirable for antibody binding sites. The inventors reasoned that such "designed" CDR3 regions would increase the frequency of cells expressing functional antibodies, thus resulting in a more efficient exploitation of library size which is limited to bacterial transformation capabilities.

In the Kabat numbering scheme, CDRH3 is defined as the sequence from positions 95-102. To obtain the highest degree of diversity in CDR3 of $V_H$, six degenerate oligos were designed encoding 7-12 residues (Table 3), corresponding to the most frequent distribution of CDRH3 length in functional antibodies. Randomization of CDRL3 was carried out using one degenerate oligo introducing only limited randomization to selected positions while other residues that are considered as consensus among antibodies were kept as in the parental clone (Table 4). At the N-terminal boundary of CDRH3, additional randomization was introduced to the parental sequence at positions 93-94 of the framework corresponding to the sequence found most commonly amongst natural antibodies. Thus, for both the heavy and light chain CDR3 regions, diversity was designed in a way that at most amino acid positions, the most frequent residues in natural antibodies (bold amino acids in Tables 3 and 4) were encoded by a tailored degenerate codon (italicized nucleotides in Tables 3 and 4) while minimizing the residues not included in the target diversity (non-bold amino acids in Tables 3 and 4). The over all coverage of the target diversity for both Table 3 and 4 was in the 75-95% range.

The semi-synthetic IgG library was constructed in two consecutive steps using DNA of plasmid pMAZ360-YMF10-IgG as a template. First, the variable Vκ genes were amplified in a PCR reaction using the set of primers listed in Table 5 (NotI and HindIII sites in CDRL3 and CDRH7-12 primers, respectively, are underlined in Table 5). The resulting set of variable Vκ domains were introduced into plasmid pMAZ360-IgG as NcoI/NotI restriction fragments to generate a library of $10^7$ independent transformants. Next, the variable $V_H$ genes were amplified in six independent PCR reactions corresponding for the six different length of CDRH3 that varied between 7-12 amino acids using the set of primers listed in (Table 5). The resulting set of variable $V_H$ genes was inserted separately into the Vκ library vector as NheI/HindIII fragments generating six separate libraries in the range of $4-6 \times 10^8$ independent transformants. Incorporation of all six libraries together gave rise to a final library with a total size of $3 \times 10^9$ IgG clones. All PCRs were carried out in a volume of 50 μl with 200 μM dNTPs, 1 μM of each primer and 2 units of Vent® DNA Polymerase (NEB, MA). PCRs consisted of 35 cycles of 30 sec at 94° C., 1 min at 58° C. and 1 min at 72° C.

Figure 17:
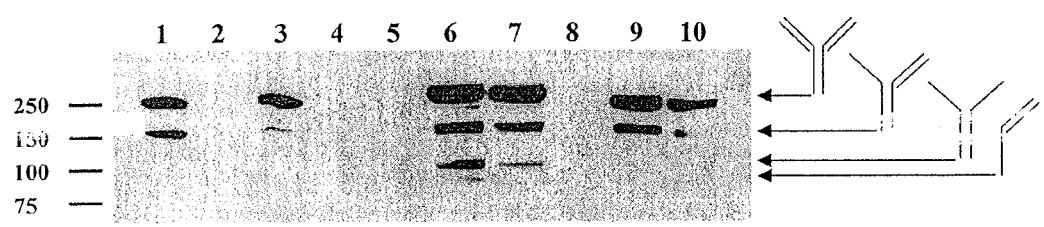
FIG. 17. The productivity of the semi-synthetic library can be evaluated by monitoring the expression of fully assembled IgGs in the E. coli periplasm by analyzing library clones selected at random. HRP-conjugated goat anti-human IgG was used to detect IgG expression. The membrane was developed using the Renaissance® Western blot chemiluminescence reagent (NEN, USA) according to the supplier's instructions. Top arrow indicates folded fully assembled hetero-tetramer IgG1.

Determination of full-length IgG expression in *E. coli* periplasm among randomly selected clones was performed on a small scale of 1 ml essentially as described in Example 2.B. and the yield was determined by western-blot analysis. Approximately 80% of the clones expressed full-length antibodies (FIG. 17). DNA analysis of clones carrying inserts of full-length IgGs confirmed sequence variation within CDRH3 and CDRL3 of library members. At most positions, the highest-ranking amino acid residues were encoded by the tailored degenerate codons with an overall coverage of the target diversity in the 75-95% range.

Example 13

Screening of the Semi-Synthetic IgG Library

Library Two-color FACS Sorting

To demonstrate the capabilities of the semi-synthetic library to produce antibodies against an array of antigens, the human Annexin V, a 35 kDa phospholipids binding protein was selected as a target antigen. Sorting of the semi-synthetic library was performed using a two-color FACS as follow: in each round library cells were grown under conditions facilitating induction and capturing of soluble IgG molecules in the bacterial periplasm. Cells were treated with Tris-EDTA-lysozyme, washed and labeled with 500 nM of FITC-conjugated Human Annexin V for affinity and (1:50 dilution) of Alexa Flour 647-Chicken anti-Human IgG for monitoring IgG expression. To determine appropriate settings for sorting, control JUDE-1 cells expressing only NlpA-ZZ protein were double-labeled with 500 nM of FITC-conjugated Human Annexin V and Alexa Flour 647-Chicken anti-Human IgG and analyzed for fluorescent emission signals on an ARIA™ droplet deflection flow cytometer carrying a 488-nm and a 633 nm Argon lasers for excitation. The control population was used to set the appropriate double-negative quadrant (FIG. 18A). For library sorting a sorting gate in the double-positive quadrant corresponding to approximately 5% of the total population was set (FIG. 18B). In round one a total of $1 \times 10^9$ cells were selected based on improved fluorescence in the fluorescein and Alexa Flour 647 emission spectrum detecting through a 530/40 and a 670/20 band-pass filters, recovering $5 \times 10^7$ events at 20,000 $s^{-1}$. The collected speheroplasts were immediately resorted on the flow cytometer using the same collection gate for the initial sort, recovering $5 \times 10^6$ events (10%) at 200 $s^{-1}$. Subsequently, a DNA fragment corresponding to the $V\kappa$-$C\kappa$-$V_H$ sequence of the IgG gene was rescued by PCR, recloned into pMAZ360-IgG vector and transformed into fresh E. coli JUDE-1-NlpA-ZZ cells. The resulting clones were grown, induced for expression of IgG and subjected to four additional rounds of sorting under the following conditions: sort 2; $1 \times 10^8/5 \times 10^7$ (5%) at 20,000 $s^{-1}$; resort 2 $1 \times 10^7/1 \times 10^6$ (10%) at 200 $s^{-1}$; sort 3; $5 \times 10^7/1 \times 10^6$ (2%) at 20,000 $s^{-1}$; resort 3 $1 \times 10^6/5 \times 10^4$ (5%) at 200 $s^{-1}$; sort 4; $5 \times 10^7/1 \times 10^6$ (2%) at 20,000 $s^{-1}$; resort 4 $1 \times 10^6/5 \times 10^4$ (5%) at 200 $s^{-1}$; sort 5; $5 \times 10^7/1 \times 10^6$ (2%) at 20,000 $s^{-1}$; resort 5 $1 \times 10^6/5 \times 10^4$ (5%) at 200 $s^{-1}$.

Following five rounds of FACS sorting, randomly single selected clones were grown in 96-well plates, induced for expression of soluble IgG antibodies and analyzed for direct binding to Human Annexin V antigen in ELISA using the same conditions described in Example 6C. Sequence alignment of positive clones that confirmed the highest ELISA signal revealed four unique sequences (Table 6).

Example 14

Characterization of Annexin V Antibodies

Soluble cell extract of the individual clones was analyzed for antigen dissociation kinetics using Surface Plasmon Resonance (SPR) analysis by direct binding to Human Annexin V-immobilized chip. Briefly, for small scale production of soluble cell extracts, E. coli JUDE1 cells transformed with pMAZ360-IgG expression vectors were inoculated overnight (ON) at 30° C. in Luria broth (LB) medium supplemented with 100 μg/ml ampicillin and 2% (w/v) glucose. The following day, the cultures were diluted into 20 ml of Terrific broth (TB) medium supplemented with 100 μg/ml ampicillin and 2% (w/v) glucose to give a starting $A_{600}$ of 0.2 and grown at 30° C. When the cultures reached an $A_{600}$ of 1.0, the cells were pelleted for 10 min at 6000 rpm and resuspended in TB medium supplemented with 100 μg/ml ampicillin and 1 mM isopropyl-1-thio-β-D-galactopyranoside (IPTG). Cells were induced ON at 25° C. for expression of IgG. The following day cells were harvested and pelleted for 10 mM at 6000 rpm. Cell extracts were prepared by resuspension of the pellet in 5 ml of Hepes-buffered saline-EP buffer followed by two cycles of sonication. The extracts were clarified by centrifugation at 12,000 rpm at 4° C. Antigen dissociation rate constants were determined on a BIACORE® 3000 (BIACORE®) instrument essentially as described in Example 7. Varying dilutions of clarified cell extracts in HEPES-buffered saline-EP buffer were injected at a flow rate of 50 μl/min at 25° C. to achieve approximately 200 response units of captured IgGs. Samples were analyzed in duplicate using the BIAevaluation software (BIACORE®) with appropriate subtraction methods. The selected clones exhibited dissociation rates that varied between $1$–$35 \times 10^{-2}$ sec (Table 6).

TABLE 2

List of PCR primers

| Oligonucleotide | Sequence |
|---|---|
| HindIII-Mut-FOR | 5'- GCATAGTGATATCGCGTGCTTGACCTGTGAAGTG -3' (SEQ ID NO: 5) |
| HindIII-Mut-REV | 5'- CACTTCACAGGTCAAGCACGCGATATCACTATGC -3' (SEQ ID NO: 6) |
| CH1-FOR | 5'- TCCTCGGCAAGCTTCAAGGGCCCATCG -3' (SEQ ID NO: 7) |
| CH3-AscI-REV | 5'- CTATGCGGCGCGCCTTATTATTTACCCGGAGACAGGGGGAG -3' (SEQ ID NO: 8) |
| M18.1-VH-NheI-FOR | 5'- GAAATCCCTATTGCCTACGGCAGCCGCTGGATTGTTATTGCTAGCGGCTCAGCCGGCAATGGCGGAGGTCCAAC TGGTTGAATCTG -3' (SEQ ID NO: 9) |
| M18.1-VH-HindIII-REV | 5'- GAAGCTTGCCGAGGAGACGGTGACCAGGG -3' (SEQ ID NO: 10) |
| CK-FOR | 5'- CGTACCACTGCGGCCGCACCATCTGTC -3' (SEQ ID NO: 11) |
| CK-Stop-REV | 5'- GCTTCAACAGGGGAGAGTGCTAATAATATATATATATATATATTCTAGAGAAGGAGATATACATATGAAATCCC TATTGCC -3' (SEQ ID NO: 12) |
| M18.1-VL-NcoI-FOR | 5'- AGCCGGCCATGGCGGATATTCAGATGACACAGTCC -3' (SEQ ID NO: 13) |
| M18.1-VL-Not-REV | 5'- GGCCGCAGTGGTACGTTTTATTTCAACCTTGGTG -3' (SEQ ID NO: 14) |
| 26.10-VH-NheI-FOR | 5'- GTTATTGCTAGCGGCTCAGCCGGCAATGGCGCAGGTGGAGCTGCAGCAGTCTG -3' (SEQ ID NO: 15) |
| 26.10-VH-HindIII-REV | 5'- CCCTTGAAGCTTGCAGAGCTCACAGTAACACTAGCACCATGACC -3' (SEQ ID NO: 16) |
| 26.10-VL-SfiI-FOR | 5'- ATCGCGGCCCAGCCGGCCATGGCGGACATAGTACTGACCCAGTC -3' (SEQ ID NO: 17) |
| 26.10-VL-Not-REV | 5'- GATGGTGCGGCCGCAGTGGCCGATTTGATCTCGAGC -3' (SEQ ID NO: 18) |

TABLE 2-continued

List of PCR primers

| Oligonucleotide | Sequence |
|---|---|
| 5' VL amplifier-FOR | 5'- CGGATAACAATTTCACACAGG -3' (SEQ ID NO: 28) |
| 3' VH amplifier-REV | 5'- AGTTCCACGACACCGTCACCG -3' (SEQ ID NO: 29) |

TABLE 3

Diversity designs for randomizing heavy chain CDRH3

| | YMF10 | N93 | A94 | G95 | T96 | P97 | F98 | E99 | G100 | L100a | R100b | R100c | A100d | D101 | Y102 | Length | Degeneracy | Size |
|---|---|---|---|---|---|---|---|---|---|---|---|---|---|---|---|---|---|---|
| Oligonucleotide | CDRH3-12 | *RMC* | *SSA* | *BNK* | *NNC* | *NVC* | *NWC* | *DRK* | *KVC* | *BHC* | *BVC* | *BVC* | *WTK* | *GMC* | *TAC* | 12 | $8 \times 10^9$ | $6 \times 10^8$ |
| | CDRH3-11 | *RMC* | *SSA* | *BNK* | *NNC* | *NVC* | . | *DRK* | *KVC* | *BHC* | *BVC* | *BVC* | *WTK* | *GMC* | *TAC* | 11 | $1 \times 10^9$ | $4 \times 10^8$ |
| | CDRH3-10 | *RMC* | *SSA* | *BNK* | *NNC* | *NVC* | . | . | *KVC* | *BHC* | *BVC* | *BVC* | *WTK* | *GMC* | *TAC* | 10 | $9 \times 10^7$ | $6 \times 10^8$ |
| | CDRH3-9 | *RMC* | *SSA* | *BNK* | *NNC* | *NVC* | . | . | . | *BHC* | *BVC* | *BVC* | *WTK* | *GMC* | *TAC* | 9 | $1.5 \times 10^7$ | $5 \times 10^8$ |
| | CDRH3-8 | *RMC* | *SSA* | *BNK* | *NNC* | *NVC* | . | . | . | . | *BVC* | *BVC* | *WTK* | *GMC* | *TAC* | 8 | $1.7 \times 10^6$ | $5 \times 10^8$ |
| | CDRH3-7 | *RMC* | *SSA* | *BNK* | *NNC* | *NVC* | . | . | . | . | . | *BVC* | *WTK* | *GMC* | *TAC* | 7 | $1.9 \times 10^5$ | $4 \times 10^8$ |
| Amino acids | | A T N D | R P A G | A T D G Y | T G S Y F A L R Y P V P T L H E Q C | G P Y T D Y N A L R P N D C H I F | F Y L Y D G R V S W H T K N C | E D Y G R S C | A S D Y G A H C | L Y S R G S Y P F D C V | A R G S Y P D C H | A R G S Y P D C H | M F L I | A D | Y | | | |

TABLE 4

Diversity designs for randomizing light chain CDRL3

| | YMF10 | Q89 | Q90 | Y91 | S92 | S93 | Y94 | P95 | L96 | T97 | Length | Degeneracy | Size |
|---|---|---|---|---|---|---|---|---|---|---|---|---|---|
| Oligonucleotide | CDRL3 | *CAG* | *MAK* | *NRC* | *DMC* | *MRC* | *HMC* | *CCT* | *YWC* | *ACG* | 9 | $1.85 \times 10^4$ | $1 \times 10^7$ |
| Amino acids | | Q | Q H N K | Y D S | N N H S G Y D R C | R N S H T S Y A | N S Y P H | P | L F Y H | T | | | |

TABLE 5

Oligonucleotide primers used to create semi-synthetic IgG library

| CDRL3 | GATGGT<u>GCGGCCGC</u>AGTACGTTTAATCTCCAGCTTGGTCCCAGCACCGAACGTGWRAGGGKDGYKGKHGYNMTKCTGACAGAAATAATCTGCCAAGTCTTCAGACTGC (SEQ ID NO: 30) |
|---|---|
| VL-FOR | CGGATAACAATTTCACACAGG (SEQ ID NO: 28) |

TABLE 5-continued

Oligonucleotide primers used to create semi-synthetic IgG library

CDRH3-12  CCCTTGAAGCTTGCTGAGGAGACTGTGAGAGTGGTGCCTTGGCCCCAGTAGKCMAWGBVGBVGDVGBMMYHGWNGBNGNNM
          NVTSSGKYACAGTAATAGACGGCAGTGTCCTC (SEQ ID NO: 31)

CDRH3-11  CCCTTGAAGCTTGCTGAGGAGACTGTGAGAGTGGTGCCTTGGCCCCAGTAGKCMAWGBVGBVGDVGBMMYHGBNGNNMNVT
          SSGKYACAGTAATAGACGGCAGTGTCCTC (SEQ ID NO: 32)

CDRH3-10  CCCTTGAAGCTTGCTGAGGAGACTGTGAGAGTGGTGCCTTGGCCCCAGTAGKCMAWGBVGBVGDVGBMGBNGNNMNVTSSGK
          YACAGTAATAGACGGCAGTGTCCTC (SEQ ID NO: 33)

CDRH3-9   CCCTTGAAGCTTGCTGAGGAGACTGTGAGAGTGGTGCCTTGGCCCCAGTAGKCMAWGBVGBVGDVGBNGNNMNVTSSGKYAC
          AGTAATAGACGGCAGTGTCCTC (SEQ ID NO: 34)

CDRH3-8   CCCTTGAAGCTTGCTGAGGAGACTGTGAGAGTGGTGCCTTGGCCCCAGTAGKCMAWGBVGBVGBNGNNMNVTSSGKYACAGT
          AATAGACGGCAGTGTCCTC (SEQ ID NO: 35)

CDRH3-7   CCCTTGAAGCTTGCTGAGGAGACTGTGAGAGTGGTGCCTTGGCCCCAGTAGKCMAWGBVGBNGNNMNVTSSGKYACAGTAAT
          AGACGGCAGTGTCCTC (SEQ ID NO: 36)

VH-FOR    TGGATAACGCCCTCCAATCGG (SEQ ID NO: 37)

TABLE 6

Dissociation kinetics and amino acid sequences of CDR3s of isolated IgG clones

| Antibody clone | $K_{dis}$ (sec$^{-1}$) | CDR3 $V_\kappa$ | $V_H$ |
|---|---|---|---|
| Parental YMF10 | $1.52 \times 10^{-2}$ | QQYSSYPLT (SEQ ID NO: 38) | GTPFEGLRRADY (SEQ ID NO: 39) |
| E5-3 | $1.04 \times 10^{-2}$ | QNHDHHPHT (SEQ ID NO: 40) | LPPDFRAIAY (SEQ ID NO: 41) |
| D4-2 | $2.04 \times 10^{-2}$ | QNHTSPSHT (SEQ ID NO: 42) | VLYDSSGLAY (SEQ ID NO: 43) |
| F9-2 | $1.52 \times 10^{-1}$ | QNHTHPPLT (SEQ ID NO: 44) | LYSCYYPFAY (SEQ ID NO: 45) |
| A8-2 | $3.52 \times 10^{-1}$ | QQGYHSPHT (SEQ ID NO: 46) | VRLHDFCSLAY (SEQ ID NO: 47) |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,322,783
U.S. Pat. No. 5,538,877
U.S. Pat. No. 5,538,880
U.S. Pat. No. 5,550,318
U.S. Pat. No. 5,563,055
U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,683,195
U.S. Pat. No. 4,683,202
U.S. Pat. No. 4,683,202
U.S. Pat. No. 4,684,611
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,883,750
U.S. Pat. No. 4,938,948
U.S. Pat. No. 4,938,948
U.S. Pat. No. 4,952,500
U.S. Pat. No. 4,988,618
U.S. Pat. No. 4,989,977
U.S. Pat. No. 5,021,236
U.S. Pat. No. 5,160,974
U.S. Pat. No. 5,302,523
U.S. Pat. No. 5,384,253

U.S. Pat. No. 5,464,765
U.S. Pat. No. 5,478,722
U.S. Pat. No. 5,563,055
U.S. Pat. No. 5,567,326
U.S. Pat. No. 5,571,698
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,779,907
U.S. Pat. No. 5,780,279
U.S. Pat. No. 5,780,448
U.S. Pat. No. 5,789,215
U.S. Pat. No. 5,824,520
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,912,148,
U.S. Pat. No. 5,916,776
U.S. Pat. No. 5,916,779
U.S. Pat. No. 5,922,545
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 7,094,571
U.S. Patent Publ. 20030180937
U.S. Patent Publ. 20030219870
U.S. Patent Publ. 20050260736
Abbondanzo et al., *Breast Cancer Res. Treat.*, 16:182(151), 1990.
Ahouse et al., *J. Immunol.*, 151:6076-6088, 1993.
Allen and Seed, *Nucleic Acids Res.*, 16:11824, 1988.
Antibodies: A Laboratory Manual, Cold Spring Harbor Laboratory, 1988
Atherton et al., *Biol. Reprod.*, 32(1):155-171, 1985.
Ausubel et al., In: *Current Protocols in Molecular Biology*, John, Wiley & Sons, Inc, NY, 1994.
Baneyx and Mujacic, *Nat. Biotechnol.*, 22:1399-1408, 2004.
Bellus, *J. Macromol. Sci. Pure Appl. Chem.*, A31(1): 1355-1376, 1994.
Berrier et al., 2000
Bocek and Pecht, *FEBS Lett.*, 331, 86-90, 1993.
Boeke et al., *Mol. Gen. Genet.*, 186, 1982.
Boss et al., *Nucleic Acids Res.*, 12:3791-3806, 1984.
Bukau et al., *J. Bacteriol.*, 163:61, 1985.
Burman et al., *J. Bacteriol.*, 112:1364, 1972.
Cabilly et al., *Proc. Natl. Acad. Sci. USA*, 81:3273-3277, 1984.
Carbonelli et al., *FEMS Microbiol Lett.*, 177:75-82. 1999
Chames et al., *Proc. Natl. Acad. Sci. USA*, 97:7969-7974, 2000.
Chen and Okayama, *Mol. Cell. Biol.*, 7(8):2745-2752, 1987.
Chen et al., *Protein Eng.*, 12:349-356, 1999.
Cocea, *Biotechniques*, 23(5):814-816, 1997.
Collins et al., *Immunogenetics*, 45:440-443, 1997.
Daugherty et al., *Protein Eng.*, 12:613 621, 1999.
de Haard et al., *J. Biol. Chem.*, 274:18218-18230, 1999.
De Jager et al., *Semin. Nucl. Med.*, 23(2):165-179, 1993.
de Kruif et al., *J. Mol. Biol.*, 248, 97-105, 1995.
Decad and Nikaido, *J. Bacteriol.*, 128:325, 1976.
Desai et al., *Cancer Res.*, 58:2417-2425, 1998.
Dholakia et al., *J. Biol. Chem.*, 264(34):20638-20642, 1989.
Doolittle and Ben-Zeev, *Methods Mol Biol*, 109:215-237, 1999.
European Appln. 329 822
Fahnestock et al., *J. Bacteriol.*, 167:870-880, 1986.
Farmer et al., *FEMS Microbiol. Lett.*, 176:11, 1999.
Fechheimer, et al., *Proc Natl. Acad. Sci. USA*, 84:8463-8467, 1987.
Fellouse et al. *J. Mol. Biol.*, 373, 924-40, 2007.
Fraley et al., *Proc. Natl. Acad. Sci. USA*, 76:3348-3352, 1979.
Frohman, In: *PCR Protocols: A Guide To Methods And Applications*, Academic Press, N.Y., 1990.
GB Appln. 2 202 328
Gennity and Inouye, *J. Bacteriol.*, 174(7):2095, 1992.
Georgiou, *Adv. Protein Chem.*, 55:293-315, 2000.
Gomi et al., *J. Immunol.*, 144:4046-4052, 1990.
Gopal, *Mol. Cell. Biol.*, 5:1188-1190, 1985.
Graham and Van Der Eb, *Virology*, 52:456-467, 1973.
Griffith, *EMBO J.*, 13:3245-3260, 1994.
Griffiths and Duncan, *Curr. Opin. Biotechnol.*, 9:102-108, 1998.
Griffiths et al., *Embo.* 1, 13:3245-3260, 1994.
Gulbis and Galand, *Hum. Pathol.*, 24(12):1271-1285, 1993.
Halloran et al., *J. Immunol.*, 153:2631-2641, 1994.
Harland and Weintraub, *J. Cell Biol.*,101(3):1094-1099, 1985.
Harvey et al., *J. Immunol. Methods*, 308:43-52, 2006.
Harvey et al., *Proc. Natl. Acad. Sci. USA*, 101, 9193-9198, 2004.
Harvey et al., *Proc. Natl. Acad. Sci. USA*, 101:9193-9198, 2004.
Hayhurst et al., *J. Immunol. Methods*, 276:185-196, 2003.
Hobot et al., *J. Bacteriol.*, 160:143, 1984.
Hoet et al., *Nat. Biotechnol.*, 23:344-348, 2005.
Hoogenboom and Winter, *J. Mol. Biol.*, 227:381-388, 1992.
Hoogenboom et al., *Immunotechnology.*, 4:1-20, 1998.
Hoogenboom, *Methods Mol. Biol.*, 178:1-37, 2002.
Hoogenboom, *Nat. Biotechnol.*, 23:1105-1116, 2005.
Huie et al., *Proc. Natl. Acad. Sci. USA*, 98:2682-2687, 2001.
Innis et al., *Proc. Natl. Acad. Sci. USA*, 85(24):9436-9440, 1988.
Irvin et al., *J. Bacteriol.*, 145:1397, 1981.
Jouenne and Junter, FEMS Microbiol. Lett., 56:313, 1990.
Kabat et al, *Sequences of Proteins of Immunological Interest: 5th Edition*", U.S. Department of Health and Human Services, U.S. Government Printing Office, 1991.
Kaeppler et al., *Plant Cell Reports*, 9:415-418, 1990.
Kaneda et al., *Science*, 243:375-378, 1989.
Kato et al, *J. Biol. Chem.*, 266:3361-3364, 1991.
Khatoon et al., *Ann. Neurol.*, 26(2):210-215, 1989.
King et al., 1989
Kipriyanov and Little, *Mol. Biotechnol.*, 12:173-201, 1999.
Kjaer et al., *FEBS Lett.*, 431:448-452, 1998.
Knappik et al., *J. Mol. Biol.*, 296:57-86, 2000.
Knight et al., *Mol. Immunol.*, 32:1271-1281, 1995.
Kohler and Milstein, *Nature*, 256:495-497, 1975.
Kramer et al., *Eur. J. Immunol.*, 35:2131-2145, 2005.

Krebber et al., *J. Immunol. Methods*, 201:35-55, 1997.
Kuroda et al., *Lancet.*, 357:1225-1240, 2001.
Kwoh et al., *Proc. Natl. Acad. Sci. USA*, 86:1173, 1989.
Labischinski et al., *J. Bacteriol.*, 162:9, 1985.
Levenson et al., 1998,
Lipovsek and Pluckthun, *J. Immunol. Methods*, 290:51-67, 2004.
Lu et al., *J. Biol. Chem.*, 278:43496-507, 2003.
Maniatis, et al., Molecular Cloning, A Laboratory Manual, Cold Spring Harbor Press, Cold Spring Harbor, N.Y., 1988.
Marciano et al., *Science*, 284:1516, 1999.
Marks et al., *Bio/Technol.*, 10:779-783, 1992.
Masuda et al., *Proc Natl. Acad. Sci. USA*, 99(11):7390, 2002.
Milenic et al., *Cancer Res.*, 51:6363-6371, 1991.
Morrison et al., *Proc. Natl. Acad. Sci. USA*, 81(21):6851-6855, 1984.
Moulard et al., *Proc. Natl. Acad. Sci. USA*, 99:6913-6918, 2002.
Munson and Pollard, *Anal. Biochem.*, 107:220, 1980.
Nicolau and Sene, *Biochim. Biophys. Acta*, 721:185-190, 1982.
Nicolau et al., *Methods Enzymol.*, 149:157-176, 1987.
Nikaido and Nakae, *Adv. Microb. Physiol.*, 20:163, 1979.
Nikaido and Vaara, *Microbiol. Rev.*, 49:1, 1985.
Nikaido, *J. Bacteriology*, 178(20):5853-5859, 1996.
Nilsson et al., *Protein Eng.*, 1:107-113, 1987.
Nilsson et al., *Protein Eng.*, 1:107-113, 1987.
Ohara et al., *Proc. Natl. Acad. Sci. USA*, 86:5673-5677, 1989.
Oliver, *Periplasm*, 88-103, 1996.
Olsson et al., *Eur. J. Biochem.*, 168:319-324, 1987.
Omirulleh et al., *Plant Mol. Biol.*, 21(3):415-428, 1993.
Orlandi et al., *Proc. Natl. Acad. Sci. USA*, 86:3833-3837, 1989.
Owens and Haley, *Biochem. Biophys. Res. Commun.*, 142(3):964-971, 1987.
Painbeni et al., *Proc Natl. Acad. Sci. USA*, 94:6712, 1997.
Pavlou and Belsey, *Eur. J. Pharm. Biopharm.*, 59:389-396, 2005.
PCT Appln. PCT/US87/00880
PCT Appln. PCT/US89/01025
PCT Appln. WO 88/10315,
PCT Appln. WO 89/06700
PCT Appln. WO 90/07641
PCT Appln. WO 93/06213
PCT Appln. WO 94/09699
PCT Appln. WO 95/06128
Pini and Bracci, *Curr. Protein Pept. Sci.*, 1:155-169, 2000.
Potrykus et al., *Mol. Gen. Genet.*, 199(2):169-177, 1985.
Potter and Haley, *Methods Enzymol*, 91:613-633, 1983.
Pugsley, *Microbiol. Rev.*, 57:50 108, 1993/Rao
Rao and Torriani, *J. Bacteriol.*, 170, 5216, 1988.
Ravetch and Perussia et al., *J. Exp. Med.*, 170:481-497, 1989.
Ravetch et al., *Science*, 234:718-725, 1986.
Rippe, et al., *Mol. Cell. Biol.*, 10:689-695, 1990.
Ruhlmann et al., *FEBS Lett.*, 235:262-266, 1988.
Sambrook et al., In: *Molecular cloning: a laboratory manual*, $2^{nd}$ Ed., Cold Spring Harbor Laboratory Press, Cold Spring Harbor, N.Y., 1989.
Schier et al., *J. Mol. Biol.*, 263:551-567, 1996.
Scott, and Smith, *Science*, 249:386-390, 1990.
Sears et al., *J. Immunol.*, 144:371-378, 1990.
Shuttleworth et al., *Gene*, 58:283-295, 1987.
Simister and Mostov, *Nature*, 337:184-187, 1989.
Simmons et al., *J. Immunol. Methods*, 263:133-147, 2000.
Smith and Scott, *Methods Enzymol.*, 217:228-257, 1993.
Stenberg et al., *Mol. Microbiol.*, 6:1185-1194, 1992.
Stuart et al., *Embo J.*, 8:3657-3666, 1989.
Stuart et al., *J. Exp. Med.*, 166:1668-1684, 1987.
Thorstenson et al., 1997
Tominaga et al., *Biochem. Biophys. Res. Commun.*, 168:683-689, 1990.
Uhlen et al., *J. Biol. Chem.*, 259:1695-702, 1984.
Van Wielink and Duine, *Trends Biochem Sci.*, 15:136, 1990.
Vargas-Madrazo et al., *J. Mol. Biol.*, 246, 74-81, 1995.
Vaughan et al., *Nat. Biotechnol.*, 14:309-314, 1996.
Wada et al., *J. Biol. Chem.*, 274:17353-17357, 1999.
Walker et al., *Nucleic Acids Res.*, 20(7):1691-1696, 1992.
Waterhouse et al., *Nucl. Acids Res.*, 21:2265-2266, 1993.
Wong et al., *Gene*, 10:87-94, 1980.
Worn and Pluckthun, *J. Mol. Biol.*, 305:989-1010, 2001.
Yacoby et al., *Antimicrob. Agents Chemother.*, 50:2087-2097, 2006.
Yacoby et al., *Antimicrob. Agents Chemother.*, 50:2087-2097, 2006.
Yakushi, *J. Bacteriology*, 179(9):2857 1997.
Yakushi, *Nat. Cell. Biol.*, 2:212 218, 2000.
Yamaguchi, *Cell*, 53:423 432, 1988.
Yamaguchi, *Cell*, 53:423 432, 1988.
Yang et al., *J. Mol. Biol.*, 254:392-403, 1995.
Yu, *J. Biol. Chem.*, 261:2284 22, 1986.
Zeger et al., *Proc. Natl. Acad. Sci. USA*, 87:3425-3429, 1990.
Zhang et al., *Immunogenetics*, 39:423-437, 1994.
Zhang et al., *Microbiology*, 144(Pt 4):985-991, 1998.

What is claimed is:

1. A bacteriophage population, wherein members of the population comprise:
   a) at least one coat protein fused to an antibody-binding domain that has the ability to bind to an Fc domain of an antibody, wherein the antibody-binding domain is displayed on the surface of the bacteriophage particle;
   b) a nucleic acid sequence encoding an antibody having at least an Fc domain and a variable domain wherein the nucleic acid sequence is packaged in the bacteriophage; and
   c) an antibody encoded by the nucleic acid sequence, wherein the antibody is not fused to a coat protein but is bound to the surface of the bacteriophage by virtue of the Fc domain of the antibody being bound to the antibody-binding domain; and wherein the population of bacteriophages collectively comprises a plurality of nucleic acid sequences encoding a plurality of distinct antibodies.

2. The bacteriophage population of claim 1, wherein the immunoglobulin light chain (L) and heavy (H) chain are encoded by a dicistronic expression cassette.

3. The bacteriophage of claim 1, wherein the antibody is an IgG antibody.

4. The bacteriophage of claim 3, wherein the IgG antibody is an IgG1.

5. The bacteriophage of claim 1, wherein the bacteriophage is a bacteriophage M13.

6. The bacteriophage of claim 5, wherein the antibody-binding domain is fused to the p3 coat protein.

7. The bacteriophage of claim 1, wherein the antibody-binding domain binds to the Fc of an IgG antibody.

8. The bacteriophage of claim 1, wherein antibody-binding domain comprises a mammalian, bacterial or synthetic Fc binding domain.

9. The bacteriophage of claim 8, wherein the bacterial Fc binding domain is an S. aureus protein A or protein G domain.

10. The bacteriophage of claim 8, wherein the synthetic Fc binding domain is ZZ polypeptide.

* * * * *

SEQUENCE LISTING

<160> NUMBER OF SEQ ID NOS: 47

<210> SEQ ID NO 1
<211> LENGTH: 6148
<212> TYPE: DNA
<213> ORGANISM: Artificial
<220> FEATURE:
<223> OTHER INFORMATION: Plasmid

<400> SEQUENCE: 1

```
acccgccacc atcgaatggc gcaaaacctt tcgcggtatg gcatgatagc gcccggaaga      60
gagtcaattc agggtggtga atgtgaaacc agtaacgtta tacgatgtcg cagagtatgc     120
cggtgtctct tatcagaccg tttcccgcgt ggtgaaccag gccagccacg tttctgcgaa     180
aacgcgggaa aaagtggaag cggcgatggc ggagctgaat tacattccca accgcgtggc     240
```

```
acaacaactg gcgggcaaac agtcgttgct gattggcgtt gccacctcca gtctggccct      300
gcacgcgccg tcgcaaattg tcgcggcgat taaatctcgc gccgatcaac tgggtgccag      360
cgtggtggtg tcgatggtag aacgaagcgg cgtcgaagcc tgtaaagcgg cggtgcacaa      420
tcttctcgcg caacgcgtca gtgggctgat cattaactat ccgctggatg accaggatgc      480
cattgctgtg gaagctgcct gcactaatgt tccggcgtta tttcttgatg tctctgacca      540
gacacccatc aacagtatta ttttctccca tgaagacggt acgcgactgg gcgtggagca      600
tctggtcgca ttgggtcacc agcaaatcgc gctgttagcg ggcccattaa gttctgtctc      660
ggcgcgtctg cgtctggctg gctggcataa atatctcact cgcaatcaaa ttcagccgat      720
agcggaacgg gaaggcgact ggagtgccat gtccggtttt caacaaacca tgcaaatgct      780
gaatgagggc atcgttccca ctgcgatgct ggttgccaac gatcagatgg cgctgggcgc      840
aatgcgcgcc attaccgagt ccgggctgcg cgttggtgcg gacatctcgg tagtgggata      900
cgacgatacc gaagacagct catgttatat cccgccgtta accaccatca aacaggattt      960
tcgcctgctg ggcaaaccag cgtggaccg cttgctgcaa ctctctcagg gccaggcggt     1020
gaagggcaat cagctgttgc ccgtctcact ggtgaaaaga aaaccaccc tggcgcccaa     1080 tacgcaaacc gcctctcccc gcgcgttggc cgattcatta atgcagctgg cacgacaggt     1140
ttcccgactg gaaagcgggc agtgagcggt acccgataaa agcggcttcc tgacaggagg     1200
ccgttttgtt ttgcagccca cctcaacgca attaatgtga gttagctcac tcattaggca     1260
ccccaggctt tacactttat gcttccggct cgtatgttgt gtggaattgt gagcggataa     1320
caatttcaca caggaaacag ctatgaccat gattacgaat ttctagagaa ggagatatac     1380
atatgaaatc cctattgcct acggcagccg ctggattgtt attctcgcg gcccagccgg     1440 ccatggcgga tattcagatg acacagtccc cgtcctccct gtctgcctct gttggagaca     1500
gagtcaccgt cacctgcagg gcaagtcagg gcattaggaa ttatttaaac tggtatcagc     1560
agaaaccagg taaagctcct aaattcctga tctactacac atcaagatta ctgccgggag     1620
tcccatcaag gttcagtggc agtgggtctg gaacagatta taccctcacc attaactccc     1680
tggagcaaga agatattgct acttactact gccaacaggg taatacgcct ccgtggacgt     1740
tcggtcaggg caccaaggtt gaaataaaac gtaccactgc ggccgcacca tctgtcttca     1800
tcttcccgcc atctgatgag cagttgaaat ctggaactgc ctctgttgtg tgcctgctga     1860
ataacttcta tcccagagag gccaaagtac agtggaaggt ggataacgcc ctccaatcgg     1920
gtaactccca ggagagtgtc acagagcagg acagcaagga cagcacctac agcctcagca     1980
gcaccctgac gctgagcaaa gcagactacg agaaacacaa agtctacgcc tgcgaagtca     2040
cccatcaggg cctgagttcg cccgtcacaa agagcttcaa caggggagag tgctaataat     2100
atatatatat atatattcta gagaaggaga tatacatatg aaatccctat tgcctacggc     2160
agccgctgga ttgttattgc tagcggctca gccggcaatg gcggaggtcc aactggttga     2220
atctggaggt ggtctggtgc agcctggggg ttcactgcgc ctgtcctgcg ctgattctgg     2280
ctacgcattc aatagctctt ggatgaactg ggtgcgccag gctcctggaa aaggtcttga     2340
gtgggttgga cggatttatc ctggagatgg agatagtaac tacaatggga agttcgaggg     2400
ccgcgccata atctccgcag acaaatcctc agcacagcc tacctgcaga tgaacagcct     2460
gcgcgctgaa gacactgcgg tctattactg tgcaagatcg gggttactac gttatgctat     2520
ggactactgg ggtcaaggaa ccctggtcac cgtctcctcg gcaagcttca agggcccatc     2580
ggtcttcccc ctggcaccct cctccaagag cacctctggg ggcacagcgg ccctgggctg     2640
```

```
cctggtcaag gactacttcc ccgaaccggt gacggtgtcg tggaactcag gcgccctgac    2700
cagcggcgtg cacaccttcc cggctgtcct acagtcctca ggactctact ccctcagcag    2760
cgtggtgacc gtgccctcca gcagcttggg cacccagacc tacatctgca acgtgaatca    2820
caagcccagc aacaccaagg tggacaagaa agttgagccc aaatcttgtg acaaaactca    2880
cacacgccca ccgtgcccag cacctgaact cctgggggga ccgtcagtct tcctcttccc    2940
cccaaaaccc aaggacaccc tcatgatctc ccggacccct gaggtcacat gcgtggtggt    3000
ggacgtgagc cacgaagacc ctgaggtcaa gttcaactgg tacgtggacg gcgtggaggt    3060
gcataatgcc aagacaaagc cgcgggagga gcagtacaac agcacgtacc gtgtggtcag    3120
cgtcctcacc gtcctgcacc aggactggct gaatggcaag gagtacaagt gcaaggtctc    3180
caacaaagcc ctcccagccc ccatcgagaa aaccatctcc aaagccaaag gcagccccg    3240 agaaccacag gtgtacaccc tgcccccatc ccgggatgag ctgaccaaga accaggtcag    3300
cctgacctgc ctggtcaaag gcttctatcc cagcgacatc gccgtggagt gggagagcaa    3360
tgggcagccg gagaacaact acaagaccac acctcccgtg ctggactccg acggctcctt    3420
cttcctctac agcaagctca ccgtggacaa gagcaggtgg cagcagggga acgtcttctc    3480
atgctccgtg atgcatgagg ctctgcacaa ccactacacg cagaagagcc tccccctgtc    3540
tccgggtaaa taataaggcg cgccgcatag tgatatcgcg tgcttgacct gtgaagtgaa    3600
aaatggcgca cattgtgcga catttttttt gtctgccgtt taccgctact gcgtcacgga    3660
tccccacgcg ccctgtagcg cgcattaag cgcggcgggt gtggtggtta cgcgcagcgt    3720
gaccgctaca cttgccagcg ccctagcgcc cgctcctttc gctttcttcc cttcctttct    3780
cgccacgttc gccggctttc cccgtcaagc tctaaatcgg gcatcccttt agggttccg    3840 atttagtgct ttacggcacc tcgacccaaa aaacttgat tagggtgatg gttcacgtag    3900
tgggccatcg ccctgataga cggttttcg ccctttgacg ttggagtcca cgttctttaa    3960
tagtggactc ttgttccaaa ctggaacaac actcaaccct atctcggtct attctttga    4020 tttataaggg attttgccga tttcggccta ttggttaaaa atgagctga tttaacaaaa    4080 atttaacgcg aattttaaca aaatattaac gtttacaatt tcaggtggca cttttcgggg    4140
aaatgtgcgc ggaacccctta tttgtttatt tttctaaata cattcaaata tgtatccgct    4200
catgtcgaga cgttgggtga ggttccaact ttcaccataa tgaaataaga tcactaccgg    4260
gcgtattttt tgagttatcg agattttcag gagctaagga aatttaaatg agtattcaac    4320
atttccgtgt cgcccttatt cccttttttg cggcatttg ccttcctgtt tttgctcacc    4380
cagaaacgct ggtgaaagta aaagatgctg aagatcagtt gggtgcacga gtgggttaca    4440
tcgaactgga tctcaacagc ggtaagatcc ttgagagttt tcgccccgaa gaacgttttc    4500
caatgatgag cacttttaaa gttctgctat gtggcgcggt attatcccgt gttgacgccg    4560
ggcaagagca actcggtcgc cgcatacact attctcagaa tgacttggtt gagtactcac    4620
cagtcacaga aaagcatctt acggatggca tgacagtaag agaattatgc agtgctgcca    4680
taaccatgag tgataacact gcggccaact tacttctgac aacgatcgga ggaccgaagg    4740
agctaaccgc ttttttgcac aacatggggg atcatgtaac tcgccttgat cgttgggaac    4800
cggagctgaa tgaagccata ccaaacgacg agcgtgacac cacgatgcct gcagcaatgg    4860
caacaacgtt gcgcaaacta ttaactggcg aactacttac tctagcttcc cggcaacaat    4920
taatagactg gatggaggcg gataaagttg caggaccact tctgcgctcg gcccttccgg    4980
ctggctggtt tattgctgat aaatctggag ccggtgagcg tgggtctcgc ggtatcattg    5040
```

```
cagcactggg gccagatggt aagccctccc gtatcgtagt tatctacacg acggggagtc    5100
aggcaactat ggatgaacga aatagacaga tcgctgagat aggtgcctca ctgattaagc    5160
attggtaaat ttaaataggc agttattggt gcccttaaac gcctggtgct acgcctgaat    5220
aagtgataat aagcggatga atggcagaaa ttcgaaagca aattcgaccc ggtcgtcggt    5280
tcagggcagg tcgttaaat agccgcttat gtctattgct ggtttaccgg tttattgact    5340
accggaagca gtgtgaccgt gtgcttctca aatgcctgag gccagtttgc tcaggctctc    5400
cccgtggagg taataattgc tcgacatgac caaaatccct taacgtgagt tttcgttcca    5460
ctgagcgtca gaccccgtag aaaagatcaa aggatcttct tgagatcctt ttttttctgcg    5520 cgtaatctgc tgcttgcaaa caaaaaaacc accgctacca gcggtggttt gtttgccgga    5580
tcaagagcta ccaactcttt ttccgaaggt aactggcttc agcagagcgc agataccaaa    5640
tactgtcctt ctagtgtagc cgtagttagg ccaccacttc aagaactctg tagcaccgcc    5700
tacatacctc gctctgctaa tcctgttacc agtggctgct gccagtggcg ataagtcgtg    5760
tcttaccggg ttggactcaa gacgatagtt accggataag gcgcagcggt cgggctgaac    5820
ggggggttcg tgcacacagc ccagcttgga gcgaacgacc tacaccgaac tgagatacct    5880
acagcgtgag ctatgagaaa gcgccacgct tcccgaaggg agaaaggcgg acaggtatcc    5940
ggtaagcggc agggtcggaa caggagacgc acgagggga cttccagggg gaaacgcctg    6000
gtatctttat agtcctgtcg ggtttcgcca cctctgactt gagcgtcgat ttttgtgatg    6060
ctcgtcaggg gggcggagcc tatggaaaaa cgccagcaac gcggccttt tacggttcct    6120 ggccttttgc tggccttttg ctcacatg                                       6148

<210> SEQ ID NO 2
<211> LENGTH: 6163
<212> TYPE: DNA
<213> ORGANISM: Artificial
<220> FEATURE:
<223> OTHER INFORMATION: Plasmid

<400> SEQUENCE: 2
acccgccacc atcgaatggc gcaaaacctt tcgcggtatg gcatgatagc gcccggaaga      60
gagtcaattc agggtggtga atgtgaaacc agtaacgtta tacgatgtcg cagagtatgc     120
cggtgtctct tatcagaccg tttcccgcgt ggtgaaccag gccagccacg tttctgcgaa     180
aacgcgggaa aaagtggaag cggcgatggc ggagctgaat tacattccca accgcgtggc     240
acaacaactg gcgggcaaac agtcgttgct gattggcgtt gccacctcca gtctggccct     300
gcacgcgccg tcgcaaattg tcgcggcgat taaatctcgc gccgatcaac tgggtgccag     360
cgtggtggtg tcgatggtag aacgaagcgg cgtcgaagcc tgtaaagcgg cggtgcacaa     420
tcttctcgcg caacgcgtca gtgggctgat cattaactat ccgctggatg accaggatgc     480
cattgctgtg gaagctgcct gcactaatgt tccggcgtta tttcttgatg tctctgacca     540
gacacccatc aacagtatta ttttctccca tgaagacggt acgcgactgg gcgtggagca     600
tctggtcgca ttgggtcacc agcaaatcgc gctgttagcg ggcccattaa gttctgtctc     660
ggcgcgtctg cgtctggctg gctggcataa atatctcact cgcaatcaaa ttcagccgat     720
agcggaacgg gaaggcgact ggagtgccat gtccggtttt caacaaacca tgcaaatgct     780
gaatgagggc atcgttccca ctgcgatgct ggttgccaac gatcagatgg cgctgggcgc     840
aatgcgcgcc attaccgagt ccgggctgcg cgttggtgcg gacatctcgg tagtgggata     900
cgacgatacc gaagacagct catgttatat cccgccgtta accaccatca aacaggattt     960
```

```
tcgcctgctg gggcaaacca gcgtggaccg cttgctgcaa ctctctcagg gccaggcggt    1020
gaagggcaat cagctgttgc ccgtctcact ggtgaaaaga aaaaccaccc tggcgcccaa    1080
tacgcaaacc gcctctcccc gcgcgttggc cgattcatta atgcagctgg cacgacaggt    1140
ttcccgactg gaaagcgggc agtgagcggt acccgataaa agcggcttcc tgacaggagg    1200
ccgttttgtt ttgcagccca cctcaacgca attaatgtga gttagctcac tcattaggca    1260
ccccaggctt tacactttat gcttccggct cgtatgttgt gtggaattgt gagcggataa    1320
caatttcaca caggaaacag ctatgaccat gattacgaat tctagagaa ggagatatac     1380 atatgaaatc cctattgcct acggcagccg ctggattgtt attactcgcg gcccagccgg    1440
ccatggcgga catagtactg acccagtctc cagcttcttt ggctgtgtct ctaggacaaa    1500
gggccacgat atcctgccga tccagccaaa gtctcgtaca ttctaatggt aatacttatc    1560
tgaactggta ccaacagaaa ccaggacagc acccaagct tctcatctat aaggtatcca     1620
accgattctc tggagtccct gccaggttca gtggcagtgg gtctgagtca gcttcaccc     1680 tcaccatcga tcctgtggag gaagatgatg ctgcaatata ttactgtagc caaactacgc    1740
atgttccacc cacgttcggc tcggggacca agctcgagat caaatcggcc actgcggccg    1800
caccatctgt cttcatcttc ccgccatctg atgagcagtt gaaatctgga actgcctctg    1860
ttgtgtgcct gctgaataac ttctatccca gagaggccaa agtacagtgg aaggtggata    1920
acgccctcca atcgggtaac tcccaggaga gtgtcacaga gcaggacagc aaggacagca    1980
cctacagcct cagcagcacc ctgacgctga gcaaagcaga ctacgagaaa cacaaagtct    2040
acgcctgcga agtcacccat cagggcctga gttcgcccgt cacaaagagc ttcaacaggg    2100
gagagtgcta ataatatata tatatatata ttctagagaa ggagatatac atatgaaatc    2160
cctattgcct acggcagccg ctggattgtt attgctagcg gctcagccgg caatggcgca    2220
ggtggagctg cagcagtctg gtcctgaatt ggttaaacct ggcgcctctg tgcgcatgtc    2280
ctgcaaatcc tcagggtaca ttttcaccga cttctacatg aattgggttc gccagtctca    2340
tggtaagtct ctagactaca cgggtacat ttcccccatat tctggggtta ccggctacaa     2400
ccagaagttt aaaggtaagg ccaccctac tgtcgacaaa tcttcctcaa ctgcttacat      2460
ggagctgcgt tctttgacct ctgaggactc cgcggtatac tattgcgccg gctcctctgg    2520
taacaaatgg gccatggatt attggggtca tggtgctagt gttactgtga gctctgcaag    2580
cttcaagggc ccatcggtct tccccctggc accctcctcc aagagcacct ctgggggcac    2640
agcggccctg ggctgcctgg tcaaggacta cttccccgaa ccggtgacgg tgtcgtggaa    2700
ctcaggcgcc ctgaccagcg gcgtgcacac cttcccggct gtcctacagt cctcaggact    2760
ctactccctc agcagcgtgg tgaccgtgcc ctccagcagc ttgggcaccc agacctacat    2820
ctgcaacgtg aatcacaagc ccagcaacac caaggtggac aagaaagttg agcccaaatc    2880
ttgtgacaaa actcacacac gcccaccgtg cccagcacct gaactcctgg ggggaccgtc    2940
agtcttcctc ttccccccaa aacccaagga caccctcatg atctcccgga cccctgaggt    3000
cacatgcgtg gtggtggacg tgagccacga agaccctgag gtcaagttca actggtacgt    3060
ggacggcgtg gaggtgcata atgccaagac aaagccgcgg gaggagcagt acaacagcac    3120
gtaccgtgtg gtcagcgtcc tcaccgtcct gcaccaggac tggctgaatg gcaaggagta    3180
caagtgcaag gtctccaaca aagccctccc agccccatc gagaaaacca tctccaaagc     3240
caaagggcag ccccgagaac cacaggtgta caccctgccc ccatcccggg atgagctgac    3300
caagaaccag gtcagcctga cctgcctggt caaaggcttc tatcccagcg acatcgccgt    3360
```

```
ggagtgggag agcaatgggc agccggagaa caactacaag accacacctc ccgtgctgga    3420
ctccgacggc tccttcttcc tctacagcaa gctcaccgtg acaagagca ggtggcagca     3480 ggggaacgtc ttctcatgct ccgtgatgca tgaggctctg cacaaccact acacgcagaa    3540
gagcctcccc ctgtctccgg gtaaataata aggcgcgccg catagtgata tcgcgtgctt    3600
gacctgtgaa gtgaaaaatg gcgcacattg tgcgacattt tttttgtctg ccgtttaccg    3660
ctactgcgtc acggatcccc acgcgccctg tagcggcgca ttaagcgcgg cgggtgtggt    3720
ggttacgcgc agcgtgaccg ctacacttgc cagcgcccta cgcccgctc ctttcgcttt     3780 cttcccttcc tttctcgcca cgttcgccgg ctttccccgt caagctctaa atcggggcat    3840 cccctttaggg ttccgattta gtgctttacg gcacctcgac cccaaaaaac ttgattaggg   3900
tgatggttca cgtagtgggc catcgccctg atagacggtt tttcgccctt tgacgttgga    3960
gtccacgttc tttaatagtg gactcttgtt ccaaactgga acaacactca acctatctc    4020 ggtctattct tttgatttat aagggatttt gccgatttcg gcctattggt taaaaaatga    4080
gctgatttaa caaaaattta acgcgaattt aacaaaata ttaacgttta caatttcagg    4140
tggcactttt cggggaaatg tgcgcggaac ccctatttgt ttatttttct aaatacattc    4200
aaatatgtat ccgctcatgt cgagacgttg ggtgaggttc caactttcac cataatgaaa    4260
taagatcact accgggcgta ttttttgagt tatcgagatt ttcaggagct aaggaaattt    4320
aaatgagtat tcaacatttc cgtgtcgccc ttattccctt ttttgcggca ttttgccttc    4380 ctgttttttgc tcacccagaa acgctggtga agtaaaaga tgctgaagat cagttgggtg    4440
cacgagtggg ttacatcgaa ctggatctca acagcggtaa gatccttgag agttttcgcc    4500
ccgaagaacg ttttccaatg atgagcactt ttaaagttct gctatgtggc gcggtattat    4560
cccgtgttga cgccgggcaa gagcaactcg gtcgccgcat acactattct cagaatgact    4620
tggttgagta ctcaccagtc acagaaaagc atcttacgga tggcatgaca gtaagagaat    4680
tatgcagtgc tgccataacc atgagtgata acactgcggc caacttactt ctgacaacga    4740
tcggaggacc gaaggagcta accgcttttt tgcacaacat ggggatcat gtaactcgcc     4800 ttgatcgttg ggaaccggag ctgaatgaag ccataccaaa cgacgagcgt gacaccacga    4860
tgcctgcagc aatggcaaca acgttgcgca aactattaac tggcgaacta cttactctag    4920
cttcccggca acaattaata gactggatgg aggcggataa agttgcagga ccacttctgc    4980
gctcggccct tccggctggc tggtttattg ctgataaatc tggagccggt gagcgtgggt    5040
ctcgcggtat cattgcagca ctggggccag atggtaagcc ctcccgtatc gtagttatct    5100
acacgacggg gagtcaggca actatggatg aacgaaatag acagatcgct gagataggtg    5160
cctcactgat taagcattgg taaattaaa taggcagtta ttggtgccct taaacgcctg     5220
gtgctacgcc tgaataagtg ataataagcg gatgaatggc agaaattcga agcaaattc     5280 gacccggtcg tcggttcagg gcagggtcgt taaatagccg cttatgtcta ttgctggttt    5340
accggtttat tgactaccgg aagcagtgtg accgtgtgct tctcaaatgc ctgaggccag    5400
tttgctcagg ctctccccgt ggaggtaata attgctcgac atgaccaaaa tcccttaacg    5460
tgagttttcg ttccactgag cgtcagaccc cgtagaaaag atcaaggat cttcttgaga     5520 tccttttttt ctgcgcgtaa tctgctgctt gcaaacaaaa aaaccaccgc taccagcggt    5580
ggtttgtttg ccggatcaag agctaccaac tcttttccg aaggtaactg gcttcagcag     5640
agcgcagata ccaaatactg tccttctagt gtagccgtag ttaggccacc acttcaagaa    5700
ctctgtagca ccgcctacat acctcgctct gctaatcctg ttaccagtgg ctgctgccag    5760
```

```
tggcgataag tcgtgtctta ccgggttgga ctcaagacga tagttaccgg ataaggcgca      5820
gcggtcgggc tgaacggggg gttcgtgcac acagcccagc ttggagcgaa cgacctacac      5880
cgaactgaga tacctacagc gtgagctatg agaaagcgcc acgcttcccg aagggagaaa      5940
ggcggacagg tatccggtaa gcggcagggt cggaacagga gagcgcacga gggagcttcc      6000 aggggggaaac gcctggtatc tttatagtcc tgtcgggttt cgccacctct gacttgagcg     6060 tcgattttg tgatgctcgt cagggggggcg gagcctatgg aaaaacgcca gcaacgcggc      6120 cttttttacgg ttcctggcct tttgctggcc ttttgctcac atg                      6163
```

<210> SEQ ID NO 3
<211> LENGTH: 5896
<212> TYPE: DNA
<213> ORGANISM: Artificial
<220> FEATURE:
<223> OTHER INFORMATION: Plasmid

<400> SEQUENCE: 3

```
gcaaactatt aactggcgaa ctacttactc tagcttcccg gcaacaatta atagactgga       60
tggaggcgga taaagttgca ggaccacttc tgcgctcggc ccttccggct ggctggttta      120
ttgctgataa atctggagcc ggtgagcgtg gtctcgcgg tatcattgca gcactggggc       180
cagatggtaa gccctcccgt atcgtagtta tctacacgac ggggagtcag gcaactatgg      240
atgaacgaaa tagacagatc gctgagatag gtgcctcact gattaagcat tggtaactgt      300
cagaccaagt ttactcatat atactttaga ttgatttacg cgccctgtag cggcgcatta      360
agcgcggcgg gtgtggtggt tacgcgcagc gtgaccgcta cacttgccag cgccctagcg      420
cccgctcctt tcgctttctt cccttccttt ctcgccacgt tcgccggctt tccccgtcaa      480
gctctaaatc gggggctccc tttagggttc cgatttagtg ctttacggca cctcgacccc      540
aaaaaacttg atttgggtga tggttcacgt agtgggccat cgccctgata gacggttttt      600
cgccctttga cgttggagtc cacgttcttt aatagtggac tcttgttcca aacttgaaca      660
acactcaacc ctatctcggg ctattctttt gatttataag gattttgcc gatttcggcc       720 tattggttaa aaaatgagct gatttaacaa aaatttaacg cgaattttaa caaaatatta     780
acgtttacaa tttaaaagga tctaggtgaa gatcctttt gataatctca tgaccaaaat       840
cccttaacgt gagttttcgt tccactgagc gtcagacccc gtagaaaaga tcaaaggatc      900
ttcttgagat cctttttttc tgcgcgtaat ctgctgcttg caaacaaaaa aaccaccgct      960
accagcggtg gtttgtttgc cggatcaaga gctaccaact ctttttccga aggtaactgg     1020
cttcagcaga gcgcagatac caaatactgt ccttctagtg tagccgtagt taggccacca     1080
cttcaagaac tctgtagcac cgcctacata cctcgctctg ctaatcctgt taccagtcag     1140
gcatttgaga agcacacggt cacactgctt ccggtagtca ataaaccggt aaaccagcaa     1200
tagacataag cggctatttta acgaccctgc cctgaaccga cgaccgggtc gaatttgctt    1260
tcgaatttct gccattcatc cgcttattat cacttattca ggcgtagcac caggcgttta    1320
agggcaccaa taactgcctt aaaaaaatta cgccccgccc tgccactcat cgcagtactg     1380
ttgtaattca ttaagcattc tgccgacatg gaagccatca cagacggcat gatgaacctg     1440
aatcgccagc ggcatcagca ccttgtcgcc ttgcgtataa tatttgccca tggtgaaaac    1500
gggggcgaag aagttgtcca tattggccac gtttaaatca aaactggtga actcacccca     1560
gggattggct gagacgaaaa acatattctc aataaaccct ttagggaaat aggccaggtt    1620
ttcaccgtaa cacgccacat cttgcgaata tatgtgtaga aactgccgga aatcgtcgtg    1680
```

```
gtattcactc cagagcgatg aaaacgtttc agtttgctca tggaaaacgg tgtaacaagg    1740
gtgaacacta tcccatatca ccagctcacc gtctttcatt gccatacgga attccggatg    1800
agcattcatc aggcgggcaa gaatgtgaat aaaggccgga taaaacttgt gcttattttt    1860
ctttacggtc tttaaaaagg ccgtaatatc cagctgaacg gtctggttat aggtacattg    1920
agcaactgac tgaaatgcct caaaatgttc tttacgatgc cattgggata tatcaacggt    1980
ggtatatcca gtgatttttt tctccatttt agcttcctta gctcctgaaa atctcgataa    2040
ctcaaaaaat acgcccggta gtgatcttat ttcattatgg tgaaagttgg aacctcttac    2100
gtgccgatca acgtctcatt ttcgccaaaa gttgcccag gcttccgg tatcaacagg      2160 gacaccagga tttatttatt ctgcgaagtg atcttccgtc acaggtattt attcggcgca    2220
aagtgcgtcg ggtgatgctg ccaacttact gatttagtgt atgatggtgt ttttgaggtg    2280
ctccagtggc ttctgtttct atcagctgtc cctcctgttc agctactgac ggggtggtgc    2340
gtaacggcaa aagcaccgcc ggacatcagc gctagcggag tgtatactgg cttactatgt    2400
tggcactgat gagggtgtca gtgaagtgct tcatgtggca ggagaaaaaa ggctgcaccg    2460
gtgcgtcagc agaatatgtg atacaggata tattccgctt cctcgctcac tgactcgcta    2520
cgctcggtcg ttcgactgcg gcgagcggaa atggcttacg aacggggcgg agatttcctg    2580
gaagatgcca ggaagatact aacaggg aa gtgagagggc cgcggcaaag ccgttttcc     2640 ataggctccg ccccctgac aagcatcacg aaatctgacg ctcaaatcag tggtggcgaa    2700
acccgacagg actataaaga taccaggcgt ttccccctgg cggctccctc gtgcgctctc    2760
ctgttcctgc ctttcggttt accggtgtca ttccgctgtt atggccgcgt ttgtctcatt    2820
ccacgcctga cactcagttc cgggtaggca gttcgctcca agctggactg tatgcacgaa    2880 cccccgttc agtccgaccg ctgcgcctta ccggtaact atcgtcttga gtccaacccg      2940
gaaagacatg caaaagcacc actggcagca gccactggta attgatttag aggagttagt    3000
cttgaagtca tgcgccggtt aaggctaaac tgaaaggaca gttttggtg actgcgctcc     3060 tccaagccag ttacctcggt tcaaagagtt ggtagctcag agaaccttcg aaaaaccgcc    3120
ctgcaaggcg ttttttcgt tttcagagca agagattacg cgcagaccaa aacgatctca     3180
agaagatcat cttattaatc agataaaata tttgctcatg agcccgaagt ggcgagcccg    3240
atcttcccca tcggtgatgt cggcgatata ggcgccagca accgcacctg tggcgccggt    3300
gatgccggcc acgatgcgtc cggcgtagag gatctgctca tgtttgacag cttatcatcg    3360
atgcataatg tgcctgtcaa atggacgaag cagggattct gcaaaccta tgctactccg     3420 tcaagccgtc aattgtctga ttcgttacca attatgacaa cttgacggct acatcattca    3480 cttttttcttc acaaccggca cggaactcgc tcgggctggc cccggtgcat tttttaaata   3540
cccgcgagaa atagagttga tcgtcaaaac caacattgcg accgacgtg gcgataggca    3600 tccgggtggt gctcaaaagc agcttcgcct ggctgatacg ttggtcctcg cgccagctta    3660
agacgctaat ccctaactgc tggcggaaaa gatgtgacag acgcgacggc gacaagcaaa    3720
catgctgtgc gacgctggcg atatcaaaat tgctgtctgc caggtgatcg ctgatgtact    3780
gacaagcctc gcgtacccga ttatccatcg gtggatggag cgactcgtta atcgcttcca    3840
tgcgccgcag taacaattgc tcaagcagat ttatcgccag cagctccgaa tagcgccctt    3900 cccccttgccc ggcgttaatg atttgcccaa acaggtcgct gaaatgcggc tggtgcgctt    3960 catccggggcg aaagaacccc gtattggcaa atattgacgg ccagttaagc cattcatgcc    4020
agtaggcgcg cggacgaaag taaacccact ggtgatacca ttcgcgagcc tccggatgac    4080
```

```
gaccgtagtg atgaatctct cctggcggga acagcaaaat atcacccggt cggcaaacaa    4140
attctcgtcc ctgatttttc accaccccct gaccgcgaat ggtgagattg agaatataac    4200
ctttcattcc cagcggtcgg tcgataaaaa aatcgagata accgttggcc tcaatcggcg    4260
ttaaacccgc caccagatgg gcattaaacg agtatcccgg cagcagggga tcattttgcg    4320
cttcagccat actttttcata ctcccgccat tcagagaaga aaccaattgt ccatattgca    4380
tcagacattg ccgtcactgc gtcttttact ggctcttctc gctaaccaaa ccggtaaccc    4440
cgcttattaa aagcattctg taacaaagcg ggaccaaagc catgacaaaa acgcgtaaca    4500
aaagtgtcta taatcacggc agaaaagtcc acattgatta tttgcacggc gtcacacttt    4560
gctatgccat agcatttttta tccataagat tagcggatcc tacctgacgc ttttttatcgc    4620 aactctctac tgtttctcca tacccgtttt tttgggctag cgaattcgag ctcgaattct    4680
ctagagaagg agatatacat atgaaactga acacacatca tctacggaca ggggccgcat    4740
tattgctggc cggaattctg ctggcaggtt gcgaccagat tagcagcgag gcccagccgg    4800
ccatggtaga caacaaattc aacaagaac aacaaaacgc gttctatgag atcttacatt    4860
tacctaactt aaacgaagaa caacgaaacg ccttcatcca aagtttaaaa gatgacccaa    4920
gccaaagcgc taaccttttta gcagaagcta aaaagctaaa tgatgctcag gcgccgaaag    4980
tagacaacaa attcaacaaa gaacaacaaa acgcgttcta tgagatctta catttaccta    5040
acttaaacga agaacaacga acgccttca tccaaagttt aaaagatgac ccaagccaaa    5100
gcgctaacct tttagcagaa gctaaaaagc taaatgatgc tcaggcgccg aaagcggccg    5160
cagtcgacca tcatcatcac catcacgggg ccgcagaaca aaaactcatc tcagaagagg    5220
atctgaatgg gcgcgccgca tagtgatatc gcaagcttgg ctgttttggc ggatgagaga    5280
agattttcag cctgatacag attaaatcag aacgcagaag cggtctgata aaacagaatt    5340
tgcctggcgg cagtagcgcg gtggtcccac ctgacccat gccgaactca gaagtgaaac    5400
gccgtagcgc cgatggtagt gtggggtctc cccatgcgag agtagggaac tgccaggcat    5460
caaataaaac gaaaggctca gtcgaaagac tgggcctttc gttttatctg ttgtttgtcg    5520
gtgaacgctc tcctgagtag gacaaatccg ccgggagcgg atttgaacgt tgcgaagcaa    5580
cggcccggag ggtggcgggc aggacgcccg ccataaactg ccaggcatca aattaagcag    5640
aaggccatcc tgacggatgg cctttttgcg tttctacaaa ctcttttgtt tattttttcta    5700 aatacattca aatatgtatc cgctcatgag acaataaccc tgataaatgc ttcaataata    5760
ttgaaaaagg aagagtatga gtattcaaca tttccgtgtc gcccttattc cctttttttgc    5820 ggcattttgc cttcctgttt ttgctcaccc agaaacgctg gtgaaagtaa aagatgctga    5880
agatcagttg ggtgca                                                    5896
```

<210> SEQ ID NO 4
<211> LENGTH: 128
<212> TYPE: PRT
<213> ORGANISM: Artificial
<220> FEATURE:
<223> OTHER INFORMATION: NlpA=zz fusion protein

<400> SEQUENCE: 4

Cys Asp Gln Ser Ser Glu Ala Gln Pro Ala Met Val Asp Asn Lys
1               5                   10                  15

Phe Asn Lys Glu Gln Gln Asn Ala Phe Tyr Glu Ile Leu His Leu Pro
                20                  25                  30

Asn Leu Asn Glu Glu Gln Arg Asn Ala Phe Ile Gln Ser Leu Lys Asp

```
                35                  40                  45
Asp Pro Ser Gln Ser Ala Asn Leu Leu Ala Glu Ala Lys Lys Leu Asn
 50                  55                  60

Asp Ala Gln Ala Pro Lys Val Asp Asn Lys Phe Asn Lys Glu Gln Gln
 65                  70                  75                  80

Asn Ala Phe Tyr Glu Ile Leu His Leu Pro Asn Leu Asn Glu Glu Gln
                 85                  90                  95

Arg Asn Ala Phe Ile Gln Ser Leu Lys Asp Asp Pro Ser Gln Ser Ala
                100                 105                 110

Asn Leu Leu Ala Glu Ala Lys Lys Leu Asn Asp Ala Gln Ala Pro Lys
            115                 120                 125

<210> SEQ ID NO 5
<211> LENGTH: 34
<212> TYPE: DNA
<213> ORGANISM: Artificial
<220> FEATURE:
<223> OTHER INFORMATION: Synthetic primer

<400> SEQUENCE: 5
gcatagtgat atcgcgtgct tgacctgtga agtg                            34

<210> SEQ ID NO 6
<211> LENGTH: 34
<212> TYPE: DNA
<213> ORGANISM: Artificial
<220> FEATURE:
<223> OTHER INFORMATION: Synthetic primer

<400> SEQUENCE: 6
cacttcacag gtcaagcacg cgatatcact atgc                            34

<210> SEQ ID NO 7
<211> LENGTH: 27
<212> TYPE: DNA
<213> ORGANISM: Artificial
<220> FEATURE:
<223> OTHER INFORMATION: Synthetic primer

<400> SEQUENCE: 7
tcctcggcaa gcttcaaggg cccatcg                                    27

<210> SEQ ID NO 8
<211> LENGTH: 41
<212> TYPE: DNA
<213> ORGANISM: Artificial
<220> FEATURE:
<223> OTHER INFORMATION: Synthetic primer

<400> SEQUENCE: 8
ctatgcggcg cgccttatta tttacccgga gacaggggga g                    41

<210> SEQ ID NO 9
<211> LENGTH: 86
<212> TYPE: DNA
<213> ORGANISM: Artificial
<220> FEATURE:
<223> OTHER INFORMATION: Synthetic primer

<400> SEQUENCE: 9
gaaatcccta ttgcctacgg cagccgctgg attgttattg ctagcggctc agccggcaat   60
ggcggaggtc caactggttg aatctg                                       86
```

```
<210> SEQ ID NO 10
<211> LENGTH: 29
<212> TYPE: DNA
<213> ORGANISM: Artificial
<220> FEATURE:
<223> OTHER INFORMATION: Synthetic primer

<400> SEQUENCE: 10
gaagcttgcc gaggagacgg tgaccaggg                                    29

<210> SEQ ID NO 11
<211> LENGTH: 27
<212> TYPE: DNA
<213> ORGANISM: Artificial
<220> FEATURE:
<223> OTHER INFORMATION: Synthetic primer

<400> SEQUENCE: 11
cgtaccactg cggccgcacc atctgtc                                      27

<210> SEQ ID NO 12
<211> LENGTH: 81
<212> TYPE: DNA
<213> ORGANISM: Artificial
<220> FEATURE:
<223> OTHER INFORMATION: Synthetic primer

<400> SEQUENCE: 12
gcttcaacag gggagagtgc taataatata tatatatata tattctagag aaggagatat    60
acatatgaaa tccctattgc c                                              81

<210> SEQ ID NO 13
<211> LENGTH: 35
<212> TYPE: DNA
<213> ORGANISM: Artificial
<220> FEATURE:
<223> OTHER INFORMATION: Synthetic primer

<400> SEQUENCE: 13
agccggccat ggcggatatt cagatgacac agtcc                              35

<210> SEQ ID NO 14
<211> LENGTH: 34
<212> TYPE: DNA
<213> ORGANISM: Artificial
<220> FEATURE:
<223> OTHER INFORMATION: Synthetic primer

<400> SEQUENCE: 14
ggccgcagtg gtacgtttta tttcaacctt ggtg                               34

<210> SEQ ID NO 15
<211> LENGTH: 53
<212> TYPE: DNA
<213> ORGANISM: Artificial
<220> FEATURE:
<223> OTHER INFORMATION: Synthetic primer

<400> SEQUENCE: 15
gttattgcta gcggctcagc cggcaatggc gcaggtggag ctgcagcagt ctg           53

<210> SEQ ID NO 16
<211> LENGTH: 44
<212> TYPE: DNA
<213> ORGANISM: Artificial
<220> FEATURE:
<223> OTHER INFORMATION: Synthetic primer
```

```
<400> SEQUENCE: 16
cccttgaagc ttgcagagct cacagtaaca ctagcaccat gacc                        44

<210> SEQ ID NO 17
<211> LENGTH: 44
<212> TYPE: DNA
<213> ORGANISM: Artificial
<220> FEATURE:
<223> OTHER INFORMATION: Synthetic primer

<400> SEQUENCE: 17
atcgcggccc agccggccat ggcggacata gtactgaccc agtc                        44

<210> SEQ ID NO 18
<211> LENGTH: 36
<212> TYPE: DNA
<213> ORGANISM: Artificial
<220> FEATURE:
<223> OTHER INFORMATION: Synthetic primer

<400> SEQUENCE: 18
gatggtgcgg ccgcagtggc cgatttgatc tcgagc                                 36

<210> SEQ ID NO 19
<211> LENGTH: 119
<212> TYPE: PRT
<213> ORGANISM: Artificial
<220> FEATURE:
<223> OTHER INFORMATION: Synthetic peptide

<400> SEQUENCE: 19
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Glu Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Phe Leu Ile Thr Thr Gly Tyr Phe Asp Tyr Trp Gly Gln Gly
            100                 105                 110

Thr Thr Leu Thr Val Ser Ser
        115

```
<210> SEQ ID NO 20
<211> LENGTH: 108
<212> TYPE: PRT
<213> ORGANISM: Artificial
<220> FEATURE:
<223> OTHER INFORMATION: Synthetic peptide

<400> SEQUENCE: 20
```

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile

```
                35                  40                  45
Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Ile Lys Arg
            100                 105

<210> SEQ ID NO 21
<211> LENGTH: 121
<212> TYPE: PRT
<213> ORGANISM: Artificial
<220> FEATURE:
<223> OTHER INFORMATION: Synthetic peptide

<400> SEQUENCE: 21

Glu Val Gln Leu Val Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly Thr Pro Phe Glu Gly Leu Arg Lys Ala Asp Tyr Trp Gly
            100                 105                 110

Gln Gly Thr Thr Leu Thr Val Ser Ser
        115                 120

<210> SEQ ID NO 22
<211> LENGTH: 108
<212> TYPE: PRT
<213> ORGANISM: Artificial
<220> FEATURE:
<223> OTHER INFORMATION: Synthetic peptide

<400> SEQUENCE: 22

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Arg Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys Arg
            100                 105
```

```
<210> SEQ ID NO 23
<211> LENGTH: 121
<212> TYPE: PRT
<213> ORGANISM: Artificial
<220> FEATURE:
<223> OTHER INFORMATION: Synthetic peptide

<400> SEQUENCE: 23

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Ser Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly Thr Pro Phe Glu Gly Leu Arg Arg Ala Asp Tyr Trp Gly
            100                 105                 110

Gln Gly Thr Thr Leu Thr Val Ser Ser
        115                 120

<210> SEQ ID NO 24
<211> LENGTH: 108
<212> TYPE: PRT
<213> ORGANISM: Artificial
<220> FEATURE:
<223> OTHER INFORMATION: Synthetic peptide

<400> SEQUENCE: 24

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Asn Arg
            100                 105

<210> SEQ ID NO 25
<211> LENGTH: 116
<212> TYPE: PRT
<213> ORGANISM: Artificial
<220> FEATURE:
<223> OTHER INFORMATION: Synthetic peptide

<400> SEQUENCE: 25

Gln Val Gln Leu Lys Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

```
Asp Ile Asn Trp Val Arg Gln Arg Pro Glu Gln Gly Leu Glu Trp Ile
            35                  40                  45

Gly Trp Ile Phe Pro Gly Asp Gly Ser Thr Lys Tyr Asn Glu Lys Phe
 50                  55                  60

Lys Gly Lys Ala Thr Leu Thr Thr Asp Lys Ser Ser Ser Thr Ala Tyr
 65                  70                  75                  80

Met Gln Leu Ser Arg Leu Thr Ser Glu Asp Ser Ala Val Tyr Phe Cys
                 85                  90                  95

Ala Arg Gly Gly Leu Tyr Phe Asp Tyr Trp Gly Gln Gly Thr Thr Leu
                100                 105                 110

Thr Val Ser Ser
        115
```

<210> SEQ ID NO 26
<211> LENGTH: 108
<212> TYPE: PRT
<213> ORGANISM: Artificial
<220> FEATURE:
<223> OTHER INFORMATION: Synthetic peptide

<400> SEQUENCE: 26

```
Asp Ile Gln Met Thr Gln Ser Pro Ser Ser Leu Ser Ala Ser Val Gly
 1               5                  10                  15

Asp Arg Val Thr Val Thr Cys Arg Ala Ser Gln Gly Ile Arg Asn Tyr
            20                  25                  30

Leu Asn Trp Tyr Gln Gln Lys Pro Gly Lys Ala Pro Lys Phe Leu Ile
        35                  40                  45

Tyr Tyr Thr Ser Arg Leu Leu Pro Gly Val Pro Ser Arg Phe Ser Gly
 50                  55                  60

Ser Gly Ser Gly Thr Asp Tyr Thr Leu Thr Ile Asn Ser Leu Glu Gln
 65                  70                  75                  80

Glu Asp Ile Ala Thr Tyr Tyr Cys Gln Gln Gly Asn Thr Pro Pro Trp
                 85                  90                  95

Thr Phe Gly Gln Gly Thr Lys Val Glu Ile Lys Arg
                100                 105
```

<210> SEQ ID NO 27
<211> LENGTH: 118
<212> TYPE: PRT
<213> ORGANISM: Artificial
<220> FEATURE:
<223> OTHER INFORMATION: Synthetic peptide

<400> SEQUENCE: 27

```
Glu Val Lys Leu Gln Gln Ser Gly Pro Glu Leu Val Lys Pro Gly Ala
 1               5                  10                  15

Ser Val Lys Ile Ser Cys Lys Gly Ser Gly Tyr Ala Ile Ser Ser Ser
            20                  25                  30

Trp Met Asn Trp Val Lys Gln Arg Pro Gly Gln Gly Pro Glu Trp Ile
        35                  40                  45

Gly Arg Ile Tyr Pro Gly Asp Gly Asp Thr Asn Tyr Asn Gly Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Val Asp Ser Ala Val Tyr Phe Cys
                 85                  90                  95

Ala Arg Gly Gly Leu Pro Tyr Ala Val Asp Tyr Trp Gly Gln Gly Thr
                100                 105                 110
```

Ser Val Thr Val Ser Ser
    115

<210> SEQ ID NO 28
<211> LENGTH: 21
<212> TYPE: DNA
<213> ORGANISM: Artificial
<220> FEATURE:
<223> OTHER INFORMATION: Synthetic primer

<400> SEQUENCE: 28
cggataacaa tttcacacag g                                         21

<210> SEQ ID NO 29
<211> LENGTH: 21
<212> TYPE: DNA
<213> ORGANISM: Artificial
<220> FEATURE:
<223> OTHER INFORMATION: Synthetic primer

<400> SEQUENCE: 29
agttccacga caccgtcacc g                                         21

<210> SEQ ID NO 30
<211> LENGTH: 108
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (71)..(71)
<223> OTHER INFORMATION: n is a, c, g, or t

<400> SEQUENCE: 30
gatggtgcgg ccgcagtacg tttaatctcc agcttggtcc cagcaccgaa cgtgwraggg   60
kdgykgkhgy nmtkctgaca gaaataatct gccaagtctt cagactgc              108

<210> SEQ ID NO 31
<211> LENGTH: 113
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 31
cccttgaagc ttgctgagga gactgtgaga gtggtgcctt ggccccagta gkcmawgbvg   60
bvgdvgbmmy hgwngbngnn mnvtssgkya cagtaataga cggcagtgtc ctc         113

<210> SEQ ID NO 32
<211> LENGTH: 110
<212> TYPE: DNA
<213> ORGANISM: Artificial

<220> FEATURE:
<223> OTHER INFORMATION: Synthetic primer
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 32
cccttgaagc ttgctgagga gactgtgaga gtggtgcctt ggccccagta gkcmawgbvg    60
bvgdvgbmmy hgbngnnmnv tssgkyacag taatagacgg cagtgtcctc             110

<210> SEQ ID NO 33
<211> LENGTH: 107
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 33
cccttgaagc ttgctgagga gactgtgaga gtggtgcctt ggccccagta gkcmawgbvg    60
bvgdvgbmgb ngnnmnvtss gkyacagtaa tagacggcag tgtcctc                107

<210> SEQ ID NO 34
<211> LENGTH: 104
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 34
cccttgaagc ttgctgagga gactgtgaga gtggtgcctt ggccccagta gkcmawgbvg    60
bvgdvgbngn nmnvtssgky acagtaatag acggcagtgt cctc                   104

<210> SEQ ID NO 35
<211> LENGTH: 101
<212> TYPE: DNA
<213> ORGANISM: Artificial
<220> FEATURE:
<223> OTHER INFORMATION: Synthetic primer

```
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 35
cccttgaagc ttgctgagga gactgtgaga gtggtgcctt ggccccagta gkcmawgbvg     60
bvgbngnnmn vtssgkyaca gtaatagacg gcagtgtcct c                        101

<210> SEQ ID NO 36
<211> LENGTH: 98
<212> TYPE: DNA
<213> ORGANISM: Artificial
<220> FEATURE:
<223> OTHER INFORMATION: Synthetic primer
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 36
cccttgaagc ttgctgagga gactgtgaga gtggtgcctt ggccccagta gkcmawgbvg     60
bngnnmnvts sgkyacagta atagacggca gtgtcctc                            98

<210> SEQ ID NO 37
<211> LENGTH: 21
<212> TYPE: DNA
<213> ORGANISM: Artificial
<220> FEATURE:
<223> OTHER INFORMATION: Synthetic primer

<400> SEQUENCE: 37
tggataacgc cctccaatcg g                                              21

<210> SEQ ID NO 38
<211> LENGTH: 9
<212> TYPE: PRT
<213> ORGANISM: Artificial
<220> FEATURE:
<223> OTHER INFORMATION: Synthetic peptide

<400> SEQUENCE: 38

Gln Gln Tyr Ser Ser Tyr Pro Leu Thr
1               5

<210> SEQ ID NO 39
<211> LENGTH: 12
<212> TYPE: PRT
<213> ORGANISM: Artificial
<220> FEATURE:
<223> OTHER INFORMATION: Synthetic peptide

<400> SEQUENCE: 39
```

```
Gly Thr Pro Phe Glu Gly Leu Arg Arg Ala Asp Tyr
1               5                   10
```

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

```
Gln Asn His Asp His His Pro His Thr
1               5
```

<210> SEQ ID NO 41
<211> LENGTH: 10
<212> TYPE: PRT
<213> ORGANISM: Artificial
<220> FEATURE:
<223> OTHER INFORMATION: Synthetic peptide

<400> SEQUENCE: 41

```
Leu Pro Pro Asp Phe Arg Ala Ile Ala Tyr
1               5                   10
```

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

```
Gln Asn His Thr Ser Pro Ser His Thr
1               5
```

<210> SEQ ID NO 43
<211> LENGTH: 10
<212> TYPE: PRT
<213> ORGANISM: Artificial
<220> FEATURE:
<223> OTHER INFORMATION: Synthetic peptide

<400> SEQUENCE: 43

```
Val Leu Tyr Asp Ser Ser Gly Leu Ala Tyr
1               5                   10
```

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

```
Gln Asn His Thr His Pro Pro Leu Thr
1               5
```

<210> SEQ ID NO 45
<211> LENGTH: 10
<212> TYPE: PRT
<213> ORGANISM: Artificial
<220> FEATURE:
<223> OTHER INFORMATION: Synthetic peptide

<400> SEQUENCE: 45

```
Leu Tyr Ser Cys Tyr Tyr Pro Phe Ala Tyr
1               5                   10
```

```
<210> SEQ ID NO 46
<211> LENGTH: 9
<212> TYPE: PRT
<213> ORGANISM: Artificial
<220> FEATURE:
<223> OTHER INFORMATION: Synthetic peptide

<400> SEQUENCE: 46

Gln Gln Gly Tyr His Ser Pro His Thr
1               5

<210> SEQ ID NO 47
<211> LENGTH: 11
<212> TYPE: PRT
<213> ORGANISM: Artificial
<220> FEATURE:
<223> OTHER INFORMATION: Synthetic peptide

<400> SEQUENCE: 47

Val Arg Leu His Asp Phe Cys Ser Leu Ala Tyr
1               5                   10
```